US006670133B2

(12) United States Patent
Knapp et al.

(10) Patent No.: US 6,670,133 B2
(45) Date of Patent: Dec. 30, 2003

(54) MICROFLUIDIC DEVICE FOR SEQUENCING BY HYBRIDIZATION

(75) Inventors: Michael Knapp, Redwood City, CA (US); John Wallace Parce, Palo Alto, CA (US); Luc J. Bousse, Menlo Park, CA (US); Anne R. Kopf-Sill, Portola Valley, CA (US)

(73) Assignee: Caliper Technologies Corp., Mountain View, CA (US)

( * ) Notice: Subject to any disclaimer, the term of this patent is extended or adjusted under 35 U.S.C. 154(b) by 36 days.

(21) Appl. No.: 10/197,724

(22) Filed: Jul. 17, 2002

(65) Prior Publication Data

US 2003/0148922 A1 Aug. 7, 2003

Related U.S. Application Data

(60) Continuation of application No. 09/666,948, filed on Sep. 20, 2000, now Pat. No. 6,444,461, which is a division of application No. 09/054,962, filed on Apr. 3, 1998, now Pat. No. 6,235,471.
(60) Provisional application No. 60/068,311, filed on Dec. 19, 1997, and provisional application No. 60/086,240, filed on Apr. 4, 1997.

(51) Int. Cl.[7] .............................................. G01M 31/00
(52) U.S. Cl. .......................................................... 435/6
(58) Field of Search ........................... 435/6, 7.1, 91.1, 435/91.2, 285.1, 287.2; 436/518; 536/22.1, 23.1, 24.3–24.33

(56) References Cited

U.S. PATENT DOCUMENTS

| | | | |
|---|---|---|---|
| 4,390,403 A | 6/1983 | Batchelder | 204/180 R |
| 4,889,818 A | 12/1989 | Gelfand et al. | 435/194 |
| 4,908,112 A | 3/1990 | Pace | 204/299 R |

(List continued on next page.)

FOREIGN PATENT DOCUMENTS

| | | | |
|---|---|---|---|
| WO | WO 94/16107 | 7/1994 | |
| WO | WO 96/04547 | 2/1996 | G01N/27/00 |
| WO | WO 96/07917 | 3/1996 | G01N/35/00 |
| WO | WO 96/30934 | 10/1996 | |
| WO | WO 97/02357 | 1/1997 | C12P/19/34 |
| WO | WO 98/00231 | 1/1998 | |
| WO | WO 98/00705 | 1/1998 | |
| WO | WO 98/00707 | 1/1998 | |
| WO | WO 98/02728 | 1/1998 | |
| WO | WO 98/05424 | 2/1998 | |
| WO | WO 98/22811 | 5/1998 | |
| WO | WO 98/45481 | 10/1998 | |
| WO | WO 98/45929 | 10/1998 | |

OTHER PUBLICATIONS

Barinaga Science vol. 253 pp. 1489 1991.*
Powell in PCR Essential Data Protocol Optimization and Reaction Specificity, pp. 72–86 1995.

Rawaldi et al., "Application of an arbitrarily–primed polymerase chain reaction to mycoplasma identification and typing within the Mycoplasma mycoides cluster" *J. of Applied Bacteriology* 1995, 78, 586–592.

Skowasch et al., "Optimized amlification of the polymorphic system COL2A1" *Int. J. Leg. Med.* (1992) 105:185–187.

Thomas et al., "An improved strategy for generating Sequence Protocol for Double Stranded DNA" Methods in Molecular and Cellular Biology 3:39–42 (1992).

Dasgupta et al., "Electroosmosis: A Reliable fluid Propulsion System for Flow Injection Analysis", *Anal. Chem.* 66:1792–1798 (1994).

Jacobson et al., "Fused Quartz Substrates for Microchip Electrophoresis", *Anal. Chem.* 67:2059–2063 (1995).

Kaczorowski et al., "Assembly of 18–Nucleotide Primers by Ligation of Three Hexamers: Sequencing of Large Genomes by Primer Walking", *Analytical Biochemistry* 221:127–135 (1994).

Kaczorowski et al., Co–operativity of hexamer ligation[1], *Gene* 179:189–193 (1996).

Kaczorowski et al., "Automated four–color DNA sequencing using primers assembled by hexamer ligation[1]", *Gene* 179:195–198 (1996).

Manz et al., "Electroosmotic pumping and electrophoretic separations for miniaturized chemical analysis systems", *J. Micromech. Microeng.* 4:257–265 (1994).

Porter et al., "Direct PCR sequencing with boronated nucleotides", *Nucleic Acids Research* 25:8 1611–1617, (1997).

Ramsey et al., "Microfabricated chemical measurement systems", *Nature Medicine* 1:10 1093–1096 (1995).

Seiler et al., "Planar Glass Chips for Capillary Electrophoresis: Repetitive Sample Injection, Quantitation, and Separation Efficiency", *Anal. Chem.* 65:1481–1488 (1993).

Seller et al., "Electroosmotic Pumping and Valveless Control of Fluid Flow within a Manifold of Capillaries on a Glass Chip", *Anal. Chem.* 66:3485–3491 (1994).

Karger et al., "Multiwavelength flourescence detection for DNA sequencing using capillary electrophoresis" *Nucleic Acid Research* vol. 19, No. 18 pp. 4955–4962.

Zimmerman, et al., "Fully Automated Sanger Sequence Protocol for Double Stranded DNA" *Methods in Molecular and Cellular Biology* 3:39–42 (1992).

*Primary Examiner*—Jeffrey Siew
(74) *Attorney, Agent, or Firm*—Quine Intellectual Property Law Group, P.C.; Andrew L. Filler; Angela P. Horne

(57) ABSTRACT

Integrated systems, apparatus, software, and methods for performing biochemical analysis, including DNA sequencing, genomic screening, purification of nucleic acids and other biological components and drug screening are provided. Microfluidic devices, systems and methods for using these devices and systems for performing a wide variety of fluid operations are provided. The devices and systems of are used in performing fluid operations which require a large number of iterative, successive or parallel fluid manipulations, in a microscale, or sealed and readily automated format.

61 Claims, 24 Drawing Sheets

U.S. PATENT DOCUMENTS

| | | | |
|---|---|---|---|
| 4,965,188 A | 10/1990 | Mullis et al. | 435/6 |
| 5,043,272 A | 8/1991 | Hartley | |
| 5,066,584 A | 11/1991 | Gyllensten et al. | 435/91 |
| 5,075,216 A | 12/1991 | Innis et al. | 435/6 |
| 5,077,192 A | 12/1991 | Liang et al. | 435/7.1 |
| 5,079,352 A | 1/1992 | Gelfand et al. | 536/27 |
| 5,126,021 A | 6/1992 | Grossman | |
| 5,126,022 A | 6/1992 | Soane et al. | 204/180.1 |
| 5,154,888 A | 10/1992 | Zander et al. | 422/58 |
| 5,229,297 A | 7/1993 | Schnipelsky et al. | 436/94 |
| 5,230,866 A | 7/1993 | Shartle et al. | 422/103 |
| 5,288,463 A | 2/1994 | Chemelli | 422/58 |
| 5,350,672 A | 9/1994 | Oberst et al. | 435/6 |
| 5,352,600 A | 10/1994 | Gelfand et al. | 435/194 |
| 5,376,252 A | 12/1994 | Ekstrom et al. | 204/299 R |
| 5,405,746 A | 4/1995 | Uhlen | 435/6 |
| 5,422,271 A | 6/1995 | Chen et al. | 435/287 |
| 5,486,335 A | 1/1996 | Wilding et al. | 422/55 |
| 5,496,699 A | 3/1996 | Sorenson | 435/6 |
| 5,498,392 A | 3/1996 | Wilding et al. | 422/68.1 |
| 5,500,187 A | 3/1996 | Deoms et al. | 422/58 |
| 5,501,963 A | 3/1996 | Burckhardt | 435/91.2 |
| 5,508,169 A | 4/1996 | Deugau et al. | 435/6 |
| 5,512,439 A | 4/1996 | Hornes et al. | 435/6 |
| 5,514,550 A | 5/1996 | Findlay et al. | 436/6 |
| 5,521,065 A * | 5/1996 | Whiteley | 435/6 |
| 5,523,204 A | 6/1996 | Singer et al. | |
| 5,527,670 A | 6/1996 | Stanley | 435/6 |
| 5,534,406 A | 7/1996 | Liang et al. | 435/5 |
| 5,534,424 A | 7/1996 | Uhlen et al. | 435/91.2 |
| 5,545,531 A * | 8/1996 | Rava et al. | 435/6 |
| 5,547,835 A | 8/1996 | Koster | 435/6 |
| 5,556,790 A | 9/1996 | Pettit | |
| 5,571,410 A | 11/1996 | Swedberg et al. | 210/198.2 |
| 5,573,906 A | 11/1996 | Bannwarth et al. | 435/6 |
| 5,585,069 A | 12/1996 | Zanzucchi et al. | 422/100 |
| 5,587,128 A | 12/1996 | Wilding et al. | 422/50 |
| 5,593,838 A | 1/1997 | Zanzucchi et al. | 435/6 |
| 5,603,351 A | 2/1997 | Cherukuri et al. | 137/597 |
| 5,635,358 A | 6/1997 | Wilding et al. | 435/7.2 |
| 5,637,469 A | 6/1997 | Wilding et al. | 435/7.21 |
| 5,639,423 A | 6/1997 | Northrup et al. | 122/50 |
| 5,652,149 A | 7/1997 | Mileaf et al. | 436/518 |
| 5,674,743 A | 10/1997 | Ulmer | 435/287.2 |
| 5,677,197 A | 10/1997 | Gordon et al. | 436/518 |
| 5,681,484 A | 10/1997 | Zanzucchi et al. | 216/2 |
| 5,695,940 A * | 12/1997 | Drmanac et al. | 435/6 |
| 5,698,406 A | 12/1997 | Cathey et al. | 435/7.9 |
| 5,699,157 A | 12/1997 | Parce | |
| 5,714,380 A | 2/1998 | Neri et al. | 435/287.2 |
| 5,716,825 A | 2/1998 | Hancock et al. | 435/286.5 |
| 5,723,345 A | 3/1998 | Yamauchi et al. | 436/518 |
| 5,731,212 A | 3/1998 | Gavin et al. | 436/526 |
| 5,741,640 A | 4/1998 | Fuller | |
| 5,741,678 A | 4/1998 | Ronai | |
| 5,750,015 A | 5/1998 | Soane et al. | 284/454 |
| 5,773,298 A | 6/1998 | Lynggaard et al. | |
| 5,779,868 A * | 7/1998 | Parce et al. | 204/604 |
| 5,780,754 A | 7/1998 | Karlberg et al. | |
| 5,800,690 A | 9/1998 | Chow et al. | |
| 5,842,787 A | 12/1998 | Kopf-Sill et al. | |
| 5,852,495 A | 12/1998 | Parce | |
| 5,863,502 A | 1/1999 | Southgate et al. | |
| 5,880,071 A | 3/1999 | Parce et al. | |
| 5,885,470 A | 3/1999 | Parce et al. | |
| 5,908,755 A | 6/1999 | Kumar et al. | |
| 5,922,604 A | 7/1999 | Stapleton et al. | |
| 5,942,443 A | 8/1999 | Parce et al. | |
| 5,948,673 A | 9/1999 | Cottingham | |
| 5,955,028 A | 9/1999 | Chow | |
| 5,955,029 A | 9/1999 | Wilding et al. | |
| 5,958,203 A | 9/1999 | Parce et al. | |
| 5,958,694 A | 9/1999 | Nikiforov | |
| 5,965,001 A | 10/1999 | Chow et al. | |
| 5,972,187 A | 10/1999 | Parce et al. | |
| 6,001,229 A | 12/1999 | Ramsey | |
| 6,042,709 A | 3/2000 | Parce et al. | |
| 6,043,059 A | 3/2000 | Reeves et al. | |
| 6,046,056 A | 4/2000 | Parce et al. | |
| 6,054,270 A | 4/2000 | Southern | |
| 6,071,478 A | 6/2000 | Chow | |
| 6,080,295 A | 6/2000 | Parce et al. | |
| 6,083,763 A * | 7/2000 | Balch | 436/518 |
| 6,096,499 A | 8/2000 | Kozlowski et al. | |
| 6,235,471 B1 | 5/2001 | Knapp et al. | |

* cited by examiner

NO SAMPLE
NO ANTIBODIES

NO SAMPLE

WITH SAMPLE

PEAK HEIGHTS ARE
RELATED TO ANALYTE
CONCENTRATION

SERIAL

PARALLEL

MICROFLUIDIC DEVICE FOR SEQUENCING BY HYBRIDIZATION

CROSS REFERENCE TO RELATED APPLICATIONS

This application is a continuation-in-part of provisional patent application U.S. Ser. No. 60/068,311, entitled "Closed Loop Biochemical Analyzer" by Knapp, filed Dec. 19, 1997. The subject application is also a continuation-in-part of U.S. Ser. No. 08/835,101 by Knapp et al. filed Apr. 4, 1997 (converted to a provisional application by filing a petition under 37 C.F.R. §§1.53(C) and 1.17(a) on Jan. 20, 1998), entitled "Microfluidic Devices and Systems for Performing Integrated Fluid Operations." Both of these applications are incorporated herein by reference in their entirety for all purposes.

FIELD OF THE INVENTION

This application relates to apparatus, methods and integrated systems for detecting molecular interactions. The apparatus comprise microscale devices for moving and mixing small fluid volumes. The systems are capable of performing integrated manipulation and analysis in a variety of biological, biochemical and chemical experiments, including, e.g., DNA sequencing.

BACKGROUND OF THE INVENTION

Manipulating fluidic reagents and assessing the results of reagent interactions are central to chemical and biological science. Manipulations include mixing fluidic reagents, assaying products resulting from such mixtures, and separation or purification of products or reagents and the like. Assessing the results of reagent interactions can include autoradiography, spectroscopy, microscopy, photography, mass spectrometry, nuclear magnetic resonance and many other techniques for observing and recording the results of mixing reagents. A single experiment can involve literally hundreds of fluidic manipulations, product separations, result recording processes and data compilation and integration steps. Fluidic manipulations are performed using a wide variety of laboratory equipment, including various fluid heating devices, fluidic mixing devices, centrifugation equipment, molecule purification apparatus, chromatographic machinery, gel electrophoretic equipment and the like. The effects of mixing fluidic reagents are typically assessed by additional equipment relating to detection, visualization or recording of an event to be assayed, such as spectrophotometers, autoradiographic equipment, microscopes, gel scanners, computers and the like.

Because analysis of even simple chemical, biochemical, or biological phenomena requires many different types of laboratory equipment, the modern laboratory is complex, large and expensive. In addition, because so many different types of equipment are used in even conceptually simple experiments such as DNA sequencing, it has not generally been practical to integrate different types of equipment to improve automation. The need for a laboratory worker to physically perform many aspects of laboratory science imposes sharp limits on the number of experiments which a laboratory can perform, and increases the undesirable exposure of laboratory workers to toxic or radioactive reagents. In addition, results are often analyzed manually, with the selection of subsequent experiments related to initial experiments requiring consideration by a laboratory worker, severely limiting the throughput of even repetitive experimentation.

In an attempt to increase laboratory throughput and to decrease exposure of laboratory workers to reagents, various strategies have been performed. For example, robotic introduction of fluids onto microtiter plates is commonly performed to speed mixing of reagents and to enhance experimental throughput. More recently, microscale devices for high throughput mixing and assaying of small fluid volumes have been developed. For example, U.S. Pat. No. 6,046,056 provides pioneering technology related to microscale fluidic devices, especially including electrokinetic devices. The devices are generally suitable for assays relating to the interaction of biological and chemical species, including enzymes and substrates, ligands and ligand binders, receptors and ligands, antibodies and antibody ligands, as well as many other assays. Because the devices provide the ability to mix fluidic reagents and assay mixing results in a single continuous process, and because minute amounts of reagents can be assayed, these microscale devices represent a fundamental advance for laboratory science.

In the electrokinetic microscale devices provided by Parce et al. above, an appropriate fluid is flowed into a microchannel etched in a substrate having functional groups present at the surface. The groups ionize when the surface is contacted with an aqueous solution. For example, where the surface of the channel includes hydroxyl functional groups at the surface, e.g., as in glass substrates, protons can leave the surface of the channel and enter the fluid. Under such conditions, the surface possesses a net negative charge, whereas the fluid will possess an excess of protons, or positive charge, particularly localized near the interface between the channel surface and the fluid. By applying an electric field along the length of the channel, cations will flow toward the negative electrode. Movement of the sheath of positively charged species in the fluid pulls the solvent with them.

One time consuming process is titration of biological and biochemical assay components into the dynamic range of an assay. For example, because enzyme activities vary from lot to lot, it is necessary to perform a titration of enzyme and substrate concentrations to determine optimum reaction conditions. Similarly, diagnostic assays require titration of unknown concentrations of components so that the assay can be performed using appropriate concentrations of components. Thus, even before performing a typical diagnostic assay, several normalization steps need to be performed with assay components.

Another labor intensive laboratory process is the selection of lead compounds in drug screening assays. Various approaches to screening for lead compounds are reviewed by Janda (1994) *Proc. Natl. Acad. Sci. USA* 91(10779–10785); Blondelle (1995) *Trends Anal. Chem* 14:83–91; Chen et al. (1995) *Angl. Chem. Int. Engl.* 34:953–960; Ecker et al. (1995) *Bio/Technology* 13:351–360; Gordon et al. (1994) *J. Med. Chem.* 37:1385–1401 and Gallop et al. (1994) *J. Med. Chem.* 37:1233–1251. Improvements in screening have been developed by combining one or more steps in the screening process, e.g., affinity capillary electrophoresis-mass spectrometry for combinatorial library screening (Chu et al. (1996) *J. Am. Chem. Soc.* 118:7827–7835). However, these high-throughput screening methods do not provide an integrated way of selecting a second assay or screen based upon the results of a first assay or screen. Thus, results from one assay are not automatically used to focus subsequent experimentation and experimental design still requires a large input of labor by the user.

Another particularly labor intensive biochemical series of laboratory fluidic manipulations is nucleic acid sequencing.

Efficient DNA sequencing technology is central to the development of the biotechnology industry and basic biological research. Improvements in the efficiency and speed of DNA sequencing are needed to keep pace with the demands for DNA sequence information. The Human Genome Project, for example, has set a goal of dramatically increasing the efficiency, cost-effectiveness and throughput of DNA sequencing techniques. See, e.g., Collins, and Galas (1993) *Science* 262:43–46.

Most DNA sequencing today is carried out by chain termination methods of DNA sequencing. The most popular chain termination methods of DNA sequencing are variants of the dideoxynucleotide mediated chain termination method of Sanger. See, Sanger et al. (1977) *Proc. Nat. Acad. Sci., USA* 74:5463–5467. For a simple introduction to dideoxy sequencing, see, *Current Protocols in Molecular Biology*, F. M. Ausubel et al., eds., Current Protocols, a joint venture between Greene Publishing Associates, Inc. and John Wiley & Sons, Inc., (Supplement 37, current through 1997) (Ausubel), Chapter 7. Four color sequencing is described in U.S. Pat. No. 5,171,534. Thousands of laboratories employ dideoxynucleotide chain termination techniques. Commercial kits containing the reagents most typically used for these methods of DNA sequencing are available and widely used.

In addition to the Sanger methods of chain termination, new PCR exonuclease digestion methods have also been proposed for DNA sequencing. Direct sequencing of PCR generated amplicons by selectively incorporating boronated nuclease resistant nucleotides into the amplicons during PCR and digestion of the amplicons with a nuclease to produce sized template fragments has been proposed (Porter et al. (1997) *Nucleic Acids Research* 25(8):1611–1617). In the methods, 4 PCR reactions on a template are performed, in each of which one of the nucleotide triphosphates in the PCR reaction mixture is partially substituted with a 2'-deoxynucleoside 5'-α[P-borano]-triphosphate. The boronated nucleotide is stocastically incorporated into PCR products at varying positions along the PCR amplicon in a nested set of PCR fragments of the template. An exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it requires fewer biochemical manipulations than performing standard Sanger-style sequencing of PCR amplicons.

Other sequencing methods which reduce the number of steps necessary for template preparation and primer selection have been developed. One proposed variation on sequencing technology involves the use of modular primers for use in PCR and DNA sequencing. For example, Ulanovsky and co-workers have described the mechanism of the modular primer effect (Beskin et al. (1995) *Nucleic Acids Research* 23(15):2881–2885) in which short primers of 5–6 nucleotides can specifically prime a template-dependent polymerase enzyme for template dependent nucleic acid synthesis. A modified version of the use of the modular primer strategy, in which small nucleotide primers are specifically elongated for use in PCR to amplify and sequence template nucleic acids has also been described. The procedure is referred to as DNA sequencing using differential extension with nucleotide subsets (DENS). See, Raja et al. (1997) *Nucleic Acids Research* 25(4):800–805.

In addition to enzymatic and other chain termination sequencing methods, sequencing by hybridization to complementary oligonucleotides has been proposed, e.g., in U.S. Pat. No. 5,202,231, to Drmanac et al. and, e.g., in Drmanac et al. (1989) *Genomics* 4:114–128. Chemical degradation sequencing methods are also well known and still in use; see, Maxam and Gilbert (1980) in Grossman and Moldave (eds.) Academic Press, New York, *Methods in Enzymology* 65:499–560.

Improvements in methods for generating sequencing templates have also been developed. DNA sequencing typically involves three steps: i) making suitable templates for the regions to be sequenced; ii) running sequencing reactions for electrophoresis and iii) assessing the results of the reaction. The latter steps are sometimes automated by use of large and very expensive workstations and autosequencers. The first step often requires careful experimental design and laborious DNA manipulation such as the construction of nested deletion mutants. See, Griffin, H. G. and Griffin, A. M. (1993) *DNA sequencing protocols*, Humana Press, New Jersey. Alternatively, random "shot-gun" sequencing methods, are sometimes used to make templates, in which randomly selected sub clones, which may or may not have overlapping sequence information, are randomly sequenced. The sequences of the sub clones are compiled to produce an ordered sequence. This procedures eliminates complicated DNA manipulations; however, the method is inherently inefficient because many recombinant clones must be sequenced due to the random nature of the procedure. Because of the labor intensive nature of sequencing, the repetitive sequencing of many individual clones dramatically reduces the throughput of these sequencing systems.

Recently, Hagiwara and Curtis (1996) *Nucleic Acids Research* 24(12):2460–2461 developed a "long distance sequencer" PCR protocol for generating overlapping nucleic acids from very large clones to facilitate sequencing, and methods of amplifying and tagging the overlapping nucleic acids into suitable sequencing templates. The methods can be used in conjunction with shotgun sequencing techniques to improve the efficiency of shotgun methods.

Although improvements in robotic manipulation of fluidic reagents and miniaturization of laboratory equipment have been made, and although particular biochemical processes such as DNA sequencing and drug screening are very well developed, there still exists a need for additional techniques and apparatus for mixing and assaying fluidic reagents, for integration of such systems and for reduction of the number of manipulations required to perform biochemical manipulations such as drug screening and DNA sequencing. Ideally, these new apparatus would be useful with, and compatible to, established biochemical protocols. This invention provides these and many other features.

SUMMARY OF THE INVENTION

This invention provides apparatus, systems and methods for integrated manipulation and analysis of fluidic reagents. The integrated features provide very high throughput methods of assessing biochemical components and performing biochemical manipulations. A wide variety of reagents and products are suitably assessed, including libraries of chemical or biological compounds or components, nucleic acid templates, PCR reaction products, and the like. In the integrated systems it is possible to use the results of a first reaction or set of reactions to select appropriate reagents, reactants, products, or the like, for additional analysis. For example, the results of a first sequencing reaction can be used to select primers, templates or the like for additional sequencing, or to select related families of compounds for screening in high-throughput assay methods. These primers or templates are then accessed by the system and the process continues.

In one aspect, the invention provides integrated methods of analyzing and manipulating sample materials for fluidic analysis. In the methods, an integrated microfluidic system including a microfluidic device is provided. The device has at least a first reaction channel and at least a first reagent introduction channel, typically etched, machined, printed, or otherwise manufactured in or on a substrate. Optionally, the device can have a second reaction channel and/or reagent introduction channel, a third reaction channel and/or reagent introduction channel or the like, up to and including hundreds or even thousands of reaction and/or reagent introduction channels. The reaction channel and reagent introduction channels are in fluid communication, i.e., fluid can flow between the channels under selected conditions. The device has a material transport system for controllably transporting a material through and among the reagent introduction channel and reaction channel. For example, the material transport system can include electrokinetic, electroosmotic, electrophoretic or other fluid manipulation aspects (micro-pumps and microvalves, fluid switches, fluid gates, etc.) which permit controlled movement and mixing of fluids. The device also has a fluidic interface in fluid communication with the reagent introduction channel. Such fluidic interfaces optionally include capillaries, channels, pins, pipettors, electropipettors, or the like, for moving fluids, and optionally further include microscopic, spectroscopic, fluid separatory or other aspects. The fluidic interface samples a plurality of reagents or mixtures of reagents from a plurality of sources of reagents or mixtures of reagents and introduces the reagents or mixtures of reagents into the reagent introduction channel. Essentially any number of reagents or reagent mixtures can be introduced by the fluidic interface, depending on the desired application. Because microfluidic manipulations are performed in a partially or fully sealed environment, contamination and fluidic evaporation in the systems are minimized.

In the methods, a first reagent from the plurality of sources of reagent or mixtures of reagents is selected. A first sample material and the first reagent or mixture of reagents is introduced into the first reaction channel, whereupon the first sample material and the first reagent or mixture of reagents react. This reaction can take a variety of different forms depending on the nature of the reagents. For example, where the reagents bind to one another, such as where the reagents are an antibody or cell receptor and a ligand, or an amino acid and a binding ligand, the reaction results in a bound component such as a bound ligand. Where the reagents are sequencing reagents, a primer extension product results from the reaction. Where the reagents include enzymes and enzyme substrates, a modified form of the substrate typically results. Where two reacting chemical reagents are mixed, a third product chemical typically results.

In the methods, a reaction product of the first sample material and the first reagent or mixture of reagents is analyzed. This analysis can take any of a variety of forms, depending on the application. For example, where the product is a primer extension product, the analysis can take the form of separating reactants by size, detecting the sized reactants and translating the resulting information to give the sequence of a template nucleic acid. Similarly, because microscale fluidic devices of the invention are optionally suitable for heating and cooling a reaction, a PCR reaction utilizing PCR reagents (thermostable polymerase, nucleotides, templates, primers, buffers and the like) can be performed and the PCR reagents detected. Where the reaction results in the formation of a new product, such as an enzyme-substrate product, a chemical species, or an immunological component such as a bound ligand, the product is typically detected by any of a variety of detection techniques, including autoradiography, microscopy, spectroscopy, or the like.

Based upon the reaction product, a second reagent or mixture of reagents is selected and a second sample material is assessed. For example, where the product is a DNA sequence, a sequencing primer and/or template for extension of available sequence information is selected. Where the product is a new product such as those above, an appropriate second component such as an enzyme, ligand, antibody, receptor molecule, chemical, or the like, is selected to further test the binding or reactive characteristics of an analyzed material. The second reagent or mixture of reagents is introduced into the first reaction channel, or optionally into a second (or third or fourth . . . or nth) reaction channel in the microfluidic device. The second sample material and the second reagent or mixture of reagents react, forming a new product, which is analyzed as above. The results of the analysis can serve as the basis for the selection and analysis of additional reactants for similar subsequent analysis. The second sample material, reagents, or mixtures of reagents can comprise the same or different materials. For example, a single type of DNA template is optionally sequenced in several serial reactions. Alternatively, completing a first sequencing reaction, as outlined above, serves as the basis for selecting additional templates (e.g., overlapping clones, PCR amplicons, or the like).

Accordingly, in a preferred aspect, the invention provides methods of sequencing a nucleic acid. In the methods, the biochemical components of a sequencing reaction (e.g., a target nucleic acid, a first and optionally, second sequencing primer, a polymerase (optionally including thermostable polymerases for use in PCR), dNTPs, and ddNTPs) are mixed in a microfluidic device under conditions permitting target dependent polymerization of the dNTPs. Polymerization products are separated in the microfluidic device to provide a sequence of the target nucleic acid. Typically, sequencing information acquired by this method is used to select additional sequencing primers and/or templates, and the process is reiterated. Generally, a second sequencing primer is selected based upon the sequence of the target nucleic acid and the second sequencing primer is mixed with the target nucleic acid in a microfluidic device under conditions permitting target dependent elongation of the selected second sequencing primer, thereby providing polymerization products which are separated by size in the microfluidic device to provide further sequence of the target nucleic acid. As discussed above, the systems for mixing the biochemical sequencing components, separating the reaction products, and assessing the results of the sequencing reaction are integrated into a single system.

In one integrated sequencing system, methods of sequencing a target nucleic acid are provided in which an integrated microfluidic system comprising a microfluidic device is utilized in the sequencing method. The integrated microfluidic device has at least a first sequencing reaction channel and at least a first sequencing reagent introduction channel, the sequencing reaction channel and sequencing reagent introduction channel being in fluid communication. The integrated microfluidic system also has a material transport system for controllably transporting sequencing reagents through the sequencing reagent introduction channel and sequencing reaction channel and a fluidic interface in fluid communication with the sequencing reagent introduction channel for sampling a plurality of sequencing reagents, or mixtures of sequencing reagents, from a plurality of sources of sequencing reagents or mixtures of sequencing reagents and introducing the sequencing reagents or mixtures of sequencing reagents into the sequence reagent introduction channel. As discussed above, the interface optionally includes capillaries, pins, pipettors and the like. In the method, a first sequencing primer sequence complementary to a first subsequence of a first target nucleic acid sequence is introduced into the sequence reagent introduction channel. The first primer is hybridized to the first subsequence and the first primer is extended with a polymerase enzyme along the length of the target nucleic acid sequence to form a first extension product that is complementary to the first subsequence and a second subsequence of the target nucleic acid. The sequence of the first extension product is determined and, based upon the sequence of the first extension product, a second primer sequence complementary to a second subsequence of the target nucleic acid sequence is selected, hybridized and extended as above.

In the sequence methods herein, it is sometimes advantageous to have select sequencing primers from a large set of sequencing primers, rather than synthesizing primers to match a particular target nucleic acid. For example, 5 or 6-mer primers can be made to hybridize specifically to a target, e.g., where the primers are modular and hybridize to a single region of a nucleic acid. All possible 5 or 6 mers can be synthesized for selection in the methods herein, or any subset of 5 or 6 mers can also be selected. In some embodiments, the primers are transferred to the microfluidic apparatus, e.g., by a capillary, an electropipettor, or using sipping technology, from a microtiter plate or from and array of oligos. In other embodiments, the primers are located on a region of a microfluidic device, chip or other substrate.

An advantage of these sequencing methods is that they dramatically increase the speed with which sequencing reactions can be performed. An entire sequencing reaction, separation of sequencing products and sequence generation can be performed in less than an hour, often less than 30 minutes, generally less than 15 minutes, sometimes less than 10 minutes and occasionally less than 5 minutes.

The present invention provides integrated systems and apparatus for performing the sequencing methods herein. In one embodiment, the invention provides a sequencing apparatus. The apparatus has a top portion, a bottom portion and an interior portion. The interior portion has at least two intersecting channels (and often tens, hundreds, or thousands of intersecting channels), wherein at least one of the two intersecting channels has at least one cross sectional dimension between about 0.1 $\mu$m and 500 $\mu$m. A preferred embodiment of the invention includes an electrokinetic fluid direction system for moving a sequencing reagent through at least one of the two intersecting channels. The apparatus further includes a mixing zone fluidly connected to the at least two intersecting channels for mixing the sequencing reagents, and a size separation zone fluidly connected to the mixing zone for separating sequencing products by size, thereby providing the sequence of a target nucleic acid. Optionally, the apparatus has a sequence detector for reading the sequence of the target nucleic acid. In one preferred embodiment, the apparatus has a set of wells for receiving reagents such as primer sets for use in the apparatus. In one embodiment, the apparatus has at least 4,096 wells fluidly connected to the at least two intersecting channels. Alternatively, the apparatus can include a substrate (matrix, or membrane) with primers located on the substrate. Often, the primers will be dried in spots on the substrate. In this embodiment, the apparatus will typically include an electropipettor which has a tip designed to re-hydrate a selected spot corresponding to a dried primer, and for electrophoretic transport of the rehydrated primer to an analysis region in the microfluidic device (i.e., a component of the microfluidic device which includes a reaction channel). Thus, in a preferred embodiment, the device will include a substrate such as a membrane having, e.g., 4,096 spots (i.e., all possible 6-mer primers). Similarly, components in diagnostic or drug screening assays can be stored in the well or membrane format for introduction into the analysis region of the device. Arrays of nucleic acids, proteins and other compounds are also used in a similar manner.

In another embodiment, the invention provides systems for determining a sequence of nucleotides in a target nucleic acid sequence. The system includes a microfluidic device having a body structure with at least a first mixing or analysis channel, and at least a first probe introduction channel disposed therein, the analysis channel intersecting and being in fluid communication with the probe introduction channel. The system includes a source of the target nucleic acid sequence in fluid communication with the analysis channel and a plurality of separate sources of oligonucleotide probes in fluid communication with the probe introduction channel, each of the plurality of separate sources containing an oligonucleotide probe having a different nucleotide sequence of length n. Typically, all or essentially all (i.e., most, i.e., at least about 70%, typically 90% or more) of the possible oligonucleotides of a given length are included, although a subset of all possible oligonucleotides can also be used. The system also includes a sampling system for separately transporting a volume of each of the oligonucleotide probes from the sources of oligonucleotide probes to the probe introduction channel and injecting each of the oligonucleotide probes into the analysis channel to contact the target nucleic acid sequence and a detection system for identifying whether each oligonucleotide probe hybridizes with the target nucleic acid sequence.

Methods of using the system for sequencing by hybridization to perfectly matched probes are also provided. In these methods, a target nucleic acid is flowed into the analysis channel and a plurality of extension probes are separately injected into the analysis channel, whereupon the extension probes contact the target nucleic acid sequence. In the method, a first subsequence of nucleotides in the target nucleic acid is typically known, and each of the plurality of extension probes has a first sequence portion that is perfectly complementary to at least a portion of the first subsequence, and an extension portion that corresponds to a portion of the target nucleic acid sequence adjacent to the target subsequence, the extension portion having a length n, and comprising all possible nucleotide sequences of length n, wherein n is between 1 and 4 inclusive. A sequence of nucleotides is identified adjacent the target subsequence, based upon which of the plurality of extension probes perfectly hybridizes with the target nucleic acid sequence.

DEFINITIONS

Figure 1:
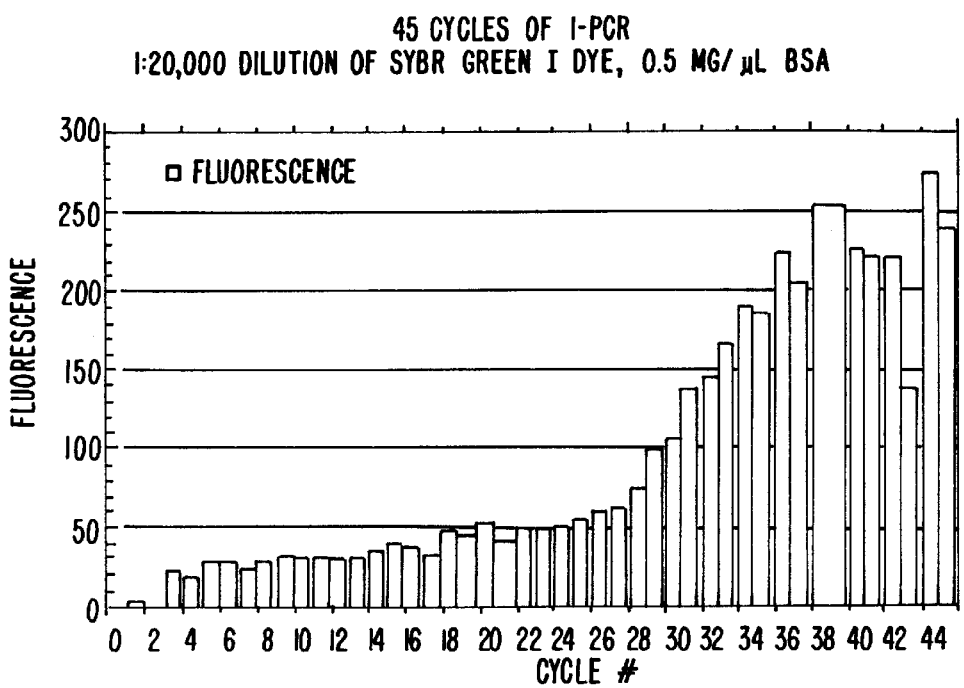
FIG. 1 depicts a graph of florescence signal of intercalating dye for lambda genomic DNA.

An "integrated microfluidic system" is a microfluidic system in which a plurality of fluidic operations are performed. In one embodiment, the results of a first reaction in the microfluidic system are used to select reactants or other reagents for a second reaction or assay. The system will typically include a microfluidic substrate, and a fluidic interface for sampling reactants or other components. A detector and a computer are often included for detecting reaction products and for recording, selecting, facilitating and monitoring reactions in the microfluidic substrate.

A "microfluidic device" is an apparatus or component of an apparatus having microfluidic reaction channels and/or chambers. Typically, at least one reaction channel or chamber will have at least one cross-sectional dimension between about 0.1 $\mu$m and about 500 $\mu$m.

A "reaction channel" is a channel (in any form, including a closed channel, a capillary, a trench, groove or the like) on or in a microfluidic substrate (a chip, bed, wafer, laminate, or the like having microfluidic channels) in which two or more components are mixed. The channel will have at least one region with a cross sectional dimension of between about 0.1 $\mu$m and about 500 $\mu$m.

A "reagent channel" is a channel (in any form, including a closed channel, a capillary, a trench, groove or the like) on or in a microfluidic substrate (a chip, bed, wafer, laminate, or the like having microfluidic channels) through which components are transported (typically suspended or dissolved in a fluid). The channel will have at least one region with a cross sectional dimension of between about 0.1 $\mu$m and about 500 $\mu$m.

A "material transport system" is a system for moving components along or through microfluidic channels. Exemplar transport systems include electrokinetic, electroosmotic, and electrophoretic systems (e.g., electrodes in fluidly connected wells having a coupled current and/or voltage controller), as well as micro-pump and valve systems.

A "fluidic interface" in the context of a microfluidic substrate is a component for transporting materials into or out of the substrate. The interface can include, e.g., an electropipettor, capillaries, channels, pins, pipettors, sippers, or the like for moving fluids into the microfluidic substrate.

The overall function, i.e., intended goal, of the devices, systems and methods of the invention are generally referred to as "fluidic operations." For example, where a device's intended function is to screen a sample against a panel of antigens, the entire screen is referred to as a single fluidic operation. Similarly, the fluidic operation of a device intended to amplify nucleic acids is the completion of the amplification process, including all of the numerous melting, annealing extension cycles. However, the individual steps of the overall fluidic operation are generally referred to as a "fluid manipulation." In the screening example, the combination or mixture of a portion of the sample with a solution containing a single antigen would constitute a fluid manipulation. Similarly, in the amplification example, each separate reagent addition step required for each separate cycling step would constitute a single fluid manipulation. In many cases, the fluids utilized in the microfluidic devices and methods of the invention are referred to as reactants to denote their ability to undergo a chemical reaction, either alone, or when combined with another reactive fluid or composition. It will be readily apparent that the phrases "fluidic operation" and "fluid manipulation" encompass a wide variety of such manipulations for carrying out a variety of chemical, biological and biochemical reactions, either entirely fluid based or incorporating a non-fluid element, e.g., cells, solid supports, catalysts, etc., including, reagent additions, combinations, extractions, filtrations, purifications, and the like.

A "sequencing primer" is an oligonucleotide primer which is can be extended with a polymerase in the presence of a template and appropriate reagents (dNTPs, etc).

DETAILED DESCRIPTION

High throughput manipulation and analysis of fluidic reagents is desirable for a variety of applications, including nucleic acid sequencing, screening of chemical or biological libraries, purification of molecules of interest, amplification of nucleic acids and the like. The present invention provides apparatus, systems and methods for dramatically increasing the speed and simplicity of screening, manipulating and assessing fluidic reagents, reagent mixtures, reaction products (including the products of DNA sequencing reactions) and the like. The invention provides integrated systems for performing a variety of chemical, biochemical and biological experiments and other fluidic operations, including PCR, DNA sequencing, integrated or sequential screening of chemical or biological libraries, and the like. Although the microfluidic systems of the invention are generally described in terms of the performance of chemical, biochemical or biological reactions separations, incubations and the like, it will be understood that, as fluidic systems having general applicability, these systems can have a wide variety of different uses, e.g., as metering or dispensing systems in both biological and nonbiological applications.

In the methods of the prior art, most fluidic operations are generally performable at the bench scale, e.g., involving reagent volumes ranging from 10 $\mu$l to 1 or more liters. However, the performance of large numbers of iterative, successive or parallel fluid manipulations at the bench scale potentially includes a number of associated problems. For example, when performed manually, repetitive tasks, e.g., fluid measurement and addition, are often plagued by errors and mistakes, which often result in the overall failure of the overall operation. Similarly, iterative or successive processing of small fluid samples often results in substantial yield problems, e.g., from loss of material during incomplete fluid transfers, i.e., resulting from incomplete transfer of fluid volumes, adsorption of materials on reaction vessels, pipettes and the like. These problems can substantially reduce the accuracy and reproducibility of a particular process performed manually, or at the bench scale. Further, in fluidic operations that employ large numbers of parallel fluid manipulations, while the individual separate reactions are not overly cumbersome, the logistics of coordinating and carrying out each of the parallel manipulations can become unmanageable. Additionally, the costs, complexity and space requirements of equipment for facilitating these operations, e.g., robotics, creates further difficulties in performing these types of operations.

In addition to the above, where reagent costs are substantial, even at the low end of the volume spectrum, a particular fluidic operation involving numerous iterative or parallel reagent additions, can be commercially impracticable from a cost standpoint. Further, as reagent volumes become smaller and smaller, errors in measurement become more and more problematic. By performing iterative, successive or parallel fluid manipulations in microfluidic devices that are partially sealed and automatable, the above-described problems of measurement and fluid transfer errors, reagent costs, equipment costs and space requirements are alleviated.

Accordingly, in one aspect, the present invention provides microfluidic devices, systems and methods that are particularly useful in performing fluid operations that require a large number of iterative fluid manipulations. By "iterative fluid manipulations" is meant the movement and/or direction, incubation/reaction, separation or detection of discrete volumes of fluid, typically in a serial format or orientation, in a repetitive fashion, i.e., performing the same type of manipulation on multiple separate samples, diluting a particular sample, etc., typically while varying one or more parameter in each series of reactions. When performed at bench scales, iterative fluid manipulations become relatively cumbersome as the number of repetitions becomes greater, resulting in a substantial increase in the likelihood of errors in measurement or the like, and requiring massive labor inputs as a user has to select which parameters or reagents to vary in each successive operation. As such, the systems and devices of the present invention are particularly useful in performing such iterative fluid manipulations, e.g., which require performance of a particular fluid manipulation greater than about 10 times, typically greater than about 20 times, preferably greater than about 50 times and often greater than about 100 times. In particularly preferred aspects, such fluid manipulations are repeated between about 10 and 100 times or between about 100 and 1000 times.

The present invention, therefore, provides microfluidic systems and methods that are useful for performing a wide variety of different fluidic operations, i.e., chemical, biochemical or biological reactions, incubations, separations, and the like, which, when performed by previously known methods, would be difficult or cumbersome, either in terms of time, space, labor and/or costs. In particular, the systems of the present invention permit the performance of a wide variety of fluidic operations without requiring large amounts of space, expensive reagents and/or equipment, or excessive time and labor costs. Specifically, as microfluidic devices are employed, the methods and systems of the invention utilize less space and have smaller reagent requirements. In addition, because these microfluidic systems are automatable and partially sealed, they can reduce the amount of human involvement in these manipulations, saving labor and eliminating many of the areas that are prone to human error, e.g., contamination, measurement errors, loss of materials and the like. A powerful new additional aspect of the present invention is the ability of the apparatus, systems and methods to select components of iterative assays based upon the results of previous assays.

In its simplest embodiment, iterative fluid manipulation includes the repeated movement, direction or delivery of a discrete volume of a particular reagent to or through a particular reaction chamber or channel. In more complex embodiments, such iterative fluid manipulations include the apportioning of larger fluid volumes into smaller, discrete fluid volumes, which includes the aliquoting of a given sample among a number of separate reaction chambers or channels, or the taking of aliquots from numerous discrete fluids, e.g., samples, to deliver these aliquots to the same or different reaction chambers or channels.

In another, similar aspect, the devices, systems and methods of the invention are useful in performing fluidic operations that require a large number of successive fluid manipulations, i.e., in performing a number of preparative and analytical reactions or operations on a given sample. By "successive fluid manipulations" is generally meant a fluidic operation that involves the successive treatment of a given fluid sample volume, i.e., combination/reaction with reactants, incubation, purification/separation, analysis of products, and the like. Where successive fluid manipulations are performed at the bench scale, e.g., the performance of numerous, different manipulations on a particular sample such as combination with reagents, incubation, separation and detection, such manipulations can also become cumbersome as the number of steps increases, as with each step, the possibility of introducing an error into the operation or experiment increases. This complexity, and the consequent increased possibility of errors increases substantially as the number of samples to be passed through the operation increases. Thus, the devices or systems of the present invention are also particularly useful in performing fluidic operations which require successive fluid manipulations of a given sample or fluid of interest, e.g., more than 2 steps or different manipulations, typically greater than 5 steps or different manipulations, preferably greater than 10 steps or different fluid manipulations. The systems are also useful and readily capable of performing fluidic operations that include greater than 20, 50, 100, 1000 steps or different fluid manipulations on a given fluid volume.

In a related, but alternate aspect, the devices, systems and methods of the invention are useful in performing fluidic operations that require a large number of parallel fluid manipulations, i.e., to screen biological samples, screen test compounds for drug discovery, e.g., as set forth in U.S. Pat. Nos. 5,942,443 and 5,779,868 both incorporated herein by reference. To carry out these operations, a substrate will typically employ an array of parallel channels and/or channel networks, interconnected by one or more common channels. Fluids required for the subject reaction, e.g., samples or reagents, are directed along one or more of the common channels, and are delivered to each of the parallel channels.

As used herein, "parallel fluid manipulations" means the substantially concurrent movement and/or direction, incubation/reaction, separation or detection of discrete fluid volumes to a plurality of parallel channels and/or channel networks, or chambers of a microfluidic device, i.e., greater than about 10 distinct parallel channels or chambers, typically greater than 20 distinct channels or chambers, preferably greater than about 50 distinct channels or chambers, and often greater than about 100 distinct channels or chambers. As used herein, the term "parallel" refers to the ability to concomitantly or substantially concurrently process two or more separate fluid volumes, and does not necessarily denote a specific channel or chamber structure or layout.

Ultra high-throughput analysis systems are provided, for example for performing nucleic acids-based diagnostic and sequencing applications, e.g., in a reference laboratory setting. The system typically has several components: a specimen and reagents handling system; an "operating system" for processing integrated microchip experimentation steps; application-specific analysis devices (optionally referred in this application e.g., as "LabChips™" (LabChip™ is a trademark of Caliper Technologies, Corp., Palo Alto Calf.); a fluorescence-based signal detection system, and multiple software components that allow the user to interact with the system, and run processing steps, interpret data, and report results.

Application to Sequencing Projects

In a preferred aspect, the invention provides a closed loop device for determining the entire sequence of an unknown DNA molecule of interest by iteratively sequencing sub regions of the molecule of interest. In one aspect, oligonucleotides are chosen from a pool of possible sequencing primers upon determination of an initial portion of the DNA sequence. With iterative utilization of this strategy, it is possible to walk through an entire sequence without synthesizing new primers.

"Primer walking" is a standard strategy for determining the sequence of an unknown DNA. For example, a portion of an unsequenced DNA cloned into a plasmid can be sequenced using a primer complementary to a portion of the plasmid, and extending the sequencing reaction into the unknown region of the DNA with a template dependent polymerase. However, standard electrophoretic analysis of the sequencing reaction only allows resolution of a few hundred nucleotides. Once the sequence of a few hundred nucleotides is determined, a second primer is synthesized to be complementary to a portion of the sequenced region, and the reaction is repeated, giving a new sequence which yields an additional few hundred nucleotides. Although the process is conceptually simple, it is also very labor intensive and time consuming for large nucleotide sequences. For example, sequencing a Yeast Artificial Chromosome (YAC) clone of a modest 100,000 bases using this serial primer walking fashion would require at least about 300–1,000 individual reactions, with a corresponding number of primer syntheses. It should also be noted that each of these primer syntheses typically produces thousands of times as much primer as needed for the particular sequencing reaction, dramatically increasing the cost of sequencing.

The present invention simplifies the standard primer walking strategy by modifying, automating and integrating each part of primer walking into a single integrated system. In the methods of the invention, all of the mixing and analysis steps are performed with an integrated system, and all primer synthetic steps are preferably avoided. In brief, a template nucleic acid is selected and introduced into a reaction channel in a microfluidic (generally electroosmotic) device of the invention. The template is optionally amplified, e.g., by introducing PCR or LCR reagents into the channel and performing cycles of heating and cooling on the template. Alternatively, e.g., where the source of template is from an abundant sequence such as a cloned nucleic acid, further amplification can be unnecessary. In addition to amplification procedures, a PCR nuclease chain termination procedure can also be used for direct sequencing in the methods of the invention. Porter et al. (1997) *Nucleic Acids Research* 25(8):1611–1617 describe the biochemistry of PCR chain termination methods.

Sequencing reagents are added to the template nucleic acid and a sequencing reaction is performed appropriate to the particular reaction in use. Many appropriate reactions are known, with the Sanger dideoxy chain termination method being the most common. See, Sanger et al. (1977) *Proc. Nat. Acad. Sci., USA* 74:5463–5467. The primer used to prime synthesis is typically selected from a pre-synthesized set of nucleic acid primers, preferably a set including many or all of the primers for a particular primer length. In a preferred aspect, modular primers are used.

After the sequencing reaction is run, the products are separated by size and/or charge in an analysis region of the microfluidic device. As discussed herein, the devices of the invention can be used to electrophoretically separate macromolecules by size and/or charge. The separated products are detected, often as they pass a detector (nucleic acids are typically labeled with radioactive nucleotides or fluorophores; accordingly appropriate detectors include spectrophotometers, fluorescent detectors, microscopes (e.g., for fluorescent microscopy) and scintillation counting devices). Detection of the size separated products is used to compile sequence information for the region being sequenced. A computer is used to select a second primer from the pre-synthesized primer set which hybridizes to the sequenced region, and the process is iteratively repeated with the second primer, leading to sequencing of a second region, selection of a third primer hybridizing to the second region, etc.

Providing DNA Templates for Sequencing

The integrated systems of the invention are useful for sequencing a wide variety of nucleic acid constructs. Essentially any DNA template can be sequenced, with the selection of the nucleic acid to be sequenced depending upon the construct in hand by the sequencer. Thus, an initial step in the methods of the invention is the selection or production of a template nucleic acid to be sequenced.

Many methods of making recombinant ribo and deoxyribo nucleic acids, including recombinant plasmids, recombinant lambda phage, cosmids, yeast artificial chromosomes (YACs), P1 artificial chromosomes, Bacterial Artificial Chromosomes (BACs), and the like are known. The sequencing of large nucleic acid templates is advantageously performed by the present methods, systems and apparatus, because an entire nucleic acid can be sequenced by primer walking along the length of the template in several rapid cycles of sequencing.

Cloning Templates or Other Targets for Use in the Methods, Apparatus and Systems of the Invention Examples of appropriate cloning techniques for making nucleic acids, and instructions sufficient to direct persons of skill through most standard cloning and other template preparation exercises are found in Berger and Kimmel, *Guide to Molecular Cloning Techniques, Methods in Enzymology* volume 152 Academic Press, Inc., San Diego, Calf. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1997, supplement 37) (Ausubel). Basic procedures for cloning and other aspects of molecular biology and underlying theoretical considerations are also found in Lewin (1995) Genes V Oxford University Press Inc., NY (Lewin); and Watson et al. (1992) *Recombinant DNA Second Edition* Scientific American Books, NY. Product information from manufacturers of biological reagents and experimental equipment also provide information useful in known biological methods. Such manufacturers include the Sigma Chemical Company (Saint Louis, Mo.); New England Biolabs (Beverly, Mass.); R&D systems (Minneapolis, Minn.); Pharmacia LKB Biotechnology (Piscataway, N.J.); CLONTECH Laboratories, Inc. (Palo Alto, Calf.); Chem-Genes Corp., (Waltham Mass.) Aldrich Chemical Company (Milwaukee, Wiss.); Glen Research, Inc. (Sterling, Va.); GIBCO BRL Life Technologies, Inc. (Gaithersberg, Md.); Fluka Chemica-Biochemika Analytika (Fluka Chemie A G, Buchs, Switzerland); Invitrogen (San Diego, Calf.); Perkin Elmer (Foster City, Calf.); and Strategene; as well as many other commercial sources known to one of skill.

In one aspect, the generation of large nucleic acids is useful in practicing the invention. It will be appreciated that such templates are particularly useful in some aspects where the methods and devices of the invention are used to sequence large regions of DNA, e.g., for genomics types of applications. An introduction to large clones such as YACs, BACs, PACs and MACs as artificial chromosomes is provided by Monaco and Larin (1994) *Trends Biotechnol* 12 (7): 280–286.

The construction of nucleic acid libraries of template nucleic acids is described in the above references. YACs and YAC libraries are further described in Burke et al. (1987) *Science* 236:806–812. Gridded libraries of YACs are described in Anand et al. (1989) *Nucleic Acids Res.* 17, 3425–3433, and Anand et al. (1990) *Nucleic Acids Res.* Riley (1990) 18:1951–1956 *Nucleic Acids Res.* 18(10): 2887–2890 and the references therein describe cloning of YACs and the use of vectorettes in conjunction with YACs. See also, Ausubel, chapter 13. Cosmid cloning is also well known. See, e.g., Ausubel, chapter 1.10.11 (supplement 13) and the references therein. See also, Ish-Horowitz and Burke (1981) *Nucleic Acids Res.* 9:2989–2998; Murray (1983) Phage Lambda and Molecular Cloning in *Lambda II* (Hendrix et al., eds) 395–432 Cold Spring Harbor Laboratory, NY; Frischauf et al. (1983) *J.Mol. Biol.* 170:827–842; and, Dunn and Blattner (1987) *Nucleic Acids Res.* 15:2677–2698, and the references cited therein. Construction of BAC and P1 libraries is well known; see, e.g., Ashworth et al. (1995) *Anal Biochem* 224 (2): 564–571; Wang et al. (1994) *Genomics* 24(3): 527–534; Kim et al. (1994) *Genomics* 22(2): 336–9; Rouquier et al. (1994) *Anal Biochem* 217(2): 205–9; Shizuya et al. (1992) *Proc Natl Acad Sci USA* 89(18): 8794–7; Kim et al. (1994) *Genomics* 22 (2): 336–9; Woo et al. (1994) *Nucleic Acids Res* 22(23): 4922–31; Wang et al. (1995) *Plant* (3): 525–33; Cai (1995) *Genomics* 29 (2): 413–25; Schmitt et al. (1996) *Genomics* 1996 33(1): 9–20; Kim et al. (1996) *Genomics* 34(2): 213–8; Kim et al. (1996) *Proc Natl Acad Sci USA* (13): 6297–301; Pusch et al. (1996) *Gene* 183(1–2): 29–33; and, Wang et al. (1996) *Genome Res* 6(7): 612–9. In general, where the desired goal of a sequencing project is the sequencing of a genome or expression profile of an organism, a library of the organism's cDNA or genomic DNA is made according to standard procedures described, e.g., in the references above. Individual clones are isolated and sequenced, and overlapping sequence information is ordered to provide the sequence of the organism. See also, Tomb et al. (1997) *Nature* 539–547 describing the whole genome random sequencing and assembly of the complete genomic sequence of *Helicobacter pylori;* Fleischmann et al. (1995) *Science* 269:496–512 describing whole genome random sequencing and assembly of the complete *Haemophilus influenzae* genome; Fraser et al. (1995) *Science* 270:397–403 describing whole genome random sequencing and assembly of the complete *Mycoplasma genitalium* genome and Bult et al. (1996) *Science* 273:1058–1073 describing whole genome random sequencing and assembly of the complete *Methanococcus jannaschii* genome.

The nucleic acids sequenced by this invention, whether RNA, cDNA, genomic DNA, or a hybrid of the various combinations, are isolated from biological sources or synthesized in vitro. The nucleic acids of the invention are present in transformed or transfected whole cells, in transformed or transfected cell lysates, or in a partially purified or substantially pure form.

Amplification in Microscale Devices—PCR

Bench scale in vitro amplification techniques suitable for amplifying sequences to provide a nucleic acid e.g., as a diagnostic indicator for the presence of the sequence, or for subsequent analysis, sequencing or subcloning are known.

In brief, the most common form of in vitro amplification, i.e., PCR amplification, generally involves the use of one strand of the target nucleic acid sequence as a template for producing a large number of complements to that sequence. As used herein, the phrase "target nucleic acid sequence" generally refers to a nucleic acid sequence, or portion of a nucleic acid sequence that is the subject of a particular fluidic operation, e.g., analysis, amplification, identification or the like. Generally, two primer sequences complementary to different ends of a segment of the complementary strands of the target sequence hybridize with their respective strands of the target sequence, and in the presence of polymerase enzymes and nucleoside triphosphates, the primers are extended along the target sequence through the action of the polymerase enzyme. The extensions are melted from the target sequence by raising the temperature of the reaction mixture, and the process is repeated, this time with the additional copies of the target sequence synthesized in the preceding steps. PCR amplification typically involves repeated cycles of denaturation, hybridization and extension reactions to produce sufficient amounts of the target nucleic acid, all of which are carried out at different temperatures. Typically, melting of the strands, or heat denaturation, involves temperatures ranging from about 90° C. to 100° C. for times ranging from seconds to minutes. The temperature is then cycled down, e.g., to between about 40° C. and 65° C. for annealing, and then cycled up to between about 70° C. and 85° C. for extension of the primers along the target strand.

Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calf. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426, 039. Improved methods of amplifying large nucleic acids by PCR are summarized in Cheng et al. (1994) *Nature* 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

It will be appreciated that these benchtop uses for PCR are adaptable to microfluidic systems. Indeed, PCR amplification is particularly well suited to use in the apparatus, methods and systems of the invention.

Thermocycling amplification methods, including PCR and LCR, are conveniently performed in microscale devices, making iterative fluidic operations involving PCR well suited to use in methods and devices of the present invention (see also, U.S. Pat. Nos. 5,498,392 and 5,587,128 to Willingham et al.). Accordingly, in one preferred embodiment, generation of amplicons such as sequencing templates using PCR, or direct sequencing of nucleic acids by PCR (e.g., using nuclease digestion as described supra) is performed with the integrated systems and devices of the invention.

Thermocycling in microscale devices is described in co-pending application U.S. Ser. No. 60/056,058, attorney docket number 017646-003800 entitled "ELECTRICAL CURRENT FOR CONTROLLING FLUID TEMPERATURES IN MICROCHANNELS" filed Sep. 2, 1997 by Calvin Chow, Anne R. Kopf-Sill and J. Wallace Parce and in U.S. Pat. No. 5,965,410. In brief, energy is provided to heat fluids, e.g., samples, analytes, buffers and reagents, in desired locations of the substrates in an efficient manner by application of electric current to fluids in microchannels. Thus, the present invention optionally uses power sources that pass electrical current through the fluid in a channel for heating purposes, as well as for material transport. In exemplary embodiments, the fluid passes through a channel of a desired cross-section (e.g., diameter) to enhance thermal transfer of energy from the current to the fluid. The channels can be formed on almost any type of substrate material such as, for example, amorphous materials (e.g., glass, plastic, silicon), composites, multi-layered materials, combinations thereof, and the like.

In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance:

POWER=$I^2R$ where

POWER=power dissipated in fluid;

I=electric current passing through fluid; and

R=electric resistance of fluid.

The above equation provides a relationship between power dissipated ("POWER") to current ("I") and resistance ("R"). In some of the embodiments, which are directed toward moving fluid in channels, e.g., to provide mixing, electrophoretic separation, or the like, a portion of the power goes into kinetic energy of moving the fluid through the channel. However, it is also possible to use a selected portion of the power to controllably heat fluid in a channel or selected channel regions. A channel region suitable for heating is often narrower or smaller in cross-section than other channel regions in the channel structure, as a smaller cross-section provides higher resistance in the fluid, which increases the temperature of the fluid as electric current passes through. Alternatively, the electric current is increased across the length of the channel by increased voltage, which also increases the amount of power dissipated into the fluid to correspondingly increase fluid temperature.

To selectively control the temperature of fluid at a region of the channel, a power supply applies voltage and/or current in one of many ways. For instance, a power supply can apply direct current (i.e., DC) or alternating current (AC), which passes through the channel and into a channel region which is smaller in cross-section, thereby heating fluid in the region. This current is selectively adjusted in magnitude to complement any voltage or electric field that is applied to move fluid in and out of the region. AC current, voltage, and/or frequency can be adjusted, for example, to heat the fluid without substantially moving the fluid. Alternatively, a power supply can apply a pulse or impulse of current and/or voltage, which passes through the channel and into a channel region to heat fluid in the region. This pulse is selectively adjusted to complement any voltage or electric field that is applied to move fluid in and out of the region. Pulse width, shape, and/or intensity can be adjusted, for example, to heat the fluid substantially without moving the fluid or to heat the fluid while moving the fluid. Still further, the power supply can apply any combination of DC, AC, and pulse, depending upon the application. In practice, direct application of electric current to fluids in the microchannels of the invention results in extremely rapid and easily controlled changes in temperature.

A controller or computer such as a personal computer monitors the temperature of the fluid in the region of the channel where the fluid is heated. The controller or computer receives current and voltage information from, for example, the power supply and identifies or detects temperature of fluid in the region of the channel. Depending upon the desired temperature of fluid in the region, the controller or computer adjusts voltage and/or current to meet the desired fluid temperature. The controller or computer also can be set to be "current controlled" or "voltage controlled" or "power controlled" depending upon the application.

The region which is heated can be a "coil" which is optionally in a planar arrangement. Transfer of heat from the coil to a reaction channel through a substrate material is used to heat the reaction channel. Alternatively, the coil itself is optionally the reaction channel.

A voltage is applied between regions of the coil to direct current through the fluid for heating purposes. In particular, a power supply provides a voltage differential between regions of the coil. Current flows between the regions and traverses a plurality of coils or coil loops (which can be planar), which are defined by a substrate. Shape and size of the coils can influence an ability of current to heat the fluid in the coil. As current traverses through the fluid, energy is transferred to the fluid for heating purposes. Cooling coils can also be used. As a cooling coil, a fluid traverses from region to region in the coil, which can be placed to permit heat transfer through a substrate from a sample. The cooling fluid can be a variety of substances including liquids and gases. As merely an example, the cooling fluid includes aqueous solutions, liquid or gaseous nitrogen, and others. The cooling fluid can be moved between regions using any of the techniques described herein, and others. Further details are found in Chow et al., supra.

The introduction of electrical current into fluid causes heat (Joule heating). In the examples of fluid movement herein where thermal effects are not desired, the heating effect is minimal because, at the small currents employed, heat is rapidly dissipated into the chip itself. By substantially increasing the current across the channel, rapid temperature changes are induced that can be monitored by conductivity. At the same time, the fluid can be kept static in the channel by using alternating instead of direct current. Because nanoliter volumes of fluid have tiny thermal mass, transitions between temperatures can be extremely short. Oscillations between any two temperatures above 0° C. and below 100° C. in 100 milliseconds have been performed.

Joule heating in microchannels is an example of how a key component of a conventional genomics methods can be dramatically improved in the formats provided herein. PCR takes hours to perform currently, primarily because it takes a long time for conventional heating blocks to oscillate between temperatures. In addition, reagent cost is an obstacle to massive experimentation. Both these parameters are altered by orders of magnitude in the LabChip format. FIG. 1 shows amplification of bacteriophage lambda DNA in a 10 nanoliter volume. It should be noted that the optical interrogation volume was 400 picoliters. At a template concentration of 10 ng/ml, the signal seen starting at the 27th cycle came from the amplification of approximately 80 target molecules. The transition between 68° C. and 94° C. took place in less than 1 second.

Figure 2:
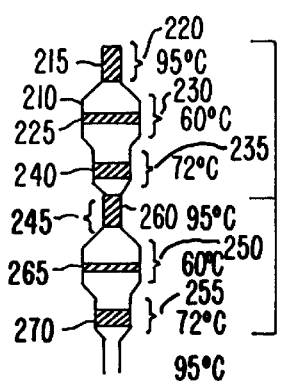
FIG. 2 depicts a thermocycler channel with varying widths for performing, e.g., PCR.

In one aspect, PCR reaction conditions are controlled as a function of channel geometry. Microfabrication methods permit the manufacture of channels that have precise variations in cross sectional area. Since the channel resistance is inversely proportional to the cross sectional area, the temperature varies with the width and depth of the channel for a given flow of current. As fluid moves through a structure of varying cross sectional area, its temperature will change, depending on the dimensions of the channel at any given point. The amount of time it experiences a given temperature will be determined by the velocity of the fluid flow, and the length of channel with those dimensions. This concept is illustrated in FIG. 2. Nucleic acids of typical lengths have a low diffusion coefficient (about $10^{-7}$ cm/sec$^2$). Thus over the time frame necessary to affect amplification, DNA will only diffuse a few hundred microns. In a given channel, reactions of a few nanoliters will occupy a few millimeters. Thus in devices of convenient length (a few centimeters), many PCR reactions can be performed concurrently yielding new amplification products every few seconds per channel. In parallel formats, hundreds of separate reactions can be performed simultaneously. Because of its simplicity, throughput and convenience, this amplification unit is a preferred feature of many assays herein.

In FIG. 2, amplification reactions are performed concurrently in series using biased alternating current to heat the fluid inside the channel and move material through it. The time for each step of the reaction is controlled by determining the speed of movement and the length of channel having particular widths. Flow can be reversed to allow a single small channel region to be used for many separate amplifications.

As depicted, several samples are run simultaneously in channel 210. Sample 215 is in narrow channel region 220; in operation, this region is heated to, e.g., 95° C. (hot enough to denature nucleic acids present in sample 215, but cool enough that thermostable reagents such as Taq DNA polymerase are relatively stable due to the relative size of region 220 and the applied current. Concurrently, wide channel region 230 is heated, e.g., to 60° C. (cool enough for binding of primers in sample 225 and initiation of polymerase extension), due to the relative size of region 230 and the applied current. Concurrently, intermediate channel region 235 is heated, e.g., to 72° C. (hot enough to prevent unwanted non-specific primer-target nucleic acid interactions in sample 240 and cool enough to permit continued polymerase extension), due to the relative size of region 235 and the applied current. This process can be concurrently carried out with a plurality of additional channel regions such as narrow region 245, wide region 250 and intermediate region 255, with samples 260, 265 and 270.

Where possible, direct detection of amplified products can be employed. For example, differentially labeled competitive probe hybridization is used for single nucleotide discrimination. Alternatively, molecular beacons or single nucleotide polymerase extension can be employed. Homogeneous detection by fluorescence polarization spectroscopy can also be utilized (fluorescence polarization has been used to distinguish between labeled small molecules free in solution or bound to protein receptors).

If the analysis requires post-PCR processing, a more complex channel and control structure is used as in the case where the amplified product is to be typed at a microsatellite locus. Because single nucleotide separations take time (approximately 5 minutes today), the output of the serial amplification unit is optionally analyzed in parallel separations channels following serial to parallel fluidic manipulation as described herein.

Where possible, direct detection of amplified products can be employed. For example, differentially labeled competitive probe hybridization is used for single nucleotide discrimination. Alternatively, molecular beacons or single nucleotide polymerase extension can be employed. Homogeneous detection by fluorescence polarization spectroscopy can also be utilized (fluorescence polarization has been used to distinguish between labeled small molecules free in solution or bound to protein receptors).

Amplification in Microscal Devices—Non-Thermal Methods

Another example of a fluidic operation requiring multiple iterative fluid manipulations which was previously impracticable for cost reasons, is non-thermal amplification of nucleic acids. In non-thermal amplification, strand separation is optionally carried out by chemical means. Thus, by "non-thermal amplification" is meant the amplification of nucleic acids without thermal cycling of the reaction mixture to affect the melting and annealing of the nucleic acid strands. In practice, such methods involve the chemical denaturation of nucleic acid strands, followed by dilution or neutralization of the chemical denaturant. For example, in one aspect, strand separation is carried out by raising the pH of the reaction mixture to denature the nucleic acid strands. The pH is then returned to neutral, for annealing and extension. Other chemical denaturants are equally useful to affect strand separation. For example, chaotropic agents, e.g., urea, formamide, and the like, are employed in place of base.

Regardless of the chemical denaturant, however, addition of these materials will typically result in the denaturing of the enzymes present in the reaction mixture, e.g., polymerases, in addition to the nucleic acids, and thereby lead to their inactivation. As such, performance of this type of amplification at the bench scale, would require large amounts of expensive enzymes. Further, the additional volume required for adding these enzymes, as well as diluting or neutralizing the denaturants, would result in cumbersome manipulations, particularly where a large number of cycles is performed.

In the systems, devices and methods of the present invention, non-thermal amplification can be carried out by introducing a sample or target nucleic acid into a reaction chamber, channel or zone of a microfluidic device. The complementary strands of the target nucleic acid are melted apart by introducing a preselected volume of a chemical denaturant, which denatures the complementary strands of the nucleic acid. In particularly preferred aspects, denaturation is accomplished by raising the pH of the reaction mixture to approximately 10–13. This is readily accomplished by introducing an equal volume of dilute NaOH, e.g., approximately 0.2N NaOH).

Annealing of the primers to the target strand is carried out by removing the denaturing effects of the denaturant. For example, in those aspects where a dilute base is used to denature the nucleic acid, the base is optionally neutralized by the addition of a similar volume of dilute acid, e.g., 0.2N HCl. Where chaotropic agents are used, the denaturing effect can generally be removed by desalting the reaction mixture or the like. A preselected volume containing an effective amount of polymerase enzyme and primer sequences are then added to the reaction mixture, i.e., sufficient to amplify the target sequence. Because volumes of reagents are so small in the devices and methods of the invention, the polymerase need not be thermally or otherwise stable to the more extreme conditions of the amplification reaction as in PCR. Specifically, denaturation of the nucleic acids will typically result in denaturation of the polymerase enzyme, as well. However, additional amounts of enzyme can be added back to the amplification mixture. Because small volumes are used, the costs are maintained relatively low. As a result of this, any number of a variety of common polymerase enzymes can be used, including *E. coli* DNA polymerases, e.g., *E. coli* DNA pol I, Klenow fragment, T7 DNA polymerase or the like. Further, one could operate the system at an elevated temperature and utilize thermally stable Taq polymerases, Pfu DNA polymerase, Bst and Vent, all of which are commercially available.

The primers anneal to the target nucleic acid and begin the extension process. Denaturation, annealing and extension steps are then repeated the desired number of times to sufficiently amplify the target nucleic acid. Typically, these cycles are repeated from about 10 to about 100 times, and preferably between about 10 and 50 times.

A number of modifications are readily made to this amplification process. For example, one can introduce primer sequences into the reaction mixture at the outset, or along with the polymerase enzymes, as indicated. Similarly, following denaturation, it can be desirable to desalt the amplification reaction mixture, e.g., by passing the mixture through a chromatographic matrix incorporated into the device or by separating the desired elements of the reaction mixture by electrophoresing the mixture in an appropriate medium. Such desalting can be particularly useful where other chemical denaturants are used, e.g., urea, etc. In such cases, the denaturing effects of these chemicals are typically removed by dilution or removal of the denaturant from the amplification reaction mixture, i.e., by desalting.

Figure 3:
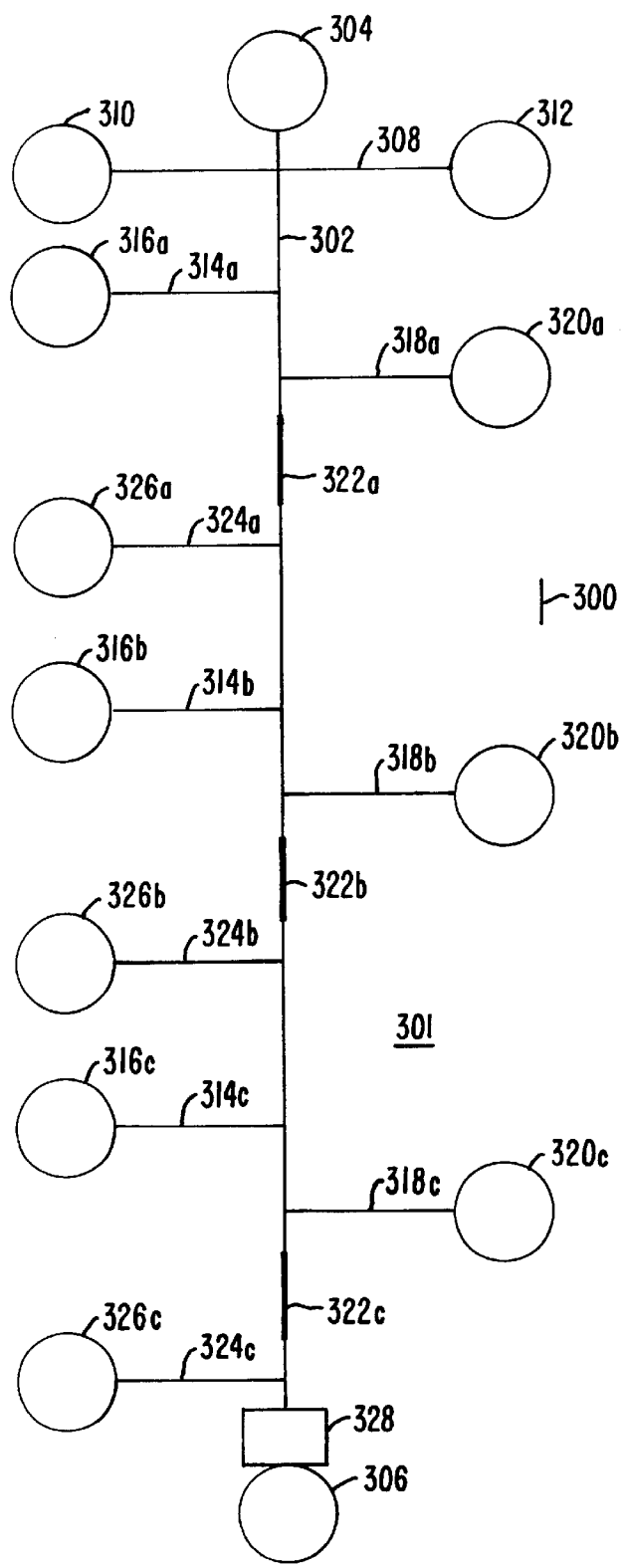
FIG. 3 depicts a top view of a non-thermal amplification apparatus.

An example of a microfluidic device for practicing non-thermal amplification is illustrated in FIG. 3. For ease of discussion, the operation of this device is described with reference to the use of base (NaOH) mediated denaturation and neutralization with acid (HCl). As shown, the device 300 is illustrated as being fabricated in a planar substrate 301, and including a main channel 302 originating from sample reservoir 304 and terminating in waste reservoir 306. The device also includes a transverse channel 308 which intersects the main channel, and has at its termini, buffer reservoir 310 and waste reservoir 312. Main channel 302 is alternately intersected by NaOH introduction channels (314*a*, 314*b* and 314*c*) fluidly connected to reservoirs which contain an appropriate concentration of NaOH (316*a*, 316*b* and 316*c*, respectively) and HCl introduction channels (318*a*, 318*b* and 318*c*) which are fluidly connected to reservoirs (320*a*, 320*b* and 320*c*, respectively) which contain an appropriate concentration of HCl, for neutralizing the base. In the direction of flow along the main channel 302, from the sample reservoir 304 to the waste reservoir 306, after each intersection of the main channel 302 with the HCl introduction channels, 318*a*, 318*b* and 318*c*, there is disposed within the main channel, a desalting region 322*a*, 322*b* and 322*c*, e.g., a portion of the channel that includes an appropriate gel exclusion matrix, nucleic acid binding region, or the like, for separating the salts present in the sample fluid from the amplified nucleic acid. After the desalting regions, the main channel is intersected by enzyme/NTP introduction channels 324*a*, 324*b* and 324*c*, which are fluidly connected to reservoirs (326*a*, 326*b* and 326*c*) which contain effective amounts of an appropriate DNA polymerase, as well as the four nucleoside triphosphates or deoxynucleoside triphosphates (NTPs). A detection window 328 is shown across the main channel 302 near the terminus of the channel into waste reservoir, to detect the product of the overall amplification process. Optional separation regions are also provided in the terminal portion of the main channel 302 between the last desalting region 322*c* and the final waste reservoir 306.

In operation, a sample containing a nucleic acid of interest, e.g., that is sought to be amplified, is introduced along with appropriate primer sequences into main channel 302, e.g., via sample reservoir 304. A stream of sample/primer is transported along main channel 302 and out to waste reservoir 312 along transverse channel 308, e.g., by applying appropriate voltages at the various reservoirs, as described herein. A measured slug of sample/primer is then pumped into main channel 302. Slugs of sample are optionally introduced from an external source, e.g., from a sampling system, e.g., as described in commonly assigned U.S. Pat. Nos. 5,779,868 and 5,880,071, each of which is incorporated herein by reference in its entirety for all purposes.

Following introduction into the device, the sample/primer mixture is then transported up to the intersection of main channel 302 and base introduction channel 314*a*, whereupon the sample is mixed with a stream of NaOH, that is delivered into main channel 302 from reservoir 316*a*, thereby denaturing the nucleic acid of interest. The denatured sample/primer mixture continues down main channel until it reaches the intersection of the main channel with the HCl introduction channel 318*a*, whereupon the denatured sample/primer mixture is mixed with the HCl, thereby neutralizing the mixture and allowing the denatured strands to re-anneal with the primer sequences.

Following this annealing step, the annealed mixture is then transported through a desalting region 322a, to separate the nucleic acid/primers of interest from salts and low molecular weight contaminants. The desalted, annealed mixture then continues down the main channel until it reaches the intersection of the main channel 302 with enzyme/NTP introduction channel 324a, whereupon the mixture is mixed with an effective amount of DNA polymerase enzyme in combination with effective amounts of the four NTPs used for amplification, and other requisite components for amplification, e.g., Mg++, KCl, etc., whereupon the enzyme will catalyze extension of the primers along the template nucleic acid of interest.

This process of denaturing/annealing and extending the nucleic acid of interest is continued along the main channel for the desired number of cycles. Although the illustrated device only shows sufficient denaturant/neutralizer/enzyme channels for three cycles, this is solely for ease of discussion. It will be readily appreciated that the number of cycles can be readily increased by increasing the number of such channels in the device.

It will be readily apparent that a number of different channel geometries er effective in producing the non-thermal amplification devices and systems of the present invention.

Synthesis and Selection of Primers and Primer Sets—Application to Microfluidic Sequencing Oligonucleotides for use as primers or probes, e.g., in sequencing or PCR or non-thermal amplification reactions in microfluidic apparatus are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

While primers can hybridize to any of a number of sequences, selecting optimal primers is typically done using computer assisted consideration of available sequences and excluding potential primers which do not have desired hybridization characteristics, and/or including potential primers which meet selected hybridization characteristics. This is done by determining all possible nucleic acid primers, or a subset of all possible primers with selected hybridization properties (e.g., those with a selected length, G:C ratio, uniqueness in the given sequence, etc.) based upon the known sequence. The selection of the hybridization properties of the primer is dependent on the desired hybridization and discrimination properties of the primer. In general, the longer the primer, the higher the melting temperature. In addition, it is more difficult to generate a set of primers which includes all possible oligonucleotides for a given length, as the required number of primers increases exponentially. For example, all possible 3-mers requires $4^3$ primers, all possible 4-mers requires $4^4$ primers, all possible 5-mers requires $4^5$ primers, all possible 6-mers requires $4^6$ primers, etc. Standard sequencing primers are often in the range of 15–20 nucleotides in length, which would require sets of $4^{15}$ to $4^{20}$ nucleotides, or $1.1 \times 10^9$ to $1.1 \times 10^{12}$ primers.

While it is possible to make such large sets of primers using combinatorial chemical techniques, the associated problems of storing and retrieving billions or even trillions of primers make these primer sets less desirable. Instead, smaller sets of primers used in a modular fashion are desirable.

For example, Ulanovsky and co-workers have described the mechanism of the modular primer effect (Beskin et al. (1995) *Nucleic Acids Research* 23(15):2881–2885) in which short primers of 5–6 nucleotides can specifically prime a template-dependent polymerase enzyme when 2–3 contiguously annealing, but unligated, primers are used in a polymerase dependent reaction such as a sequencing reaction. Polymerase enzymes are preferentially engaged by longer primers, whether modular or conventional, accounting for the increased specificity of modular primers. Because it is possible to synthesize easily all possible primers with 5–6 nucleotides (i.e., $4^5$ to $4^6$ or 1024 to 4096 primers), it is possible to generate and utilize a universal set of nucleotide primers, thereby eliminating the need to synthesize particular primers to extend nucleotide sequencing reactions of nucleotide templates. In an alternative embodiment, a ligase enzyme is used to ligate primers which hybridize to adjacent portions of a template, thereby providing a longer primer.

A modified version of the use of the modular primer strategy, in which small nucleotide primers are specifically elongated for use in PCR to amplify and sequence template nucleic acids has also been described. The procedure is referred to as DNA sequencing using differential extension with nucleotide subsets (DENS). See, Raja et al. (1997) *Nucleic Acids Research* 25(4):800–805. Thus, whether standard Sanger-style sequencing or direct PCR sequencing using boronated nucleotides and a nuclease (see, Porter et al. 1997, supra.) are desired, small sets of short primers are sufficient for use in sequencing and PCR and are desirable.

It is expected that one of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology*, volume 20; and Tijssen (1993) *Laboratory Techniques in biochemistry and molecular biology—hybridization with nucleic acid probes*, e.g., part I chapter 2 "overview of principles of hybridization and the strategy of nucleic acid probe assays", Elsevier, New York provide a basic guide to nucleic acid hybridization. Innis supra provides an overview of primer selection.

One of skill will recognize that the 3' end of an amplification primer is more important for PCR than the 5' end. Investigators have reported PCR products where only few nucleotides at the 3' end of an amplification primer were complementary to a DNA to be amplified. In this regard, nucleotides at the 5' end of a primer can incorporate structural features unrelated to the target nucleic acid; for instance, in one embodiment, a sequencing primer hybridization site (or a complement to such as primers depending on the application) is incorporated into the amplification primer, where the sequencing primer is derived from a primer used in a standard sequencing kit, such as one using a biotinylated or dye-labeled universal M13 or SP6 primer. These structural features are referred to as constant primer regions. The primers are typically selected so that there is no complementarity between any known target sequence and any constant primer region. One of skill will appreciate that constant regions in primer sequences are optional.

The primers are selected so that no secondary structure forms within the primer. Self-complementary primers have poor hybridization properties, because the complementary portions of the primers self hybridize (i.e., form hairpin structures). Modular primers are selected to have minimal cross-hybridization, thereby preventing competition between individual primers and a template nucleic acid and preventing duplex formation of the primers in solution, and possible concatenation of the primers during PCR. If there is more than one constant region in the primer, the constant regions of the primer are selected so that they do not self-hybridize or form hairpin structures.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector™ program from Kodak. An alternate program is the MFOLD program (Genetics Computer Group, Madison Wis.) which predicts secondary structure of, e.g., single-stranded nucleic acids. In addition to programs for primer selection, one of skill can easily design simple programs for any or all of the preferred selection steps.

Alternative Sequencing Strategies

Although the present invention is described for exemplary purposes as using enzymatic sequencing methods (e.g., using the chain termination methods of Sanger, or the exonuclease/PCR methods described above), it will be appreciated that sequencing by hybridization protocols and chemical degradation protocols are also adapted to use in the present invention.

In chemical degradation methods, the template is typically end-labeled with a radio-active or florescent label and then degraded using the well-known Maxam-Gilbert method. As applied to the present invention, the chemicals used to degrade the nucleic acid are sequentially contacted to the template and the resulting size fragments detected by electrophoresing the fragments through a microchannel as described supra.

Sequencing by hybridization is generally described, e.g., in U.S. Pat. No. 5,202,231, to Drmanac et al. and, e.g., in Drmanac et al. (1989) Genomics 4:114–128. As adapted to the present invention, a microfluidic device is provided having a source of labeled primers as described herein, and a source of template to be sequenced. The template and the labeled primer are hybridized under highly stringent conditions, which permit hybridization to occur only if the primers are perfectly complementary to the template. In one embodiment, primers having complementarity to a known region and also having an additional base or additional bases at the 3' or 5' end are separately hybridized to the template; those primers which are perfectly complementary to the template (i.e., where the known and additional bases are perfectly complementary to the template) are detected. From the detection of the additional base or bases, additional primers are selected and the process is repeated. Using this strategy, it is possible to sequence the entire template nucleic acid.

Typically, the sequence is extended by only a single base with each specific hybridization. This is because, as described supra, it is easier to make complete sets of small oligonucleotides (e.g., there are only 4,096 6 nucleotide primers) than it is to make complete sets of large oligonucleotides. However, several bases are optionally detected using larger primers. One advantage of detecting larger regions of complementarity is that, on average, it is more efficient. It will be appreciated that it is not necessary to test all possible sequences for specific hybridization if more bases than one adjacent to the known regions are present in the primers used in the sequencing by hybridization reaction. This is because bases are tested sequentially only until a perfectly complementary sequence to the template is found. Once this primer is determined, additional possible primers for this region are not tested; instead, the process is repeated to detect the flanking region. Commonly, the primers have between about 1 and about 4 nucleotides which flank known regions of complementarity.

The detection of hybridization is carried out as described supra. Typically, the template is captured in a region of the microfluidic substrate and primers are sequentially contacted to the captured template under stringent hybridization conditions. After hybridization and detection of hybridization (e.g., by tracking a fluorescent or a radio-active label on the primer) the primer is washed off of the template (e.g., by varying the salt concentration or heat at the site of hybridization) and the process is repeated with a second primer.

Integrated Fluidic Operations

In addition to sequencing applications, the microfluidic devices and methods herein are useful in performing other operations that rely upon a large number of iterative individual fluid manipulations, e.g., reagent additions, combinations, apportionings, etc.

Serial Diluter

The simplest illustration of iterative fluid manipulations in a microfluidic system is in the serial dilution of fluids. Dilution of samples, reagents and the like, is a particularly problematic area in microfluidic devices. In particular, when operating at extremely small volumes, bleed over effects, diffusion and the like prevent the accurate control and transport of fluids, thereby effectively limiting the dynamic range of dilution available through the device. Accordingly, one achieves a greater dynamic range of dilution by performing iterative serial dilutions of a sample fluid. In particular, rather than making a single 1:100 or 1:1000 dilution, one serially makes 1:10 dilutions to achieve the desired dilution. Because each dilution is relatively minor, fluid control is not as substantial a problem.

In the devices of the present invention, dilution of a sample is typically carried out in a device that includes a main channel intersected by one or more diluent channels, which are in fluid communication with one or more diluent reservoirs, respectively. A sample or reagent is transported, e.g., electroosmotically, along the main channel. Diluent is then transported into the main channel and allowed to mix with the sample, reagent or other fluid for which dilution is sought. Control of the relative volumes of sample and diluent is affected by controlling the electrical fields applied to each of these solutions and which drive their electroosmotic flow within the system, as described above. By incorporating multiple diluent channels, one can further increase the range of dilution of which the device is capable.

Integrated Systems for Assay Normalization

One similar application of the integrated systems of the invention is the titration of assay components into the dynamic range of an assay. For example, an assay can first be performed where one or more components of the assay are not within the range necessary for adequate performance of the assay, e.g., if the assay is performed using a concentration which is too high or too low for some components, the assay may not provide quantitative results. This need to titrate assay components into the dynamic range of an assay typically occurs where one or more component of the assay is present at an unknown activity or concentration. Ordinarily, the assay must be run at several concentrations of components, i.e., the assay is run a first time, components are diluted, the assay is run a second time, etc. until the assay can be performed within the dynamic range of the assay. It will be appreciated that this iterative approach can involve several unknown concentrations simultaneously, requiring considerable trial and error.

In the integrated systems of the invention, an assay can be performed at as many concentrations of components as necessary to titrate the assay components into the dynamic range of the assay, with the results of each assay being used to optimize additional assay points. Similarly, titration curves, which are often the result of multiple assay runs with different component concentrations are determined by performing repeated assays with different concentrations of components. Different concentrations of assay components in separate assays can be monitored serially or in parallel.

The ability to titrate and optimize assays is useful for diagnostic assays, for determining concentrations or activities of selected components in a system (proteins, enzymes, nucleic acids, small molecules, etc.). Furthermore, the present integrated systems provide for rational selection of assay conditions as data is acquired. For example, in one embodiment, a diagnostic assay needs to be performed using several components which are present at initially unknown concentrations or activities. A first series of concentration or activity assays is performed to determine the activity or concentration of particular components, e.g., enzyme, protein, inhibitor, co-factor, nucleic acid, or the like. After these assays are performed and the concentrations or activities of some or all of the components for the diagnostic assay are determined, the integrated system selects appropriate amounts of the assay components, performs any necessary dilutions, combines the assay components and performs the diagnostic assay. Similarly, further data points can be collected by adjusting the concentrations or amounts of diagnostic assay components and re-running the assay. All of the fluid manipulations are performed rapidly and the integrated system is able to assess and compile the results of individual data points or individual assays to select which additional assays need to be performed for assay verification.

In its most basic form, assay optimization involves the identification of all factors affecting a reaction result, followed by the systematic variation of each of these variables until optimal reaction conditions are identified. This is generally termed an "OFAT" method for "one factor at a time." Thus, assuming a simple two reagent reaction, one would first identify the factors affecting the outcome, e.g., concentration of reagent A, concentration of reagent B and temperature. One would then run the assay where one factor was varied while the others remained constant. For example, one would perform the same reaction at numerous different concentrations of reagent A, while maintaining the concentration of reagent B and the temperature. Next, reagent B would be varied while reagent A and temperature remained constant, and finally, the temperature would be varied.

Even in this simplest form, the number and complexity of necessary reactions is apparent. When one considers that most reactions will have far more than three variables, and that these variable will not be independent of each other, the possibility of manually performing these assays, or even performing them in currently available automated formats becomes a daunting prospect. For example, while robotic systems using microwell plates can perform large numbers of manipulations to optimize assay parameters, such systems are very expensive. Further, as these systems are typically limited to the bench scale volumes described above, they require large volumes of reagents and large amounts of space in which to operate.

The devices, systems and methods of the present invention permit the optimization of large numbers of different assays, by providing an extremely low volume, automatable and sealed format in which such optimization can occur rapidly and automatically. For example, the devices can run a first fluidic operation by combining a preselected volume of a first reactant with a preselected volume of a second reactant, at a desired or preselected temperature for a desired or preselected amount of time. The device then repeats the assay, but varies at least one of the volume of the first or second reactants, the temperature, or the amount of time allowed for the reaction. This is repeated until a desired number of varied reactions are performed, i.e., generating sufficient data to permit an estimation of optimal assay conditions which will produce an optimal result of the reaction, within a desired range of statistical significance. "optimal assay conditions" include those conditions that are required to achieve the desired result of the reaction. Such desired results can include maximization of reaction yields, but also includes assay conditions which are optimized for sensitivity to one variable, e.g., inhibitor concentration, and the like.

Figure 4A:
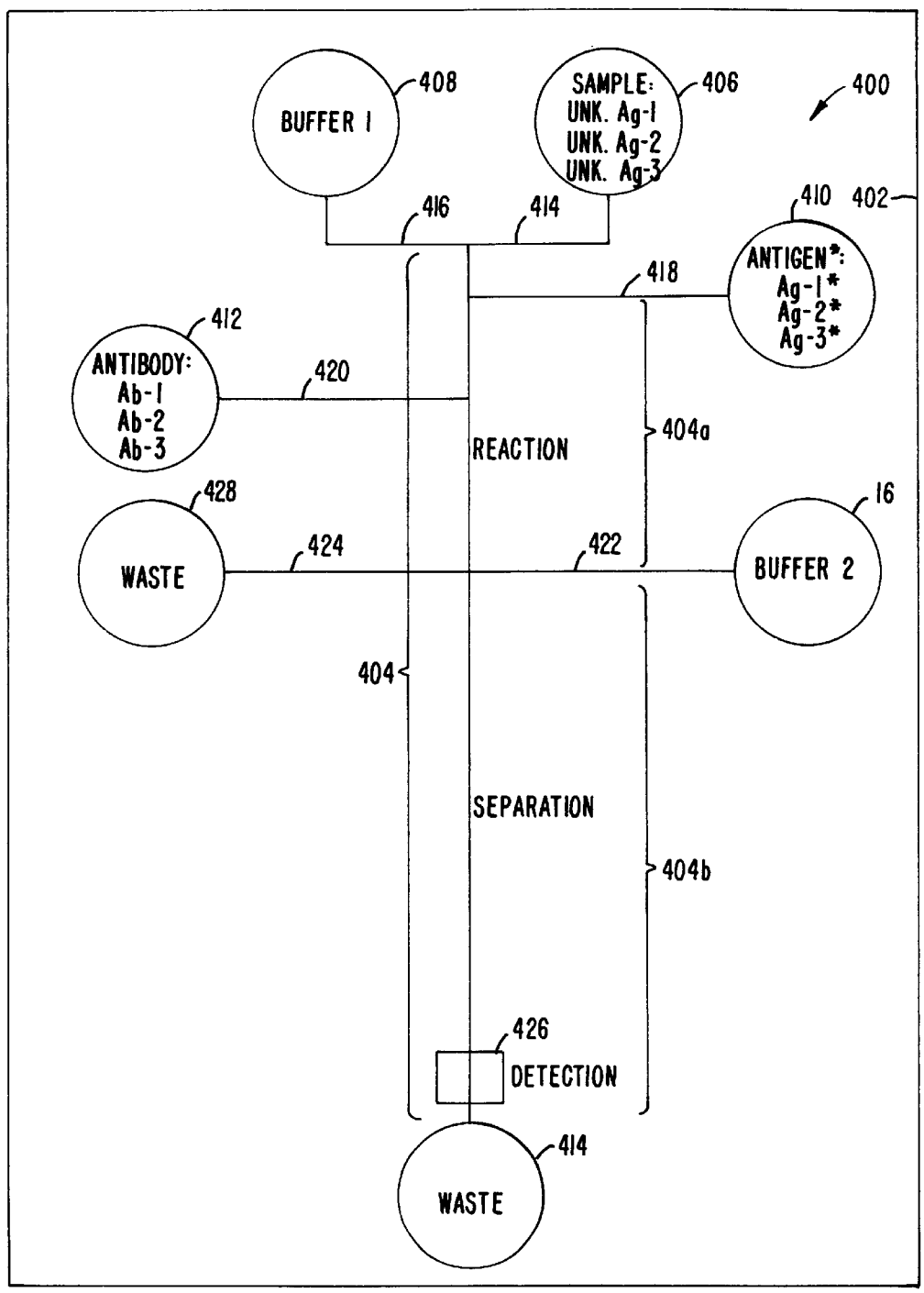
FIGS. 4A–4D depicts a top view of a reaction and separation apparatus and output data from the apparatus.

An assay optimization using the microfluidic devices and systems of the invention are illustrated through a competitive binding assay, e.g., antibody-antigen binding. A microfluidic device for performing a binding assay is illustrated in FIG. 4A. As shown, the microfluidic device 400 is fabricated into a planar solid substrate 402. The device includes a main channel 404, which includes a separate reaction zone 404*a* and separation zone 404*b*. The device also includes a sample well 406, a first buffer well 408, an antigen well 410, an antibody well 412 and a waste well 414. Second buffer well 416 and waste well 428 are also included. The main channel 404 is linked to wells 406 through 412 via fluid channels 414–420, respectively. Wells 416 and 428 are linked to the main separation channel 404*b* via channels 422 and 424, respectively. Fluid direction within the device is carried out substantially as described herein, e.g., via the concommittent application of appropriate electrical voltages at multiple wells. Again, the device includes a detection zone 426 toward one end of the main channel, to allow detection of the labeled components as they move along the main channel.

In operation, the antibody panel to be screened against the sample is provided as a mixture or cocktail, and placed in antibody well 412. A similar cocktail of the various different, labeled antigens for which the sample is being screened is placed in the antigen well 410. Labeling of antigens, or in some cases, antibodies, can be carried out by a variety of well known methods, and can include enzymatic, fluorescent, calorimetric, luminescent or other well known labeling techniques.

Figure 4B:
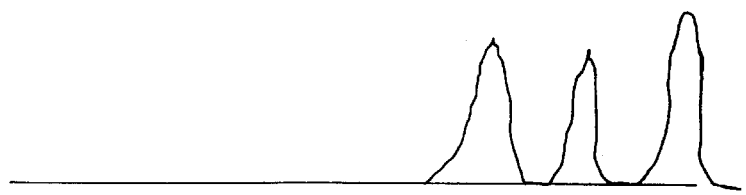

Initially, an antigen control is run. Specifically, antigen is pumped from well 410 to waste well 428 via channels 418, 404 (through zones 404*a*) and 424. A measured fluid slug or region of labeled antigen is then injected into and pumped along the main channel 404 and through separation zone 404*b*. The labeled antigens electrophorese into the constituent antigens, which are flowed past a detector 426. An example of data obtainable from the antigen control is shown in FIG. 4B, where each of the three peaks represents a different antigen in the antigen cocktail. The peak heights for the antigen control are measured for later use in quantification of the antigen in the sample. From the relative retention times, one can also determine that all of the labeled antigens are present in the cocktail.

Figure 4C:
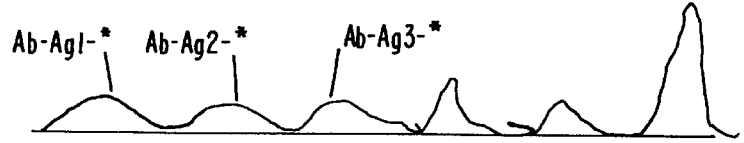

Next, an antigen/antibody complex control is run. In particular, constant streams of antibody and antigen are pumped from their respective wells into the main channel 404, and particularly the reaction zone 404a, and out to waste well 428. A measured slug of the mixture is then injected into the separation channel 404b. Complexation of the antigen with the antibody results in a shift in the electrophoretic mobility of the labeled complex relative to that of the labeled antigen alone. FIG. 4C represents data obtainable from the antigen/antibody complex control, where the three peaks detected first represent the uncomplexed labeled antigen, and the last three peaks represent the labeled antigen/antibody complex. Of course, in some aspects, electrophoretic mobility is affected in an opposite manner, i.e., resulting in a complex eluting faster than its constituent elements, and both contingencies are envisioned here. Concentrations of antibody and labeled antigen will also generally be titrated to yield optimal responses when contacted with the sample. Methods of titrating these elements are well known in the art.

Figure 4D:
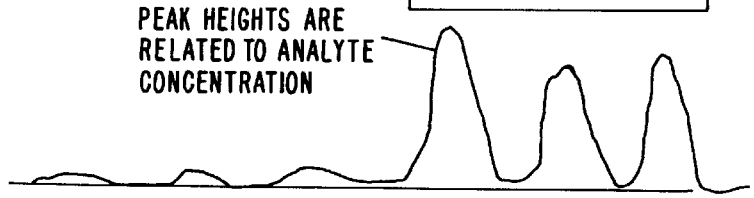

Finally, in a screening run, streams of antibody, antigen and sample are flowed continuously into the reaction channel 404a and into waste well 428. A slug of this mixture is then injected into the separation channel 404b. Any antigen of interest in the sample will compete for binding to its counterpart antibody with the corresponding labeled antigen, resulting in a reduction in the level of labeled complex, or an increase in the level of labeled, uncomplexed antigen. An example of data obtainable from a test run is shown in FIG. 4D. As shown, the data would indicate that the sample contains an amount of antigen AG-1 and AG-3, but little or no AG-2. A quantitative determination of the levels of these various antigens within the sample can be obtained by comparing the peak heights, either labeled, uncomplexed antigen, or labeled complex, from the test run to those of one or both of the control runs, where the difference (e.g., $\delta_1$ and/or $\delta_2$) is indicative of the amount of antigen in the sample. See, e.g., Evangelista et al., *Am. Clin. Lab*:27–28 (1995).

Additional wells and channels are optionally provided connected to different reagent injection channels, e.g., 414–422, to dilute these various elements, in order to optimize the particular assay system.

Where different antigens, antibodies or complexes thereof, in a given panel screen lack sufficiently different electrophoretic mobilities, one or more these elements are optionally chemically modified, e.g., by the addition of charged groups, to alter the electrophoretic mobility of that element without substantially affecting that element's interaction with other elements.

In performing the above-described assay format, a number of variables would be expected to affect the assay performance. A number of these variables are set forth in Table 1, with a number of possible levels set forth for each variable.

TABLE 1

| Variable | # of Levels | Levels | | | |
|---|---|---|---|---|---|
| Sample Conc. | 3 | low | medium | high | |
| % Ratio of [Sample:Ag:Ab] | 4 | 33:33:33 | 50:25:25 | 25:50:25 | 25:25:50 |

TABLE 1-continued

| Variable | # of Levels | Levels | |
|---|---|---|---|
| Antibody type (vendor) | 2 | Vendor A | Vendor B |
| Reaction Time | 2 | 0.4 mm/s | 0.8 mm/s |
| Reaction Temp. | 2 | 25° C. | 37° C. |
| Injected Volume | 2 | 20 pl | 50 pl |
| Separation Time | 2 | 0.4 mm/s | 0.8 mm/s |

As provided in this example, the assay has a total of 7 variables, each of which has 2, 3 or 4 levels of variability. In order to perform a full factorial experiment covering these variables, 384 separate reaction runs would be required. Even assuming a ⅛ fractional factorial experiment, 48 separate runs would be required, which when duplicated, would result in 96 separate runs. When performed at a bench scale, such an experiment would take hours and would require substantial attention from the investigator to ensure that each assay run is performed correctly and accurately. However, in the above described microfluidic format, each run is automatically performed typically in approximately 30 seconds per run. This would permit running all 48 distinct runs, in duplicate, in less than one hour (in parallel microfluidic formats, as discussed below, the assay could easily be run in a few minutes). Further, the entire experiment is automatically controlled by the computer control system of the microfluidic system, as described herein.

After all of the assays are performed, the results are analyzed and optimal assay conditions are determined. Analysis of these results is typically carried out in the control computer system using readily available computer software, designed for experimental optimization, e.g., Design-Ease™ statistical optimization software.

Drug Screening Assays

In addition to sequencing, the integrated microfluidic system of the invention is broadly useful in a variety of screening assays where the results of mixing one or more components are to be determined, and particularly, where the results determined are used to select additional reagents to be screened.

As described more fully below, the integrated microfluidic system of the invention can include a very wide variety of storage elements for storing reagents to be assessed. These include well plates, matrices, membranes and the like. The reagents are stored in liquids (e.g., in a well on a microtiter plate), or in lyophilized form (e.g., dried on a membrane), and can be transported to an assay component of the microfluidic device (i.e., a microfluidic substrate having reaction channels or the like) using conventional robotics, or using an electropipettor as described below.

Because of the breadth of the available sample storage formats for use with the present invention, virtually any set of reagents can be sampled and assayed in an integrated system of the present invention. For example, enzymes and substrates, receptors and ligands, antibodies and ligands, proteins and inhibitors, cells and growth factors or inhibitors, viruses and virus binding components (antibodies, proteins, chemicals, etc.) immunochemicals and immunoglobulins, nucleic acids and nucleic acid binding chemicals, proteins, or the like, reactant chemicals (acids, bases, organic molecules, hydrocarbons, silicates, etc.) can all be assayed using the integrated systems of the invention. For example, where a molecule which binds a protein is desired, potential binding moieties (chemicals, peptides, nucleic acids, lipids, etc.) are sequentially mixed with the protein in a reaction channel, and binding is measured (e.g., by change in electrophoretic mobility, quenching of fluorescent protein residues, or the like). Thousands of compounds are easily screened using this method, in a short period of time (e.g., less than an hour).

An advantage of the integrated nature of the present system is that it provides for rational selection of structurally or functionally homologous compounds or components as the assay progresses. For example, where one compound is found to have binding activity, the selection of a second compound to be tested can be performed based upon structural similarity to the first active compound. Similarly, where a compound is shown to have activity in a cell (e.g., up-regulation of a gene of interest) a second compound affecting the same cellular pathway (e.g., calcium or inositol phosphate second messenger systems, etc.) can be selected from the group of available compounds for testing. In this way, it is possible to focus screening assays from purely random at the outset to increasingly focused on likely candidate compounds as the assays progress.

Further details on drug screening assays adaptable to the present invention are found in U.S. Pat. No. 5,942,443.

Additional Nucleic Acid Analysis

Genomic material is subject to a certain amount of variation from one individual of a particular species to another. For example in a mammalian genome of approximately 3 billion base pairs, approximately 0.1%, or 3 million base pairs would be expected to vary among individuals, and a large number of these variations would be expected to be linked to or result in potentially important traits.

A number of methods are currently available for identifying and distinguishing these variations other than simply sequencing the nucleic acids as described above. For example, Kozal et al., *Nature Medicine* 2(7):753–759 (1996), describes the use of high density oligonucleotide probe arrays in identifying naturally occurring mutations in HIV infected patients, which mutations augment resistance to particular antiviral agents, e.g., protease inhibitors.

Alternative methods for identifying these variations include actual DNA sequencing discussed above, oligonucleotide ligase assays, including LCR, DNA polymerase based methods, and allele specific amplification methods. Although these methods are generally effective at benchtop scales when analyzing single or few loci, when comprehensive genetic information is desired, e.g., requiring analysis of large numbers of loci, the conditions must be optimized for each locus, requiring the performance of massive numbers of experiments, rendering such methods overly expensive, cumbersome and largely impractical.

Figure 5A:
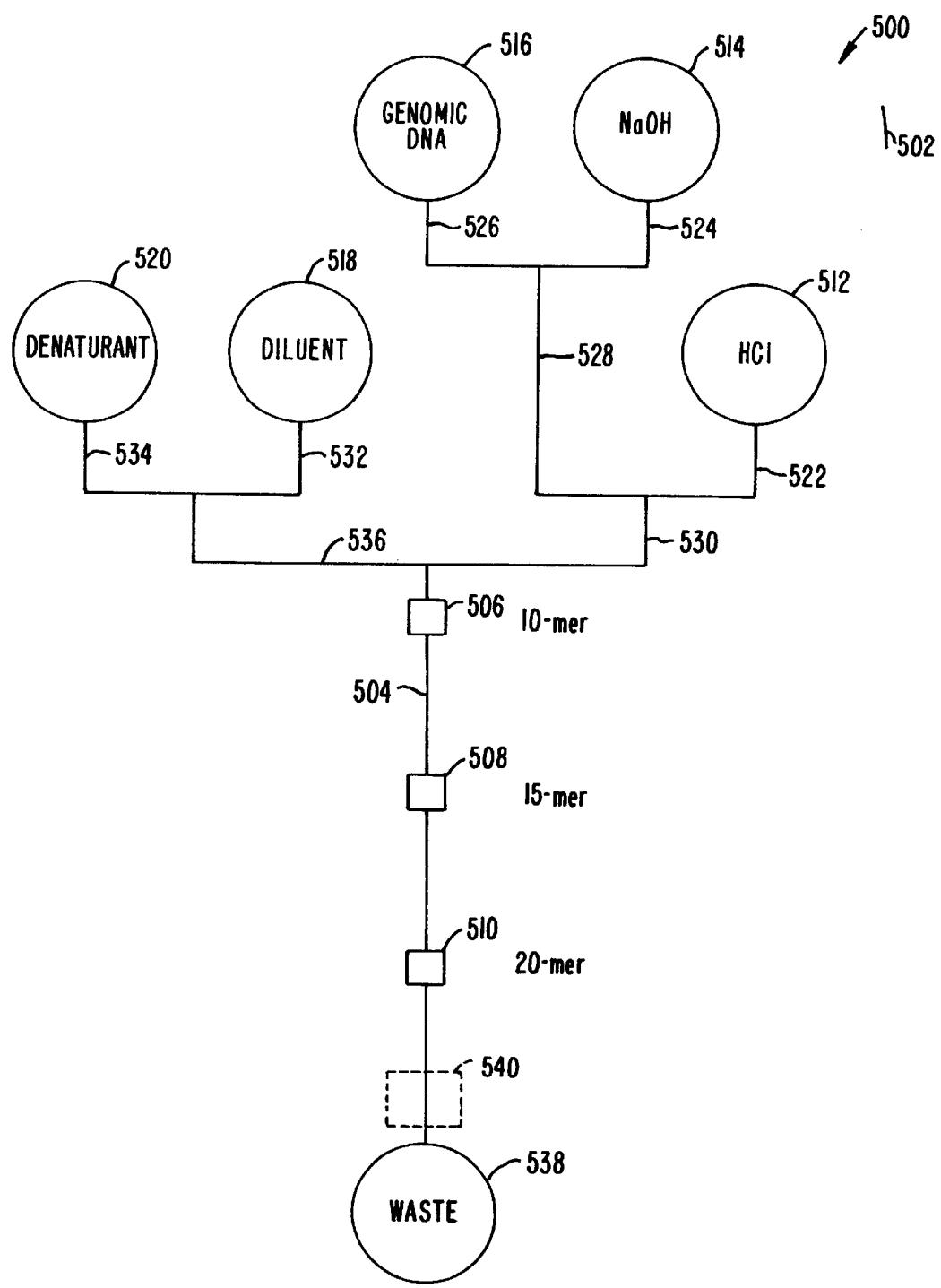
FIG. 5A depicts a top view of an apparatus for discriminating nucleic acids based on sequencing; 5B depicts an optional separation channel.

In related aspects, the microfluidic devices and systems can be readily used to perform nucleic acid analysis for identifying and mapping such variations, without the need for amplification or sequencing steps. Briefly, the particular assay system employs a hybridization of a complex nucleic acid sample to groups of oligonucleotide probes that are complementary to different portions of the target sequence and that are immobilized in different regions of a reaction channel. Enrichment of a target nucleic acid of interest is carried out by the iterative hybridization, washing and release of the target from these oligonucleotide probes. These probes are optionally complementary to different portions of the target or overlapping portions and they are optionally the same or different lengths. A schematic illustration of a device for such analysis is shown in FIG. 5A.

As shown, the device 500 is again fabricated into a solid substrate 502 and includes a main analysis channel 504. The main analysis channel includes first, second and third hybridization sites 506, 508 and 510, respectively. Each of reservoirs 512–520 are connected to the main analysis channel by a series of intersecting channels 522–536.

In operation, a sample containing a targeted nucleic acid is placed in reservoir 516. Where the sample includes double-stranded genomic DNA, the sample is optionally denatured under basic conditions. This is accomplished, e.g., by delivering a volume of dilute base, e.g., NaOH, from reservoir 514 via channel 524, to be mixed with the sample at intersection of channels 526 and 524. This intersection optionally comprises a widened channel or chamber fabricated into the substrate, to facilitate mixing of the sample and dilute base or to allow for more refined control of reaction times. The denatured sample is then moved along channel 528. The dilute base is optionally neutralized by delivering an equal volume of similarly dilute acid, e.g., HCl, from reservoir 512, via channel 522, to be mixed with the basic sample at the intersection of channels 522 and 528, which again, can comprise a widened channel or chamber design to facilitate mixing or to allow for more refined control of reaction times. Because samples will typically include highly complex nucleic acids, this complexity generally prevents the sample from rapidly re-annealing. The neutralized, denatured sample is then moved into the main analysis channel 504. Within the main analysis channel are hybridization sites 506, 508 and 510, at which sites are immobilized short, synthetic oligonucleotides that are complementary to different portions of a target sequence. Immobilization of oligonucleotides on solid substrates is optionally carried out by a variety of known methods. For example, often solid supports will include functional groups to which oligonucleotides are optionally coupled. Alternatively, substrates are optionally treated to provide such groups, e.g., by silanation of silica substrates.

These oligonucleotides comprise a set of sequences having homology to the target sequence of interest, but not necessarily to each other, preferably of sequentially increasing lengths along the series of sites within the main channel 504, such as 10, 15, and 20 nucleotides in length, at sites 506, 508 and 510, respectively. The lengths of the probes generally varies depending upon the length and composition of the target sequence. The target sequence is preferably at least as long as, if not longer than the longest oligonucleotide. Typically, the probes are arranged in the reaction channel from lowest affinity to highest affinity in the direction of flow for the gradient of denaturant. Target sequence that dissociates from the first or weakest affinity probe will then associate with the next probe in the series, and so on. Stated another way, the lowest affinity probe will be located in the reaction channel at a point nearest to the source of denaturant, and will therefore receive the denaturant gradient first. Probes with stronger affinity will be located sequentially further from the source of denaturant, with the probe having the strongest affinity being furthest from the source of denaturant.

Once directed into the reaction channel 504, the sample is presented to the first group of probes 506, under conditions suitable for hybridization to those probes. By "conditions suitable for hybridization" is meant conditions of chemical composition, temperature, and the like, under which the target sequences are capable of hybridizing to a particular probe sequence. "Stringent hybridization" in the context of these nucleic acid hybridization experiments are sequence dependent, and are different under different environmental parameters. Generally, highly stringent hybridization conditions are selected to be about 5°–15° C. lower than the thermal melting point ($T_m$) for the specific sequence at a defined ionic strength and ph. The $T_m$ is the temperature (under defined ionic strength and pH) at which 50% of the target RNA sequence hybridizes to a perfectly matched oligonucleotide probe. Very stringent conditions are selected to be nearly equal to the $T_m$ for a particular probe (e.g., 0°–5° C. below the melting temperature). An oligonucleotide "specifically hybridizes" to a particular target when the probe hybridizes with a least twice the signal intensity of a control probe. Where the control probe differs by less than 10% (often by only 1 nucleotide) from a test probe, the test probe is an "allele-specific" probe (to indicate that the test probe can be used to distinguish between two different alleles of a target which differ by a single nucleotide). See also, Gait, ed. *Oligonucleotide Synthesis: A Practical Approach,* IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology,* volume 20; and Tijssen (1993) *Laboratory Techniques in biochemistry and molecular biology— hybridization with nucleic acid probes,* e.g., part I chapter 2 "overview of principles of hybridization and the strategy of nucleic acid probe assays", Elsevier, New York for a basic guide to nucleic acid hybridization.

Sequential purification of the target portion of the genome can be achieved by sequential selective hybridizations to these oligonucleotides. Thus, for example, when the sequence of interest is 20 nucleotides or longer in length, one would expect that a shorter oligonucleotide, such as a 10-mer, will hybridize to many more sites in the genome than merely the target sequence, just on the statistical basis of any particular sequence of 10 nucleotides appearing in the genome. These sequences will hybridize to the 10-mer oligonucleotide, while non-hybridizing DNA can be washed out of the pool via waste reservoir 538 with diluent in reservoir 518 supplied through channels 532 and 536. The reduced pool, which is actually enriched for sequences hybridizing to the 10-mer, is then subjected to a gradient of denaturant which is delivered from reservoir 520. Useful denaturants include those already described herein, including, e.g., formamide, and the like. The maximal concentration of the denaturant is calibrated to maintain a maximal stability of the target sequence/10-mer duplex, thereby eliminating imperfectly hybridized target sequences from the 10-mer or other probes, including double base and single base mismatched probe/target hybrids. Determination of optimal levels of denaturant is generally carried out experimentally, i.e., by determining optimal hybridization conditions for a given probe sequence.

Denaturant is transported from reservoir 520 through channels 534 and 536, while diluent can be added from reservoir 518 through channel 532 to the intersection of channels 532 and 534. Complexity of the sample nucleic acids is substantially reduced by this step. For example, a typical mammalian genome having over $10^5$ base pairs, would be expected to have approximately $10^3$ sites capable of hybridizing to a 10-mer probe, effectively allowing a one million-fold reduction in sample complexity.

Following removal of less strongly bound species, the denaturant gradient is restored to a level that causes dissociation of the target from the 10-mer probes, but which permits hybridization to the 15-mer oligonucleotide. As a particular sequence of 15 nucleotides statistically occurs with less frequency than a 10 nucleotide sequence, again the complexity of the sample DNA will be reduced when non-hybridized DNA is washed out of the main analysis channel 504. These enrichment steps can be performed with oligonucleotides of increasing length until the desired level of enrichment is achieved. In some embodiments, oligonucleotide probes need not be of increasing length; multiple steps using different oligonucleotide probes will continue to enrich the DNA population for the sequence of interest based on probability of the oligonucleotide sequence occurring in populations of decreasing complexity.

Preferably, at least one enrichment step is performed before hybridization to oligonucleotides that "type" the target sequence for the presence of a particular target sequence or variation.

Although described in terms of use of chemical denaturants, it will be readily appreciated that other chemical or non-chemical treatments are optionally used to vary the hybridization conditions, including adjusting pH, temperature. Similarly, although varied affinity among the probes is generally described as being carried out by use of different length probes, it will also be understood that different probe compositions can also be used to vary affinity of the probe to the target. For example, G-C rich probes will hybridize with greater affinity, i.e., have a higher melting temperature, than A-T rich probes. These chemical properties can be exploited in practicing this aspect of the invention.

Finally, target nucleic acid typed by virtue of its enrichment and subsequent hybridization to a higher affinity probe, e.g., a 15-mer or 20-mer, can be released from the final hybridization site and flowed along the analysis channel 504. The "typed" target sequence is flowed past a detection window 540, whereupon it can be detected, i.e., by virtue of an incorporated labelling group. A variety of direct and indirect labeling and detection methods are well known for nucleic acids, including radiolabeling methods, fluorescent labeling, either directly or from an intercalating fluorescent dye, chemiluminescent labeling, calorimetric labeling, labeling with ligands or anti-ligands, e.g., biotin/avidin or streptavidin, and the like.

In an alternate method, the target sequence can be identified by detecting the accumulation of the detectable label at the final hybridization or "typing" site, following the final washing step.

Melting Point Analysis of Nucleic Acids

In a similar embodiment, the systems, devices and methods of the present invention, can,be used to detect variations in nucleic acid sequences by determining the strength of the hybridization between the targeted nucleic acid and probes that are putative perfect complements to the target. By identifying the difference in stability between the imperfect and perfect hybrids under conditions of increasing hydrogen bond stress, one can identify those nucleic acids that contain a variation.

In practice, a microfluidic device is configured to accept a sample containing an amplified nucleic acid or polynucleotide sequence of interest, convert it to single-stranded form, facilitate hybridization with a nucleic acid probe, such as an oligonucleotide, and then subject the hybridization mixture to a chemical or temperature gradient that distinguishes between perfectly matched targets and those that differ by at least one base pair (mismatch). In some embodiments, one or more loci or targeted areas of the sample polynucleotide are first amplified by such techniques as PCR or sandwich hybridization. In other embodiments, unamplified polynucleotide is provided to the device and amplified therein, such as in the non-thermal amplification embodiments described below.

Figure 5B:
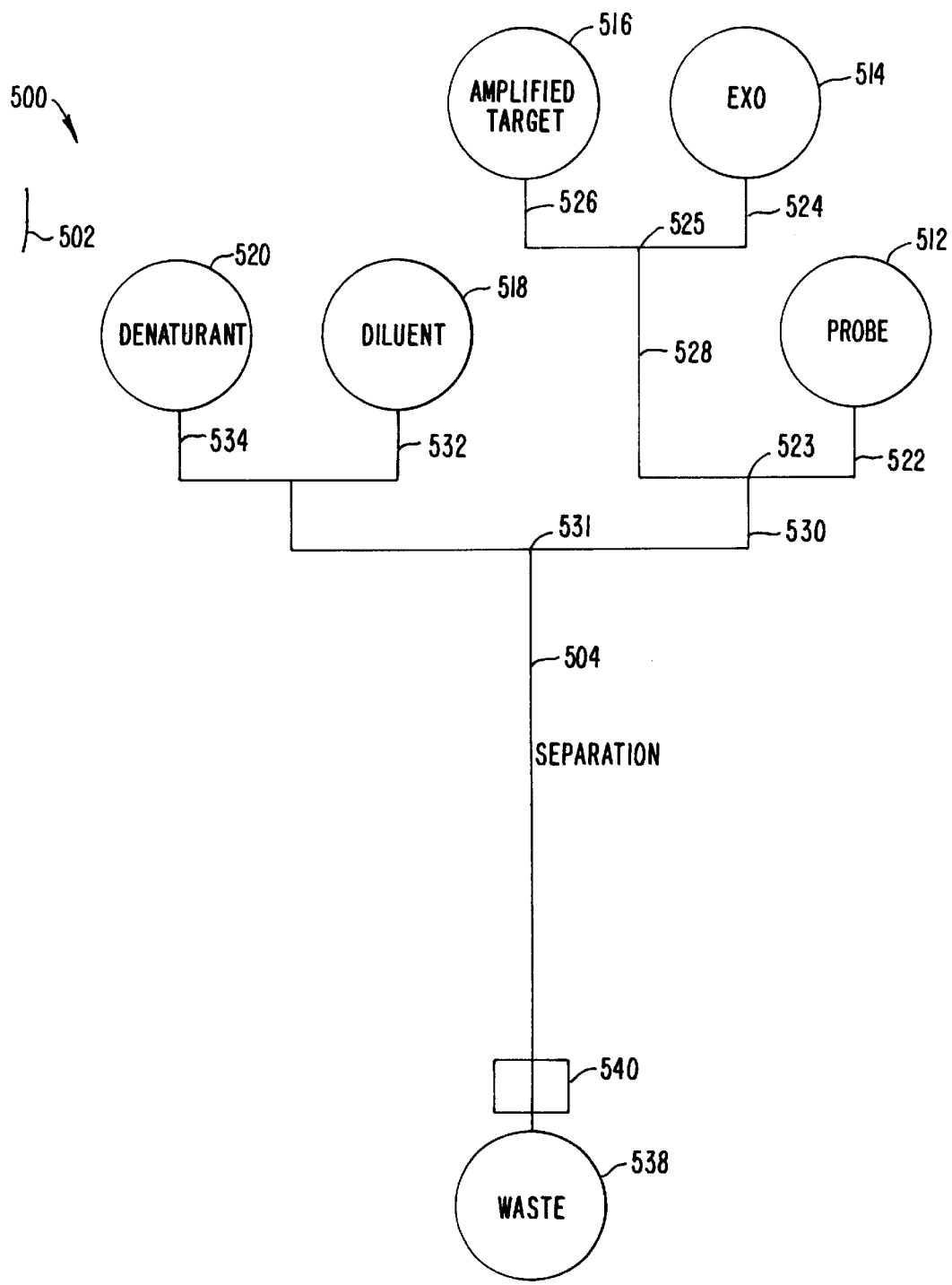

A schematic illustration of a microfluidic device for carrying out this analysis is shown in FIG. 5B employing the same schematic layout as the device shown in FIG. 5A. In this aspect, a sample containing a nucleic acid is introduced into sample well 516. This sample is, e.g., introduced into the device, preamplified, or it can be transported to well 516 from another portion of the device where the nucleic acid was amplified, e.g., in integrated operations. Thus, although shown as a well, sample well 516 can be a reservoir or an inlet supplied by an external reservoir or separate reaction chamber. In some embodiments, when the polynucleotide is amplified, one end of the amplified oligonucleotide (e.g., PCR product) is terminated with groups such as phosphorothioate bonds that prevent exonucleolytic action by enzymes such as T7 DNA polymerase.

A preselected amount of amplified target is then fluidically moved through channel 526. A preselected amount of exonuclease, e.g., T7 DNA polymerase, placed in well 514, is concurrently moved along channel 524. Where channel 526 and 524 intersect (intersection 525), the target and the exonuclease mix in channel 528, and the target is subjected to enzymatic digestion to render the target single-stranded. Alternatively, single stranded target is optionally prepared by asymmetric PCR.

The resulting single-stranded molecules are then moved along channel 528 to the intersection of this channel and probe channel 522. Probe well 512 contains oligonucleotide probes which are putatively complementary to a region of the target which contains a potential variation. The probe containing solution is delivered along probe channel 522 to the intersection 523 with channel. 528, whereupon the probe solution mixes and hybridizes with the single stranded target. As above, a widened channel or chamber is optionally provided at these intersections to facilitate mixing of the materials.

Hybridization of the probe results in a perfect hybrid with no mismatches when the sample polynucleotide contains the complementary sequence, i.e., no variation, or in a hybrid with mismatches if the sample polynucleotide differs from the probe, i.e., contains a sequence variation. The stability of the imperfect hybrid differs from the perfect hybrid under conditions of increasing hydrogen bond stress. A variety of methods are available for subjecting the hybrids to increasing hydrogen bond stress, sufficient to distinguish between perfectly matched probe/target hybrids and imperfect matches. For example, the hybrids are optionally subjected to a temperature gradient, or alternatively, can be subjected to increasing concentrations of a chemical denaturant, e.g., formamide, urea, and the like, or increasing pH.

As shown, the hybridized target/probe mixture is moved through channel 530 to the intersection 531 of this channel with denaturant channel 536. Denaturant, placed in denaturant well 520 is concurrently delivered to intersection 531, whereupon it mixes with the target/probe hybrid. The denaturant can be diluted with an appropriate diluent buffer supplied from diluent well 518 via channel 532. The differences in stability of the hybrids under denaturing conditions can be detected by an integrated separation column such as a capillary channel 528 where molecular sieving can be done.

Following mixing with the denaturant, hybridized and nonhybridized nucleic acids are electrophoretically separated by moving the mixture along separation channel 504. The separation channel can include any of a number of separation matrices, e.g., agarose, polyacrylamide, cellulose, or the like.

The assay is then repeated several times, varying the concentration of denaturant with each successive assay. By monitoring the level of hybrid or single stranded target, one can determine the concentration of denaturant at which the probe-target hybrid is denatured. This level is then compared to a standard curve, to determine whether one or more variations are present.

Microfluidic Detection Apparatus

The microfluidic apparatus of the invention often, though not necessarily, comprise a substrate in which fluidic reagents, mixtures of reagents, reactants, products or the like are mixed and analyzed. A wide variety of suitable substrates for use in the devices of the invention are described in U.S. Pat. No. 6,046,056. A microfluidic substrate holder is optionally incorporated into the devices of the invention for holding and/or moving the substrate during an assay. The substrate holder optionally includes a substrate viewing region for analysis of reactions carried out on the substrate. An analyte detector mounted proximal to the substrate viewing region to detect formation of products and/or passage of reactants along a portion of the substrate is provided. A computer, operably linked to the analyte detector, monitors formation of reactants, separation of sequencing products, or the like. An electrokinetic component typically provides for movement of the fluids on the substrate. Microfluidic devices are also described in U.S. Pat. No. 6,399,023.

A principal component of nucleic acid analysis is molecular partition. Channels in microfluidic substrates can be used for molecular separations. In addition, the dexterous fluidics in the microfluidic devices herein produce exquisite control over injection volume—a principal parameter determining resolution in molecular partitioning. Aside from biochemistry and analytical capabilities in microdevices, systems that automate access to reagents and specimens are highly useful for the integrated systems herein. In high throughput pharmaceutical screening a "world-to-chip" interface capable of importing samples from conventional liquid vessels (such as test tubes or 384-well plates), or from solid dots of reagent on substrates is useful. The ability to import 1000's of different samples with inter-sample intervals as short as 5 seconds is achieved using the systems herein. A simple system will perform experiments at the rate of 10,000 experiments per channel per day. Simple parallelization of the channels produces a capacity of more than 1 million such assays per instrument-day.

Accordingly, in one embodiment, a "sipping" strategy for introducing solubilized reagents or samples into a microfluidic substrate from a standard microplate is used. This is adapted to elements of nucleic acids testing, for example to allow for random access to a library of probes or primers. Although this technology works, the advantage of reagent economy that is a hallmark of the microfluidic technology is somewhat nullified when a chemical library must be presented to the system in tens of microliter volumes, e.g., in microplates.

In order to take advantage of the very small quantities of reagents required by the chip, and to make a system scalable to millions of experiments, a solid phase reagent interface uniquely suited to high throughput LabChip processing is desirable. Several new interfaces that make use of reagents dried in microarrays on a solid surface are described herein. These configurations are suited to the needs of diagnostic products in which elements need to be standardized, convenient, and have acceptable shelf-life. Many robotic systems are now available that can deposit arrays of individual solutions at high densities (1000 per square centimeter and greater). These are typically used as capture elements in heterogeneous phase biochemical assays such as nucleic acids hybridization. The same approach can be used to deposit elements of solution phase reactions (PCR primers, probes, sequencing primers, etc.). Using these approaches, systems that access solid phase reagents at densities of up to 1000 spots per square centimeter are made.

As described above, a preferred integrated method of the invention incorporates the use of pre-synthesized sets of primers for sequencing and/or PCR, and or reagents to be tested in drug screening assays. A device of the invention preferably includes a primer storage and/or primer transport mechanism for delivering selected primers to a reaction channel in the microfluidic device. Exemplary storage mechanisms optionally include components adapted to holding primers in a liquid or lyophilized form, including containers, containers with separate compartments, plates with wells (e.g., small microtiter plates with hundreds or thousands of wells) membranes, matrices, arrays of polymers, or the like. Additional embodiments for handling dried reagents on solid substrates are shown below.

As discussed above, the region for storage of the primers is optionally located on the substrate of the microfluidic device in fluid connection to a mixing region or channel on the substrate in which a biochemical reaction (PCR, sequencing or the like) is carried out. In an alternative embodiment, the primer storage area is physically separated from the substrate. In this embodiment, the primers can be loaded onto the substrate, either manually, or using an automated system. For example, a Zymate XP (Zymark Corporation; Hopkinton, Mass.) automated robot using a Microlab 2200 (Hamilton; Reno, Nev.) pipetting station can be used to transfer parallel samples to regularly spaced wells in a manner similar to transfer of samples to microtiter plates. If the primers are stored in lyophilized form (e.g., dried on a substrate), a portion of the lyophilized primer is typically suspended in an aqueous solution to facilitate transfer to a microfluidic substrate. An electropipettor as described above can be used to select and transport samples to a microfluidic substrate from a well plate, or from any region of a microfluidic substrate. Because integration of the electropipettor with the microfluidic substrates of the invention is relatively simple, electropipettor embodiments are preferred.

In preferred embodiments including an electropipettor, a variety of storage systems for storing reagents, such as primers for delivery to the microfluidic devices of the invention, are applicable. Compounds are conveniently sampled with the electropipettor from well plates, or from immobilized samples stored on a matrix (e.g., a porous, hydrophilic, or hydrophobic matrix), or from dried samples stored on a substrate such as a nitrocellulose, nylon or nytran membrane. In embodiments where the samples are dried, the samples are solubilized using the electropipettor, which can be operated to expel a small volume of fluid onto the dried reagent, followed by pipetting the expelled fluid comprising the reagent into the electropipettor. See also, U.S. Pat. No. 5,779,868.

Accordingly, the present invention provides sampling systems which provide the compounds to be sampled in an immobilized format on a membrane matrix or the like, i.e., that the sample material is provided in a fixed position, either by incorporation within a fixed matrix, e.g., a porous matrix, a charged matrix, a hydrophobic or hydrophilic matrix, or the like, which maintains the sample in a given location. Alternatively, such immobilized samples include samples spotted and dried upon a given sample matrix. In preferred aspects, the compounds to be screened are provided on a sample matrix in dried form. Typically, such sample matrices will include any of a number of materials that can be used in the spotting or immobilization of materials, including, e.g., membranes, such as cellulose, nitrocellulose, PVDF, nylon, polysulfone and the like. Typically, flexible sample matrices are preferred, to permit folding or rolling of the sample matrices which have large numbers of different sample compounds immobilized thereon, for easy storage and handling.

Generally, samples are optionally applied to the sample matrix by any of a number of well known methods. For example, sample libraries are spotted on sheets of a sample matrix using robotic pipetting systems which allow for spotting of large numbers of compounds. Alternatively, the sample matrix is treated to provide predefined areas for sample localization, e.g., indented wells, or hydrophilic regions surrounded by hydrophobic barriers, or hydrophobic regions surrounded by hydrophilic barriers (e.g., where samples are originally in a hydrophobic solution), where spotted materials will be retained during the drying process. Such treatments then allow the use of more advanced sample application methods, such as those described in U.S. Pat. No. 5,474,796, wherein a piezoelectric pump and nozzle system is used to direct liquid samples to a surface. Generally, however, the methods described in the '796 patent are concerned with the application of liquid samples on a surface for subsequent reaction with additional liquid samples. However, these methods are readily modified to provide dry spotted samples on a substrate. Similarly, the use of inkjet printing technology to print biological and chemical reagents onto substrates is well developed. See, e.g., Wallace (1996) *Laboratory Automation News* 1(5):6–9 where ink-jet based fluid microdispensing for biochemical applications is described.

Similarly, cleavable linkers attaching compounds to an array can be used to store the compounds in an array, followed by cleavage from the array. A variety of cleavable linkers, including acid cleavable linkers, light or "photo" cleavable linkers and the like are known in the art. Exemplar arrays are described in Pirrung et al., U.S. Pat. No. 5,143,854 (see also, PCT Application No. WO 90/15070), Fodor et al., PCT Publication No. WO 92/10092 Fodor et al. (1991) *Science*, 251: 767–777; Sheldon et al. (1993) Clinical Chemistry 39(4): 718–719; Kozal et al. (1996) *Nature Medicine* 2(7): 753–759 and Hubbell U.S. Pat. No. 5,571,639. Immobilization of assay components in an array is typically be via a cleavable linker group, e.g., a photolabile, acid or base labile linker group. Accordingly, the assay component is typically released from the assay e.g., by exposure to a releasing agent such as light, acid, base or the like prior to flowing the test compound down the reaction channel. Typically, linking groups are used to attach polymers or other assay components during the synthesis of the arrays. Thus, preferred linkers operate well under organic and/or aqueous conditions, but cleave readily under specific cleavage conditions. The linker is optionally provided with a spacer having active cleavable sites. In the particular case of oligonucleotides, for example, the spacer is selected from a variety of molecules which can be used in organic environments associated with synthesis as well as aqueous environments, e.g., associated with nucleic acid binding studies. Examples of suitable spacers are polyethyleneglycols, dicarboxylic acids, polyamines and alkylenes, substituted with, for example, methoxy and ethoxy groups. Linking groups which facilitate polymer synthesis on solid supports and which provide other advantageous properties for biological assays are known. In some embodiments, the linker provides for a cleavable function by way of, for example, exposure to an acid or base.

Additionally, the linkers optionally have an active site on one end opposite the attachment of the linker to a solid substrate in the array. The active sites are optionally protected during polymer synthesis using protecting groups. Among a wide variety of protecting groups which are useful are nitroveratryl (NVOC) α-methylnitroveratryl (Menvoc), allyloxycarbonyl (ALLOC), fluorenylmethoxycarbonyl (FMOC), α-methylnitro-piperonyloxycarbonyl (MeNPOC), —NH-FMOC groups, t-butyl esters, t-butyl ethers, and the like. Various exemplary protecting groups are described in, for example, Atherton et al., (1989) *Solid Phase Peptide Synthesis,* IRL Press, and Greene, et al. (1991) *Protective Groups In Organic Chemistry,* 2nd Ed., John Wiley & Sons, New York, N.Y.

Other immobilization or spotting methods are similarly employed. For example, where samples are stable in liquid form, sample matrices can include a porous layer, gel or other polymer material which retain a liquid sample without allowing excess diffusion, evaporation or the like, but permit withdrawal of at least a portion of the sample material, as desired. In order to draw a sample into an electropipettor, the pipettor will free a portion of the sample from the matrix, e.g., by dissolving the matrix, ion exchange, dilution of the sample, and the like.

Whether the storage substrate is a filter, membrane, microtiter plate or other material holding reagents of interest, the substrate can conveniently be moved using a mechanical armature. Typically, the spatial location (or "physical address") of the reagents on the substrate are known. The armature moves the substrate relative to the microfluidic substrate (and electropipettor, where applicable) so that the component for transferring reagent from the substrate to the channels and wells of a microfluidic substrate (e.g., an electropipettor) contacts the desired reagent. Alternatively, the microfluidic substrate or electropipettor can be moved by an armature relative to the storage substrate to achieve the same effect. Similarly, both the storage substrate and the microfluidic substrate can be moved by the mechanical armature to achieve the same effect. In another aspect, the microfluidic substrate, storage substrate or transferring component (e.g., electropipettor) can be manually manipulated by the operator.

A variety of electropipettors, including "resolubilization" pipettors for solubilizing dried reagents for introduction into microfluidic apparatus are described in U.S. Pat. No. 5,779, 868, supra. In brief, an electropipettor pipettor having separate channels is fluidly connected to an assay portion of the microfluidic device (i.e., a microfluidic substrate having the reaction and/or analysis and/or separation channels, wells or the like). In one typical embodiment, the electropipettor has a tip fluidly connected to a channel under electroosmotic control. The tip optionally includes features to assist in sample transfer, such as a recessed region to aid in dissolving samples. Fluid can be forced into or out of the channel, and thus the tip, depending on the application of current to the channel. Generally, electropipettors utilize electrokinetic or "electroosmotic" material transport as described herein, to alternately sample a number of test compounds, or "subject materials," and spacer compounds. The pipettor then typically delivers individual, physically isolated sample or test compound volumes in subject material regions, in series, into the sample channel for subsequent manipulation within the device. Individual samples are typically separated by a spacer region of low ionic strength spacer fluid. These low ionic strength spacer regions have higher voltage drop over their length than do the higher ionic strength subject material or test compound regions, thereby driving the electrokmetic pumping, and preventing electrophoretic bias. On either side of the test compound or subject material region, which is typically in higher ionic strength solution, are fluid regions referred to as first spacer regions (also referred to as high salt regions or "guard bands"), that contact the interface of the subject material regions. These first spacer regions typically comprise a high ionic strength solution to prevent migration of the sample elements into the lower ionic strength fluid regions, or second spacer region, which would result in electrophoretic bias. The use of such first and second spacer regions is described in greater detail in U.S. Pat. No. 5,779,868, supra. Spacers are not, however, required, particularly in those embodiments where transported components such as primers have the same charge and mass. It will be appreciated that embodiments using identically (or nearly identically) sized primers, such as modular primers, can be used without guard bands.

Figure 6A:
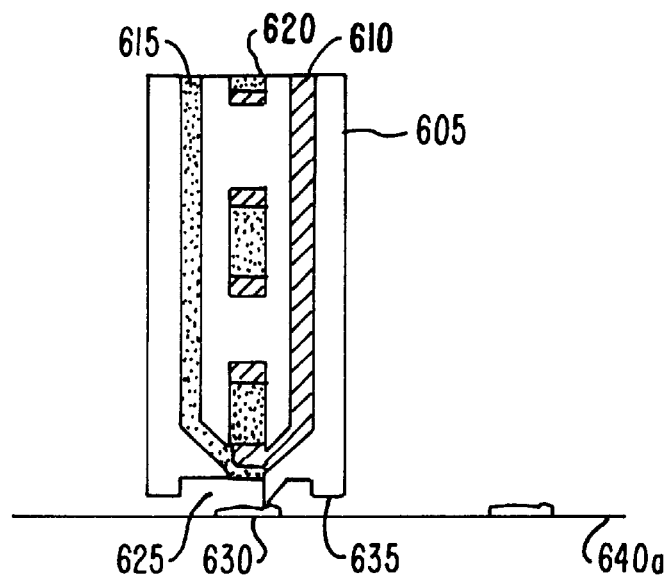
FIGS. 6A–6B depict alternate technologies for flowing dried reagents from a substrate into a microfluidic apparatus; 6A depicts an electropipettor with a cup region; 6B depicts an electrokinetic interface which spans a membrane having the dried reagents.
Figure 6B:
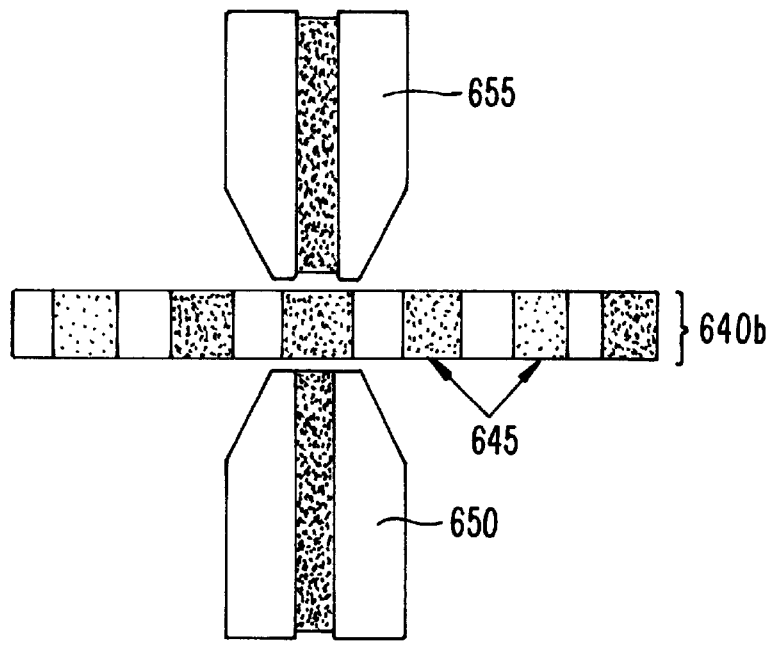

In FIG. 6A and FIG. 6B, two solid phase samplers are shown, depicting two approaches for accessing dried reagent arrays by microfluidic apparatus. FIG. 6A shows micromachined chip 605 having three capillary channels 610, 615, and 620. The channels terminate at one end of chip 605 in sample cup 625. Due to the differences in ionic strength of the solution in channels 610, 615, and 620, application of a potential from channel 610 to the channel 620, will force fluid into sample cup 625 where it can dissolve dried reagent 630. Subsequent application of a potential from right channel 610 to central channel 620 will draw solubilized reagent 635 into central channel 620. In FIG. 6B, porous substrate (e.g. microchannel alumina) 640 contains dried reagents 645. Application of a sufficient voltage from bottom solvent-supply capillary 650 to chip capillary 655 attached to a microfluidic element (e.g., a channel on a chip; not shown) causes fluid to pass through porous substrate 640 and into capillary 655 attached to the microfluidic element. In passing through substrate 640, the fluid dissolves dried reagent 645 and then carries it into the microfluidic element. In both systems, substrate 640 is moved, e.g., by robot to position the sampling capillary over the appropriate reagent site.

Alternatively, in embodiments omitting an electropipettor, the channels are. individually fluidly connected to a plurality of separate reservoirs via separate channels. The separate reservoirs each contain a separate test analyte with additional reservoirs being provided for appropriate spacer compounds. The test compounds and/or spacer compounds are transported from the various reservoirs into the sample channels using appropriate fluid direction schemes. In either case, it generally is desirable to separate the discrete sample volumes, or test compounds, with appropriate spacer regions.

One of skill will immediately recognize that any, or all of the components of a microfluidic device of the invention are optionally manufactured in separable modular units, and assembled to form an apparatus of the invention. See also, U.S. Pat. No. 6,399,023, supra. In particular, a wide variety of substrates having different channels, wells and the like are typically manufactured to fit interchangeably into the substrate holder, so that a single apparatus can accommodate, or include, many different substrates adapted to control a particular reaction. Similarly, computers, analyte detectors and substrate holders are optionally manufactured in a single unit, or in separate modules which are assembled to form an apparatus for manipulating and monitoring a substrate. In particular, a computer does not have to be physically associated with the rest of the apparatus to be "operably linked" to the apparatus. A computer is operably linked when data is delivered from other components of the apparatus to the computer. One of skill will recognize that operable linkage can easily be achieved using either electrically conductive cable coupled directly to the computer (e.g., parallel, serial or modem cables), or using data recorders which store data to computer readable media (typically magnetic or optical storage media such as computer disks and diskettes, CDs, magnetic tapes, but also optionally including physical media such as punch cards, vinyl media or the like).

Microfluidic Substrates and Electrokinetic Modulators

Suitable microfluidic substrate materials are generally selected based upon their compatibility with the conditions present in the particular operation to be performed by the device. Such conditions can include extremes of pH, temperature, salt concentration, and application of electrical fields. Additionally, substrate materials are also selected for their inertness to critical components of an analysis or synthesis to be carried out by the device.

Examples of useful substrate materials include, e.g., glass, quartz and silicon as well as polymeric substrates, e.g. plastics. In the case of conductive or semi-conductive substrates, it is occasionally desirable to include an insulating layer on the substrate. This is particularly important where the device incorporates electrical elements, e.g., electrical fluid direction systems, sensors and the like. In the case of polymeric substrates, the substrate materials are optionally rigid, semi-rigid, or non-rigid, opaque, semi-opaque or transparent, depending upon the use for which they are intended. For example, devices which include an optical, spectrographic, photographic or visual detection element, will generally be fabricated, at least in part, from transparent materials to allow, or at least, facilitate that detection. Alternatively, transparent windows of, e.g., glass or quartz, are optionally incorporated into the device for these types of detection elements. Additionally, the polymeric materials optionally have linear or branched backbones, and can be crosslinked or non-crosslinked. Examples of particularly preferred polymeric materials include, e.g., polydimethylsiloxanes (PDMS), polyurethane, polyvinylchloride (PVC) polystyrene, polysulfone, polycarbonate, PMMAs and the like.

In certain embodiments, the microfluidic substrate includes one or more microchannels for flowing reactants and products. At least one of these channels typically has a very small cross sectional dimension, e.g., in the range of from about 0.1 $\mu$m to about 500 $\mu$m. Preferably the cross-sectional dimensions of the channels is in the range of from about 1 to about 200 $\mu$m and more preferably in the range of from about 0.1 to about 100 $\mu$m, often in the range of about 1 to 100 $\mu$m. In particularly preferred aspects, each of the channels has at least one cross-sectional dimension in the range of from about 0.1 $\mu$m to about 100 $\mu$m. It will be appreciated that in order to maximize the use of space on a substrate, serpentine, saw tooth or other channel geometries, are optionally used to incorporate longer channels on less substrate area, e.g., to facilitate separation of reaction products or reactants. Substrates are of essentially any size, with area typical dimensions of about 1 cm$^2$ to 10 cm$^2$.

In general, the microfluidic devices will include one or more chambers, channels or the like, fluidly connected to allow transport of fluid among the chambers and/or channels of these devices. By "microfluidic" is generally meant fluid systems, e.g., channels, chambers and the like, typically fabricated into a solid typically planar substrate, and wherein these fluid elements have at least one cross-sectional dimension in the range of from about 0.1 to about 500 $\mu$m. Typically, the cross sectional dimensions of the fluid elements will range from about 1 $\mu$m to about 200 $\mu$m.

The term "channel" is defined above. A "chamber" will typically, though not necessarily, have a greater volume than a channel, typically resulting from an increased cross-section having at least one dimension from about 10 to about 500 $\mu$m, although, as for channels, the range can span, e.g., 0.1 to about 500 $\mu$m. Although generally described in terms of channels and chambers, it will generally be understood that these structural elements are interchangeable, and the terms are used primarily for ease of discussion. By "fluidly connected" is meant a junction between two regions, e.g., chambers, channels, wells etc., through which fluid freely passes. Such junctions may include ports or channels, which can be clear, i.e., unobstructed, or can optionally include valves, filters, and the like, provided that fluid freely passes through the junction when desired.

Manufacturing of these microscale elements into the surface of the substrates is generally carried out by any number of microfabrication techniques that are known in the art. For example, lithographic techniques are employed in fabricating, e.g., glass, quartz or silicon substrates, using methods well known in the semiconductor manufacturing industries such as photolithographic etching, plasma etching or wet chemical etching. See, Sorab K. Ghandi, VLSI Principles: Silicon and Gallium Arsenide, N.Y., Wiley (see, esp. Chapter 10). Alternatively, micromachining methods such as laser drilling, air abrasion, micromilling and the like are employed. Similarly, for polymeric substrates, well known manufacturing techniques are used. These techniques include injection molding or stamp molding methods where large numbers of substrates are produced using, e.g., rolling stamps to produce large sheets of microscale substrates or polymer microcasting techniques where the substrate is polymerized within a micromachined mold. Polymeric substrates are further described in U.S. Pat. No. 5,885,470.

In addition to micromachining methods, printing methods are also used to fabricate chambers channels and other microfluidic elements on a solid substrate. Such methods are taught in detail in U.S. Pat. No. 6,074,725. In brief, printing methods such as ink-jet printing, laser printing or other printing methods are used to print the outlines of a microfluidic element on a substrate, and a cover layer is fixed over the printed outline to provide a closed microfluidic element.

The substrates will typically include an additional planar element which overlays the channeled portion of the substrate, enclosing and fluidly sealing the various channels. Attaching the planar cover element is achieved by a variety of means, including, e.g., thermal bonding, adhesives or, in the case of certain substrates, e.g., glass, or semi-rigid and non-rigid polymeric substrates, a natural adhesion between the two components. The planar cover element can additionally be provided with access ports and/or reservoirs for introducing the various fluid elements needed for a particular screen, and for introducing electrodes for electrokinetic movement.

Typically, an individual microfluidic device will have an overall size that is fairly small. Generally, the devices will have a square or rectangular shape, but the specific shape of the device can be easily varied to accommodate the users needs. While the size of the device is generally dictated by the number of operations performed within a single device, such devices will typically be from about 1 to about 20 cm across, and from about 0.01 to about 1.0 cm thick.

Serial to Parallel Conversion

In performing a large number of parallel fluid manipulations, it is often necessary to allocate a single fluid volume among several separate channels or chambers for reaction of analysis. For example, a single sample volume is introduced into a device along a single channel. To perform a panel of desired screens on the sample, or perform the same screen multiple times, it is necessary to direct portions of the sample to separate reaction chambers or channels. Similarly, a series of discrete and different sample volumes is individually directed from the sample introduction channel into multiple separate channels. This allocation or direction of a single fluid volume or multiple discrete fluid volumes from a serial orientation, i.e., a single channel or chamber, to a parallel orientation, i.e., to multiple separate channels or chambers, is termed "serial to parallel conversion." This conversion is particularly applicable to the present invention, in which multiple assays can be run in parallel in a first assay screen, the results detected (in serial or parallel) and a second series of parallel assays selected for a second screen based upon the results of the first screen.

As applied to the present invention, methods of performing fluidic operations that include a plurality of parallel fluid manipulations to provide parallel fluidic analysis of sample materials is therefore provided, as are related apparatus. In the methods a microfluidic device is provided. The device has at least a first transverse reagent introduction channel fluidly connected to a source of at least one reagent and a source of at least one sample material. The transverse channel is fluidly connected to a plurality of parallel reagent reaction channels. A first reagent or mixture of reagents is selected from the source of at least one reagent, and the first reagent is transported through the reagent introduction channel and a portion of the reagent is aliqouted as described into at least one parallel reagent reaction channel (typically into several parallel reaction chambers or channels). A first sample material is selected from the source of at least one sample material and the first sample material is aliquoted into at least a first of the plurality of parallel reagent reaction channels. At least one additional sample material, or at least one additional reagent is selected, and the additional sample material or additional reagent is aliquoted into at least a second of the plurality of parallel reagent reaction channels. The first sample material and the first reagent are contacted in the first reagent reaction channels, causing a reaction of the first sample material and the first reagent. The at least one additional sample material or at least one additional reagent is contacted with one or more fluid component such as the first sample material, the first reagent, at least one additional reagent, at least one additional sample material, a second additional reagent, a second additional sample material or the like. The first reaction product of the first sample material and the first reagent is detected, as is a second reaction product of at least one additional sample material or at least one additional reagent and one or more fluid component (i.e., from two parallel reactions in two or more parallel reaction channels). Based upon the first or second reaction product, a secondary reagent and a secondary sample material are selected and the process repeated on these secondary components. It will be appreciated that this "parallelization" of multiple assays and selection of additional assays based upon the results of a first series of assays can dramatically speed selection and performance of related assays, e.g., in a drug screening, assay optimization, diagnostic or nucleic acid sequencing context.

In one aspect, the method comprises parallel analysis of a plurality of sample materials in the parallel channels, in which multiple reagents are mixed in a plurality of the parallel channels with multiple sample materials to form a multiple of products, and, based upon detection of the multiple products, selecting the secondary sample material and secondary reagent. This multiply parallel format can additionally speed assay development and data acquisition. In one aspect, the microfluidic device includes the first transverse reagent introduction channel and at least a second transverse channel, and a plurality of parallel channels intersecting both of the first and second transverse channels. In this format, the step of aliquoting the portion of the reagent into at least one parallel reagent reaction channel is performed by applying a first voltage across the first transverse reagent introduction channel and the second transverse channel to draw the portion of the reagent into the first transverse reagent introduction channel, whereby the portion of the reagent is present at intersections of the first channel and each of the plurality of parallel channels; and, applying a second voltage from the first transverse channel to the second transverse channel, whereby a current in each of the parallel channels is equivalent, and whereby the portion of the reagent at the intersections of the first transverse channel and each of the plurality of parallel channels is moved in to each of the plurality of parallel channels.

In a second serial to parallel conversion aspect, methods of performing a plurality of separate assays on a single sample are provided. In these methods a microfluidic device having at least a first transverse channel fluidly connected to at least a source of the sample, a plurality of separate parallel channels fluidly connected to the first transverse channel, each of the separate channels having disposed therein reagents for performing a different diagnostic assay, and a fluid direction system for concurrently directing a portion of the sample into each of the plurality of parallel channels is provided. A portion of the sample is transported into each of the parallel channels, whereby the sample and the reagents disposed in the channel undergo a reaction. A result of the reaction of the sample and the reagents disposed in the channel, for each of the parallel channels is detected.

Thus, in certain aspects, the devices and systems of the present invention generally include novel substrate channel designs to ensure flow of appropriate amounts of fluids in parallel channels, and thereby facilitate serial to parallel conversion of fluids in these microfluidic devices.

Serial to parallel conversion of fluids within a microfluidic device is important for a number of reasons. For example, where one is performing a number of separate analyses on a single sample, serial to parallel conversion can be used to aliquot the single sample among a number of separate assay channels in a microfluidic device. Alternatively, a number of physically discrete and different samples, e.g., drug candidates, diagnostic samples, or the like, are serially introduced into a single device and allocated among a number of different parallel channels subjecting the samples to the same or different analyses.

Figure 7A:
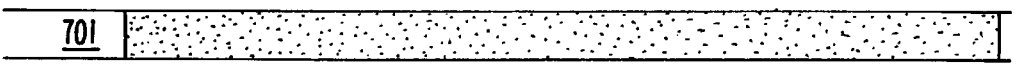
FIGS. 7A–7D depict serial to parallel conversion strategies.
Figure 7A:
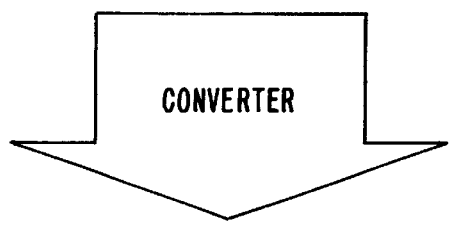
Figure 7A:
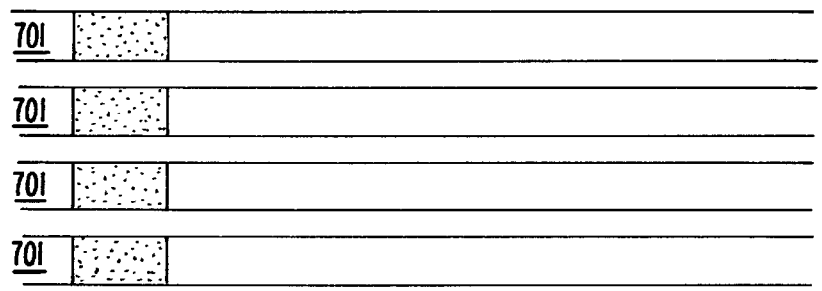
Figure 7B:
Figure 7B:
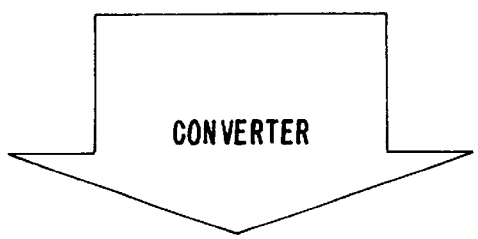
Figure 7B:
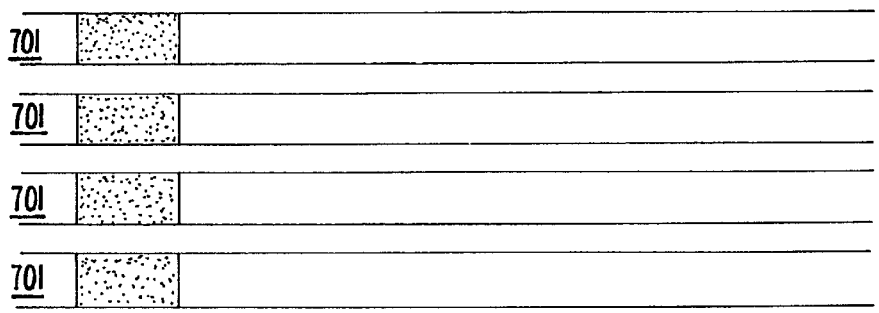
Figure 7C:
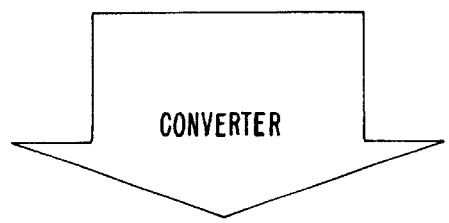
Figure 7D:
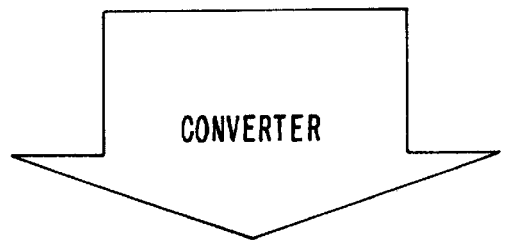

Schematic illustrations of serial to parallel conversions are shown in FIGS. 7A–7D. For example, in FIG. 7A, a single sample fluid region (701) is shown being converted to a plurality of separate aliquots of the sample fluid, in a series of parallel channels. Alternatively, as shown in FIG. 7B, separate aliquots of the same sample fluid, provided in a serial orientation in a single channel are allocated to each of several separate parallel channels. In a particularly useful aspect, as shown in FIG. 7C, a plurality of different compounds (701, 702, 703 and 704) are serially introduced into a microfluidic channel (top) and then are each redirected to a separate parallel channel for separate analysis or further manipulation. FIG. 7D also illustrates a particularly useful application of serial to parallel conversion where a plurality of different samples (701, 702, 703 and 704) are serially introduced into a microfluidic channel, and are allocated and redirected among a number of parallel channels, wherein each parallel channel contains a portion of each of the samples and reflects the serial orientation originally presented (bottom). Thus, serial to parallel conversion is also applicable to performing fluidic operations which require large numbers of iterative or successive fluid manipulations, i.e., as in high throughput analysis of samples where a plurality of different samples (e.g., 701, 702, 703 and 704) are subjected to a plurality of different analyses (e.g., in each separate parallel channel). Specifically, separate channels each perform, in parallel, fluidic operations which separately require iterative and/or successive fluid manipulations.

Figure 8:
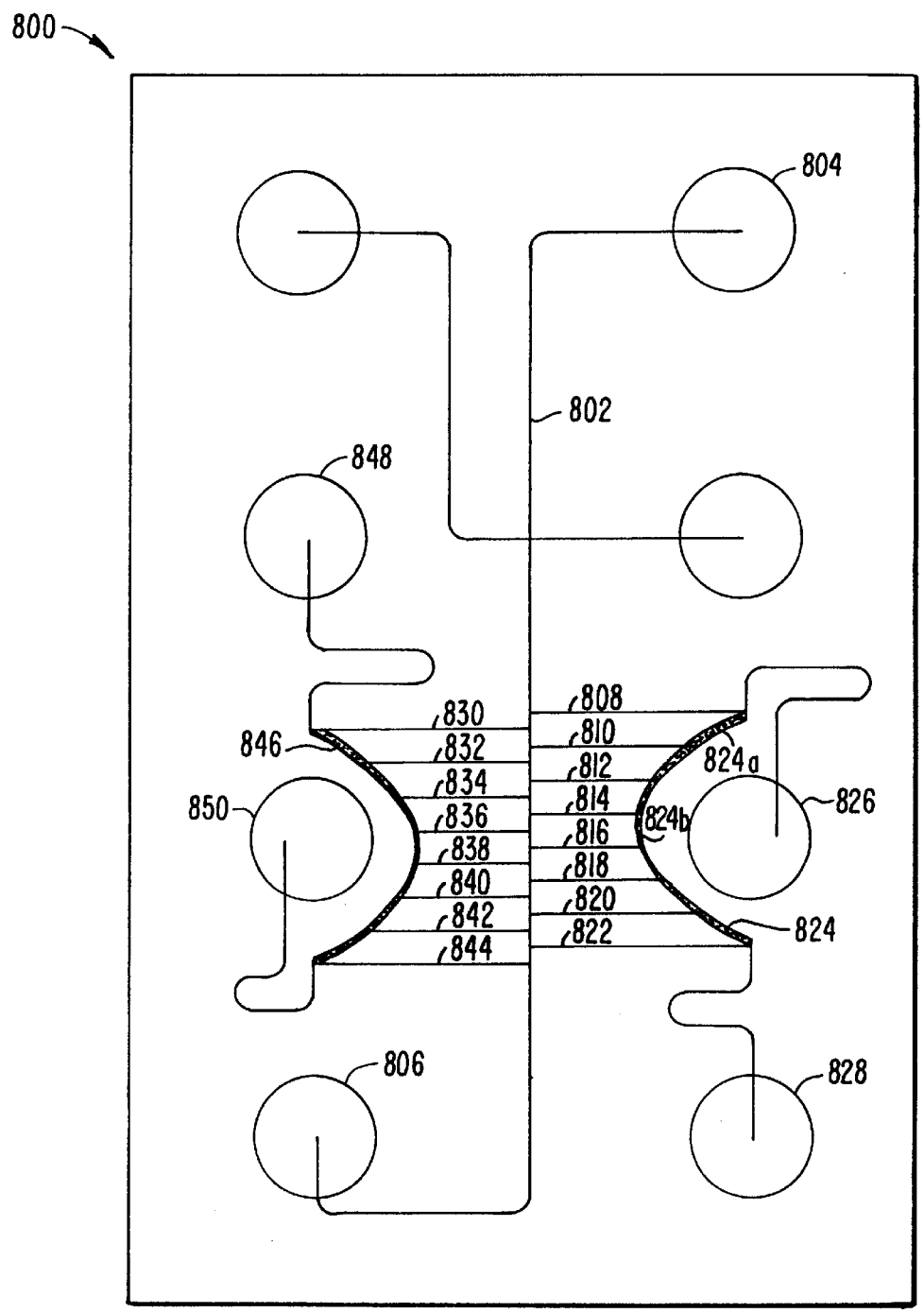
FIG. 8 depicts a top view of a serial to parallel converter.
Figure 9:
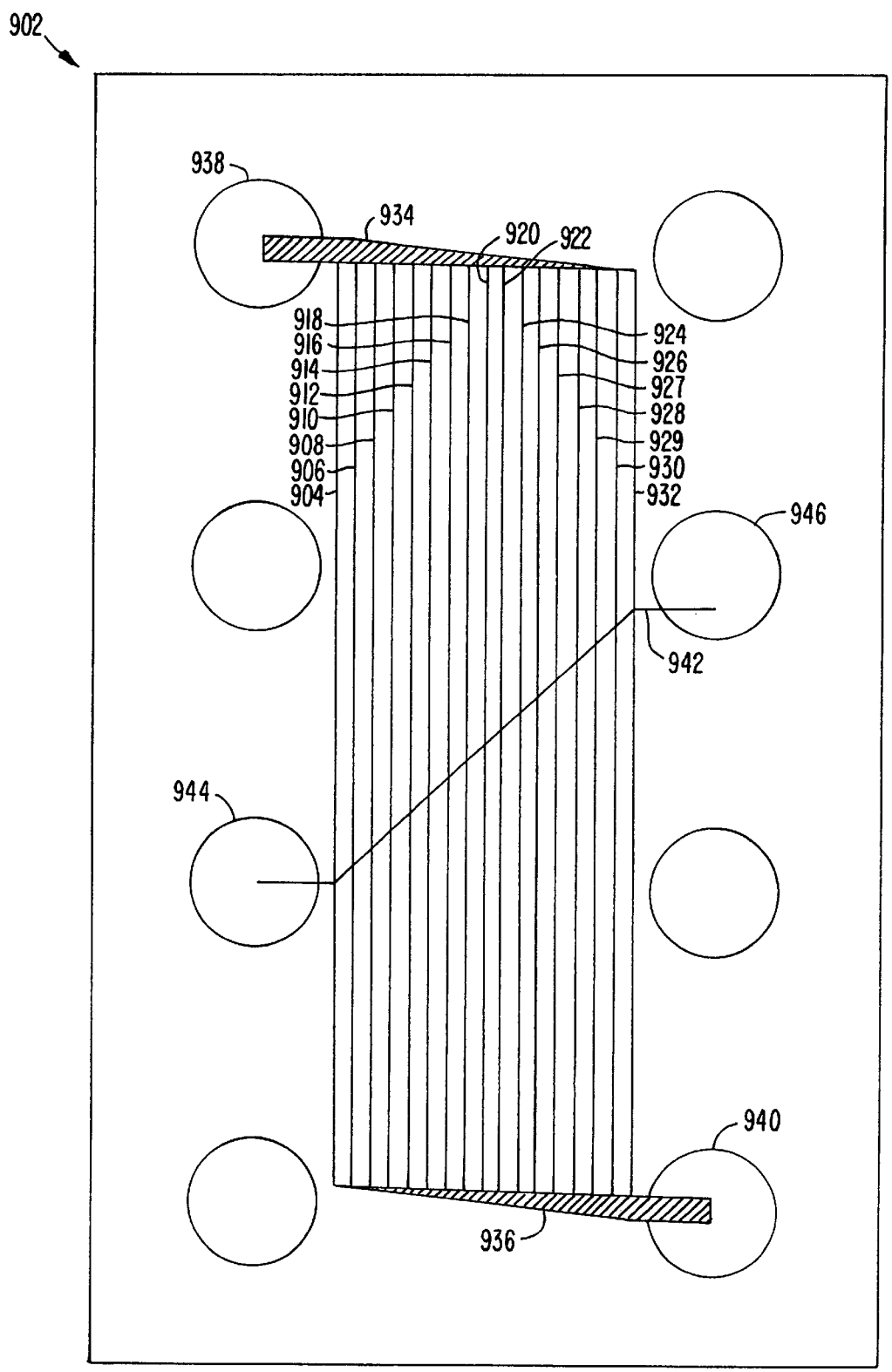
FIG. 9 depicts a top view of a serial to parallel converter.
Figure 10:
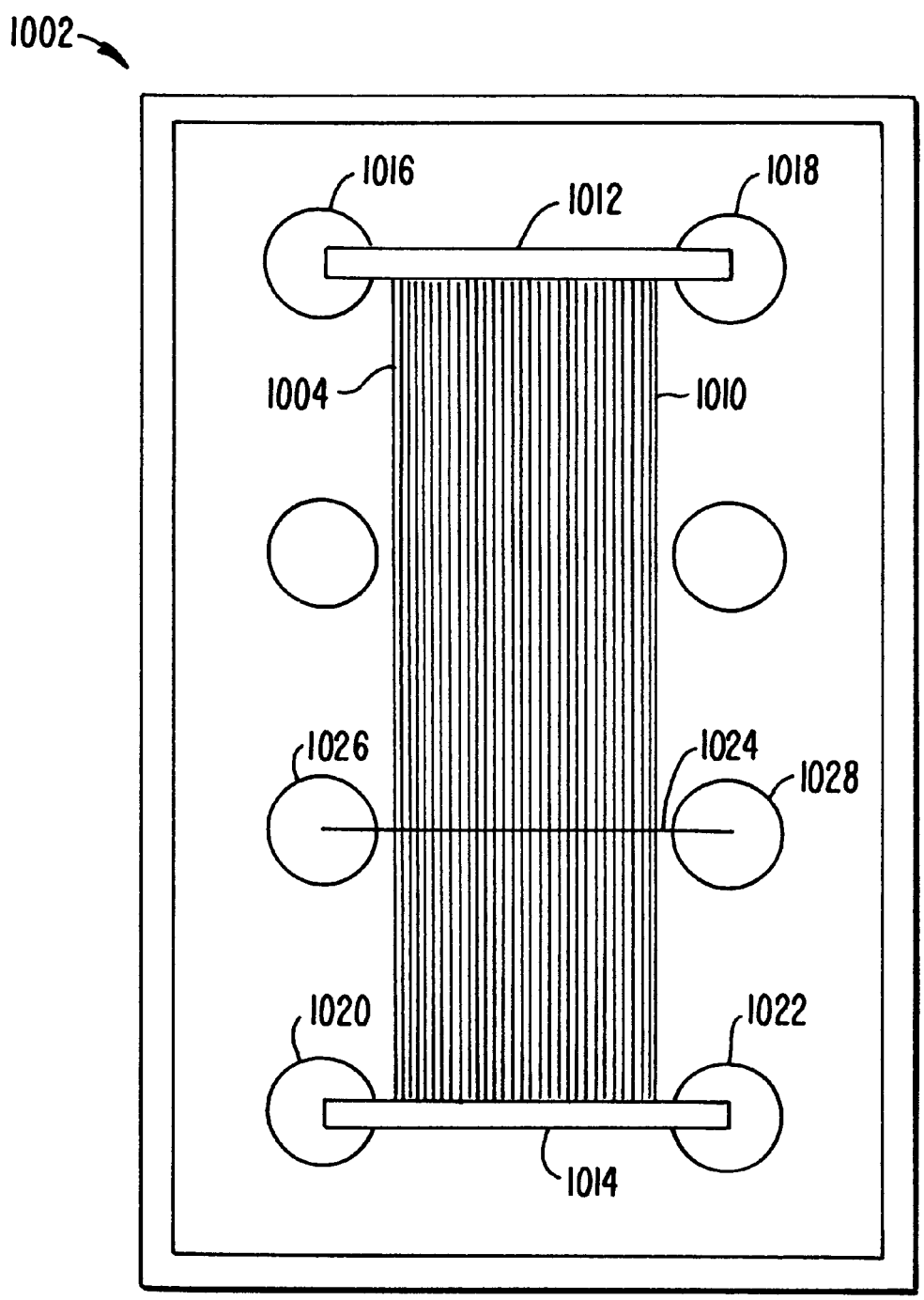
FIG. 10 depicts a top view of a serial to parallel converter.

While serial to parallel conversion is an important aspect of fluid control in microfluidic systems, it does present difficulties from a control aspect. For example, fluid flow in electroosmotic systems is controlled by and therefore related to current flow between electrodes. Furthermore, resistance in the fluid channels varies as a function of path length and width, and thus, different length channels will have different resistances. If this differential in resistance is not corrected, it can result in the creation of transverse electrical fields which can inhibit the ability of the devices to direct fluid flow to particular regions within these devices. Specifically, the current, and thus the fluid flow will follow the path of least resistance, e.g., the shortest path. While this problem of transverse electrical fields is optionally alleviated through the use of separate electrical systems, i.e., electrodes, at the termini of each and every parallel channel, production of devices incorporating all of these electrodes, and control systems for controlling the electrical potential applied at each of these electrodes are complex, particularly where one is dealing with hundreds to thousands of parallel channels in a single small scale device, e.g., 1–2 cm$^2$. Accordingly, the present invention provides microfluidic devices for affecting serial to parallel conversion, by ensuring that current flow through each of a plurality of parallel channels is at an appropriate level to ensure a desired flow pattern through those channels or channel networks. FIGS. 8, 9 and 10 illustrate a number of methods and substrate/channel designs for accomplishing these goals.

In a first embodiment, FIG. 8 illustrates a substrate 800, employing a channel orientation that is optionally used to accomplish serial to parallel conversion or equal fluid flow in parallel channels. The substrate includes main channel 802, which includes electrodes disposed in each of ports 804 and 806, at the termini of channel 802. A series of parallel channels 808–822 and 830–844 terminate in main channel 802. The opposite termini of these parallel channels are connected to parabolic channels 824 and 846, respectively. Electrodes are disposed in ports 826, 828, 848 and 850, which are included at the termini of these parabolic channels, respectively.

In operation, a volume of fluid is transported along main channel 802 by applying a potential across electrodes 804 and 806. An equal voltage is applied across electrodes 826 and 828, and 848 and 850, resulting in a net zero flow through the parallel channels. The sample is optionally present within main channel 802 as a long slug of a single sample, or multiple slugs of a single or multiple samples. Once the sample fluid or fluids reach the intersection of the main channel with the parallel channels, e.g., 830–844, it is then pumped through the parallel channels by applying a potential across electrode sets 826:828 and 848:850, which results in a fluid flow from parallel channels 808–822, to force the samples into parallel channels 830–844. The current flow in each of the parallel channels 808–822 and 830–844 is maintained constant or equivalent, by adjusting the length of the parallel channels, resulting in a parabolic channel structure connecting each of the parallel channels to its respective electrodes. The voltage drop within the parabolic channel between the parallel channels is maintained constant by adjusting the channel width to accommodate variations in the channel current resulting from the parallel current paths created by these parallel channels. For example, channel segment 824a, while longer than channel segment 824b, has the same resistance, because segment 824a is appropriately wider. Thus, the parabolic design of channels 824 and 846, in combination with their tapering structures, results in the resistance along all of the parallel channels being equal, resulting in an equal fluid flow, regardless of the path chosen. Generally, determining the dimensions of channels to ensure that the resistances among the channels are controlled as desired, is optionally carried out by well known methods, and generally depends upon factors such as the make-up of the fluids being moved through the substrates.

In another example, FIG. 9 illustrates how the principles of the present invention can be used in a substrate design that employs fewer electrodes to affect parallel fluid flow. In particular, fluid flow within an array of parallel channels is controlled by a single pair of electrodes. As shown, substrate 902 includes a plurality of parallel channels 904–932. These parallel channels each terminate in transverse channels 934 and 936. Transverse channel 934 has a tapered width, going from its widest at the point where it intersects the nearest parallel channel 904 to the narrowest at the point it intersects the most distant parallel channel 932. Transverse channel 936, on the other hand, goes from its widest at the point it intersects parallel channel 932, to the narrowest where it intersects parallel channel 902. Electrodes are included in the ports 938 and 940 at the wide termini of transverse channels 934 and 936, respectively. The dimensions of these tapered channels are such that the current flow within each of the parallel channels is equal, thereby permitting equal flow rates in each channel. As shown, transverse or sample introduction channel 942 is oriented so that it crosses each parallel channel at the same point relative to one or the other electrode, to ensure that the potential at the intersections of transverse channel 942 and all of the parallel channels 904–932 is the same, again, to prevent the formation of transverse electrical fields, or "shorting out" the array of channels. This results in the sample introduction channel 942 being disposed across the parallel channels at a non-perpendicular angle, as shown.

In operation, a sample fluid, e.g., disposed in port 944, is flowed through transverse channel 942, and across the intersection of the parallel channels 904–932 by applying a potential across ports 944 and 946. Once the sample is disposed across the one or more desired parallel channels, e.g., as dictated by the serial to parallel conversion desired (see, FIGS. 7A–7D), a potential is then applied across ports 938 and 940, resulting in an equal fluid flow through each of the parallel channels and injection of the sample fluid into each of the desired parallel channels.

FIG. 10 illustrates still another embodiment for practicing the principles set forth herein. In this embodiment, a substrate includes a large number of parallel channels. For ease of discussion, these channels are referred to herein as parallel channels 1004–1010, although it should be understood that preferred aspects will include upwards of 20, 50, 100, 500 or more separate parallel channels. The parallel channels 1004–1010 terminate at one end in transverse channel 1012 and at the other end in transverse channel 1014. Electrodes are provided within ports 1016, and 1018, and 1020 and 1022 at the termini of these transverse channels. In this embodiment, the problems of varying current within the different parallel channels are addressed by providing transverse channels 1012 and 1014 with sufficient width that voltage variation across the length of these transverse channels, and thus, as applied to each parallel channel, is negligible, or nonexistent. Alternatively, or additionally, a single electrode is optionally disposed along the length of each of these transverse channels to ensure equal current flow at the transverse channel's intersection with each parallel channel.

As shown, however, transverse or sample introduction channel 1024 intersects each of the parallel channels, and is controlled by electrodes disposed within ports 1026 and 1028 at the termini of channel 1024. As described for FIG. 9, above, the sample introduction channel intersects each parallel channel at a point where the potential applied to each channel will be equal. In this aspect, however, the channel is arranged substantially parallel to transverse channels 1012 and 1014, as each parallel channel is subjected to the same voltages.

In operation, a sample, e.g., disposed in port 1026, is flowed through sample channel 1024, across the intersection of the various parallel channels 1004–1010, by applying a potential across ports 1026 and 1028. Once the sample fluid is in its appropriate location, i.e., across all or a select number of parallel channels, a potential is applied across ports 1016:1020 and 1018:1022, injecting a plug of sample into the parallel channels.

The efficacy of these serial to parallel conversions was tested. In brief, a solid slug of fluorescent fluid material, e.g., including fluorescein, rhodamine or the like, was injected through the diagonal transverse channel by applying a potential across the transverse channel, e.g., at electrodes 944 and 946, such that the sample fluid spanned several of the parallel channels. By applying a potential across the parallel channels, e.g., at electrodes 938 and 940, that portion of the fluid region at the intersections of the transverse channel and each of the parallel channels was pumped down the parallel channels. The sample fluid regions in each of the parallel channels was observed to flow at the same rate.

Parallel Fluid Manipulations

As described, the microfluidic systems of the present invention are also particularly useful in performing fluidic operations that require a large number of parallel fluid manipulations. Preferred systems can handle processing of raw sample components through analysis of sample nucleic acids. This includes processing of biological samples such as blood such that DNA is available for analysis, providing an autosampling system that can access external reagents or samples and import them for use with the microchip processing components, and provide assays on the microfluidic apparatus.

Two assays in the ultrahigh throughput format are particularly contemplated: (1) size measurement for microsatellite typing of on-chip amplified DNA, and single nucleotide polymorphism (SNP) genotyping of on-chip amplified DNA. In a particularly preferred aspect, these assays are run using parallel microfluidics to maximize sample processing power.

Sample Diagnostics

One example of a fluid operation that would benefit from the ability to perform rapidly large numbers of parallel manipulations is the screening of a given sample in a number o separate assays. For example a single fluid sample from a patient, e.g., blood, serum, saliva or the like, is screened against a number of separate antibodies or antigens for diagnostic testing. In a microfluidic format, this typically involves the apportioning of a single larger sample volume into numerous separate assay channels or chambers, wherein each separate chamber or channel contains reagents for performing a different diagnostic assay. For example, in antibody panel screens, each reaction chamber or channel can contain a different antibody or antigen. Such assay systems include those described in U.S. Pat. No. 5,942,443, and previously incorporated herein by reference.

Genotyping

Genetic analysis generally involves the correlation of measurable physical traits (the phenotype) with the inheritance of particular versions of genetic elements (the genotype). Genotyping of nucleic acid samples from a patient typically involves a two step process. Because of the complexity of genomic information, the first step usually involves an operation for reducing the complexity of the sample, or reducing the number of molecules in a mixture to be analyzed, into smaller but useful portions. Once the complexity of the sample is reduced, the less complex sample is then optionally assayed for a particular genotype, or "typed." This typing can be repeated upon a number of different segments or "loci" from the overall nucleic acid sample.

Reduction of sample complexity is typically carried out by biochemical methods that take a subset of the overall sample and concentrate it relative to, or purify it away from the remainder of the sample. Examples of these biochemical methods include, e.g., amplifying a specific subset of sample nucleic acids using preselected primers that flank the desired segment. Alternatively, the desired segment is pulled from the larger sample by hybridization with a predefined probe that is complementary to all or a portion of the desired segment.

Once a nucleic acid sample is pared down to a manageable complexity, the sample is typed to identify the presence or absence of a particular variation. Examples of such variations include simple sequence repeats ("SSR"), single nucleotide polymorphism ("SNP"), and small insertions or deletions. In the case of SSRS, typing typically involves a determination of the size of the sample segment, e.g., using size-based electrophoretic methods (gel exclusion), which will indicate the presence or absence of a larger species corresponding to the sample segment with or without the additional sequence elements. For SNPs and smaller insertions or deletions, typing can be carried out by sequencing of the sample segment, to identify the base substitution, addition or deletion. Such sequencing can be carried out by traditional sequencing methods or by hybridization of the target sequence to oligonucleotide arrays, e.g., as described in U.S. Pat. No. 5,445,934, which is hereby incorporated herein by reference. Alternatively, the SNP or smaller insertion or deletion can be identified by nuclease digestion of the segment followed by size-based separation of the portions of the digested segment. The pattern of fragments is then correlated with the presence or absence of a particular marker sequence.

Typically, methods currently utilized in the art in these genotyping experiments analyze each of the various different loci of the overall sample in a serial format. Specifically, the sample nucleic acid is amplified and characterized at a first locus, then at a second locus and so on. Further, such methods also typically utilize equipment that is only capable of performing a single component of the overall process, e.g., anplification, electrophoresis, sequencing, etc. As set forth above, the costs in equipment, time and space for performing these methods can be quite high, and increases substantially when a large number of samples and/or genetic loci are being screened.

According to the present invention, several if not all of the components of the overall process are integrated into a single microfluidic device. Further, multiple samples or disparate genetic loci from a single sample are analyzed within a single device, in a parallel orientation. For example, because of the miniature format of the microfluidic devices, from about 1 to about 500 different genetic loci from a single nucleic acid sample can be analyzed in parallel, within a single device.

Figure 11:
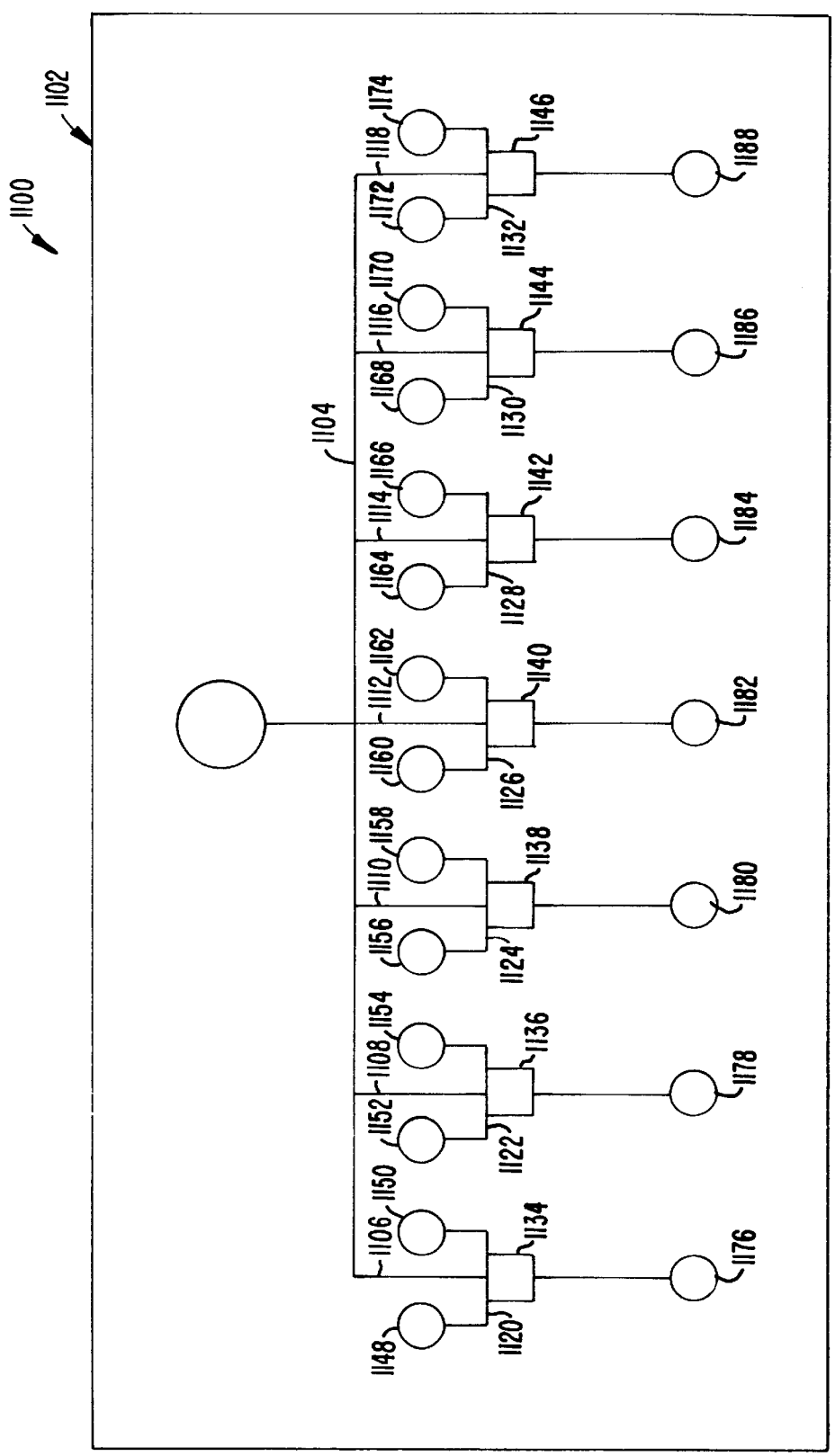
FIG. 11 depicts a top view of a serial to parallel converter.

An example of a device for carrying out analysis of multiple loci on a single nucleic acid sample is shown in FIG. 11. As shown, the device 1100, is fabricated in a solid substrate 1102. The device includes a main sample channel 1114 which is intersected by multiple parallel separation channels 1106–1118. Again, the number of these separation channels on a single device can vary depending upon the desired size of the device. As shown, each of parallel separation channels 1106–1118 is further intersected by reagent introduction channels 1120–1132, respectively, and includes reaction chambers 1134–1146, respectively. The reagent introduction channels 1120–1132 have at their termini, reservoirs 1148:1150, 1152:1154, 1156:1158, 1160:1162, 1164:1166, 1168:1170, and 1172:1174, respectively. Separation channels 1106–1118 have at their termini opposite the sample introduction channel 1104, reservoirs 1176–1188 for applying a voltage across the separation channel.

In operation, a fluid sample introduced into the sample introduction channel 1104 is aliquoted among the separate parallel separation channels 1106–1118 and delivered to reaction chambers 1134–1146, respectively. The sample is then treated according to the desired protocols by introducing into the reaction chambers reagents from the reservoirs at the termini of the reagent introduction channels. Following amplification, the target sequences are subjected to size based separation and analysis by transporting the amplified nucleic acids through the separation channels 1106–1118. Where the amplified sequence has a size that is different from the expected size of a "normal" individual it is indicative that sequence includes a sequence variation, i.e., SSR. Alternatively, the amplified sequence is sequenced by well known sequencing methods. Such sequencing methods are optionally incorporated into the devices described herein. For example, sequencing can be carried out by the Sanger method by utilizing four of the reaction chambers for incorporation of each of the four ddNTPs.

Alternative substrate designs can also be used to accomplish the goals of the device shown. In particular, as described in reference to serial to parallel conversion, above, a single reagent addition channel can be provided which intersects all of the parallel separation channels. Reagents are then serially introduced into this main reagent introduction channel and delivered to the various separation channels and reaction chambers, using the serial to parallel conversion aspects described herein. Similarly, instead of providing a separate waste reservoir for each of the separation channels, a single transverse channel is optionally provided intersecting the separation channels at their termini opposite the sample introduction channel. This single channel can be used to drive fluid flow, e.g., by applying a voltage at the termini of this transverse channel. By reducing the number of ports at which voltage must be controlled, device design and control are simplified, also as described herein.

Movement of Materials in Microscale Devices

As noted, the present invention provides microfluidic systems and methods of using such systems in the performance of a wide variety of fluidic operations and fluid manipulations. Microfluidic devices or "microlaboratory systems," allow for integration of the elements required for performing these operations or manipulations, automation, and minimal environmental effects on the reaction system, e.g., evaporation, contamination, human error.

The phrase "selective direction" or "selective control" generally refers to the ability to direct or move a particular fluid volume from one area in a microfluidic device, e.g., a chamber or channel, to another area of the microfluidic device. Thus, selective direction includes the ability to move one of several fluids contained within separate regions of a microfluidic device without disturbing the other fluids, the direction of a portion of a fluid volume, as well as the ability to transport or deliver an amount of a particular fluid from a first chamber to a selected one of several interconnected chambers.

Selective flowing, movement and direction of fluids within the microscale fluidic devices is carried out by a variety of methods. For example, the devices optionally include integrated microfluidic structures, such as micropumps and microvalves, or external elements, e.g., pumps and switching valves, for the pumping and direction of the various fluids through the device. Examples of microfluidic structures are described in, e.g., U.S. Pat. Nos. 5,271,724, 5,277,556, 5,171,132, and 5,375,979. See also, Published U.K. Patent Application No. 2 248 891 and Published European Patent Application No. 568 902.

Although microfabricated fluid pumping and valving systems are readily employed in the devices of the invention, the cost and complexity associated with their manufacture and operation can generally prohibit their use in mass-produced and potentially disposable devices as are envisioned by the present invention. The devices of the invention will typically include an electroosmotic fluid direction system. Such fluid direction systems combine the elegance of a fluid direction system devoid of moving parts, with an ease of manufacturing, fluid control and disposability. Examples of particularly preferred electroosmotic fluid direction systems include, e.g., those described in International Patent Application No. WO 96/04547 to Ramsey et al., as well as U.S. Pat. Nos. 6,046,056 and 5,976,336.

In brief, these fluidic control systems typically include electrodes disposed within reservoirs that are placed in fluid connection with the channels fabricated into the surface of the substrate. The materials stored in the reservoirs are transported through the channel system delivering appropriate volumes of the various materials to one or more regions on the substrate in order to carry out a desired screening assay.

Material transport and direction is accomplished through electrokinesis, e.g., electroosmosis or electrophoresis. In brief, when an appropriate fluid is placed in a channel or other fluid conduit having functional groups present at the surface, those groups can ionize. For example, where the surface of the channel includes hydroxyl functional groups at the surface, protons can leave the surface of the channel and enter the fluid. Under such conditions, the surface will possess a net negative charge, whereas the fluid will possess an excess of protons or positive charge, particularly localized near the interface between the channel surface and the fluid. By applying an electric field along the length of the channel, cations will flow toward the negative electrode. Movement of the positively charged species in the fluid pulls the solvent with them. An electrokinetic device moves components by applying an electric field to the components, typically in a microfluidic channel. By applying an electric field along the length of the channel, cations will flow toward a negative electrode, while anions will flow towards a positive electrode. Movement of the charged species in the fluid pulls the solvent with the fluid. The steady state velocity of this fluid movement is generally given by the equation:

$$v = \frac{\epsilon \xi E}{4\pi\eta}$$

where v is the solvent velocity, $\epsilon$ is the dielectric constant of the fluid, $\xi$ is the zeta potential of the surface, E is the electric field strength, and $\eta$ is the solvent viscosity. The solvent velocity is, therefore, directly proportional to the surface potential.

To provide appropriate electric fields, the system generally includes a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple, independent voltage sources are used. The voltage controller is electrically connected to each of the reservoirs via an electrode positioned or fabricated within each of the plurality of reservoirs. In one embodiment, multiple electrodes are positioned to provide for switching of the electric field direction in a microchannel, thereby causing the analytes to travel a longer distance than the physical length of the microchannel.

Substrate materials are also selected to produce channels having a desired surface charge. In the case of glass substrates, the etched channels will possess a net negative charge resulting from the ionized hydroxyls naturally present at the surface. Alternatively, surface modifications are employed to provide an appropriate surface charge, e.g., coatings, derivatization, e.g., silanation, or impregnation of the surface to provide appropriately charged groups on the surface. Examples of such treatments are described in, e.g., U.S. Pat. No. 5,885,470.

Modulating voltages are then concomitantly applied to the various reservoirs to affect a desired fluid flow characteristic, e.g., continuous or discontinuous (e.g., a regularly pulsed field causing the flow to oscillate direction of travel) flow of receptor/enzyme, ligand/substrate toward the waste reservoir with the periodic introduction of test compounds. Particularly, modulation of the voltages applied at the various reservoirs can move and direct fluid flow through the interconnected channel structure of the device in a controlled manner to effect the fluid flow for the desired screening assay and apparatus.

While a number of devices for carrying out particular methods according to the invention are described in substantial detail herein, it will be recognized that the specific configuration of these devices will generally vary depending upon the type of manipulation or reaction to be performed. The small scale, integratability and self-contained nature of these devices allows for virtually any reaction orientation to be realized within the context of the microlaboratory system.

Because the microfluidic devices of the invention preferably employ electroosmotic fluid direction systems, and are substantially sealed to the outside environment, excepting reagent, buffer or sample ports, they are capable of performing fluidic operations while maintaining precise control of the amounts of different fluids to be delivered to the different regions of the substrate.

For example, the sealed nature of the devices prevents substantial evaporation of fluids from the devices. Evaporation, while a problem at the bench scale, becomes substantially more problematic when operating at the microscale, where loss of minute amounts of fluids can have a dramatic effect on concentrations of the non volatile elements of these fluids, particularly where extended reaction times are concerned. Thus, the devices and systems of the invention provide the added advantage of performing fluidic operations with a controlled volume. By "controlled volume" is meant that the systems can transport or direct a particular volume of a particular fluid which is generally within about 10% of an expected or desired volume or amount of that fluid, preferably within about 5% of an expected or desired volume, and often within about 1% of an expected or desired volume.

The phrase "preselected volume" or simply "selected volume" refers to a volume of fluid that is to be subjected to a particular fluid manipulation. Again, as noted above, in the fluid filled chambers, channels and/or reservoirs of the systems of the invention, these preselected volumes are generally transported as slugs of different fluids within these fluid filled elements. Generally, a preselected volume will be within at least about 10% of a desired volume. Thus, where one wishes to transport a preselected volume of 1 $\mu$l of a particular fluid from a first chamber to a second chamber, the fluid direction systems of the present invention would transport 1 $\mu$l±10%. In preferred aspects, these systems will maintain a volume within about 5% and often, within about 1%. In addition to reliable volumetric control, the fluid direction systems of the present invention are generally capable of moving or directing small preselected fluid volumes. For example, the fluid direction systems of the present invention are generally capable of selectively directing volumes of fluid that are less than about 10 $\mu$l, preferably less than about 1 $\mu$l, more preferably less than 0.1 $\mu$l and often less than about 10 nl.

In addition to the volume advantages discussed above, the sealed nature and readily automatable fluid direction systems also protects fluid operation performed in these devices from contaminating influences from the outside environment. Such influences include chemical, biological or microbiological contamination of fluidic operations which can affect an outcome of such operations. In addition, such contaminating influences can include the occurrence of human error that is generally associated with manual operations, e.g., measurement errors, incorrect reagent additions, detection errors and the like.

High quality data generation is achieved through two basic levels of control: "hardware-level" control whereby the instruction set for performing a fluidic operation experiment is coded in fine channels (e.g., 10–100 $\mu$m wide, 1–50 $\mu$m deep), and "software-level" control whereby the movement of fluid and/or materials through the channel network is controlled with exquisite precision by manipulating electric fields introduced into the network through electrodes at channel termini using the methods discussed above. Integrated volumetrics capable of highly precise, sub-nanoliter measurements and dispensing are a feature of this invention. Electronics that allow simultaneous, millisecond-resolution control over large voltage gradients or current changes disposed across the different parts of complex LabChip structures are performed using the techniques described above. This permits fluid or material flow at intersections to be accurately controlled and providing "virtual valves", structures that meter fluid by electronic control with no moving parts. The electric field control and small conduit dimensions allow experimentation to be performed on sub-nanoliter fluid volumes.

Detectors

The substrate typically includes a detection window or zone at which a signal is monitored. This detection window typically includes a transparent cover allowing visual or optical observation and detection of the assay results, e.g., observation of a colorometric, fluorometric or radioactive response, or a change in the velocity of colorometric, fluorometric or radioactive component. Detectors often detect a labeled compound, with typical labels including fluorographic, colorometric and radioactive components. Example detectors include spectrophotometers, photodiodes, microscopes, scintillation counters, cameras, film and the like, as well as combinations thereof. Examples of suitable detectors are widely available from a variety of commercial sources known to persons of skill.

In one aspect, monitoring of the signals at the detection window is achieved using an optical detection system. For example, fluorescence based signals are typically monitored using, e.g., in laser activated fluorescence detection systems which employ a laser light source at an appropriate wavelength for activating the fluorescent indicator within the system. Fluorescence is then detected using an appropriate detector element, e.g., a photomultiplier tube (PMT). Similarly, for screens employing colorometric signals, spectrophotometric detection systems are employed which detect a light source at the sample and provide a measurement of absorbance or transmissivity of the sample. See also, *The Photonics Design and Applications Handbook,* books 1, 2, 3 and 4, published annually by Laurin Publishing Co., Berkshire Common, P.O. Box 1146, Pittsfield, Mass. for common sources for optical components.

In alternative aspects, the detection system comprises non-optical detectors or sensors for detecting a particular characteristic of the system disposed within detection window 116. Such sensors optionally include temperature (useful, e.g., when a reaction produces or absorbs heat, or when the reaction involves cycles of heat as in PCR or LCR), conductivity, potentiometric (pH, ions), amperometric (for compounds that can be oxidized or reduced, e.g., $O_2$, $H_2O_2$, $I_2$, oxidizable/reducible organic compounds, and the like).

Alternatively, schemes similar to those employed for the enzymatic system are optionally employed, where there is a signal that reflects the interaction of the receptor with its ligand. For example, pH indicators which indicate pH effects of receptor-ligand binding can be incorporated into the device along with the biochemical system, i.e., in the form of encapsulated cells, whereby slight pH changes resulting from binding can be detected. See Weaver, et al., *Bio/Technology* (1988) 6:1084–1089. Additionally, one can monitor activation of enzymes resulting from receptor ligand binding, e.g., activation of kinases, or detect conformational changes in such enzymes upon activation, e.g., through incorporation of a fluorophore which is activated or quenched by the conformational change to the enzyme upon activation.

One conventional system carries light from a specimen field to a cooled charge-coupled device (CCD) camera. A CCD camera includes an array of picture elements (pixels). The light from the specimen is imaged on the CCD. Particular pixels corresponding to regions of the substrate are sampled to obtain light intensity readings for each position. Multiple positions are processed in parallel and the time required for inquiring as to the intensity of light from each position is reduced. This approach is particularly well suited to DNA sequencing, because DNA sequencing products are easily labeled using any of a variety of fluorophores known in the art. Many other suitable detection systems are known to one of skill.

Computers

Data obtained (and, optionally, recorded) by the detection device is typically processed, e.g., by digitizing the image and storing and analyzing the image on a computer readable medium. A variety of commercially available peripheral equipment and software is available for digitizing, storing and analyzing a signal or image. A computer is commonly used to transform signals from the detection device into sequence information, reaction rates, or the like. PC (Intel x86 or pentium chip-compatible DOS™, OS2™ WINDOWS™ WINDOWS NT™, WINDOWS95™ or WINDOWS97™ based machines), MACINTOSH™, or UNIX™ based (e.g., SUN™ work station) computers are all commercially common, and known to one of skill. Software for determining reaction rates or monitoring formation of products, or for translating raw sizing data for sequencing products into actual sequence are available, or can easily be constructed by one of skill using a standard programming language such as Visualbasic, Fortran, Basic, Java, or the like. The software is optionally designed to determine product velocities, concentrations, flux relationships, sequence information and the like as described, supra. Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive (e.g., ZipDrive™ sold by Iomega Corporation), and other elements. Inputing devices such as a keyboard or mouse optionally provide for input from a person.

More generally, the microfluidic systems herein typically include control systems for carrying out one or more operations of: controlling fluid movement and direction; monitoring and controlling environmental effects on a microfluidic device; and recording and analyzing data obtained from the microfluidic devices. Typically, such control systems include a programmable computer or processor that is linked, via an appropriate interface, with the other elements of the system. For example, the computer or processor will typically interface with: the voltage controller, to direct the electroosmotic fluid direction system; with a detector disposed adjacent the detection window, to obtain data from the device; and with the device itself, to maintain appropriate reaction conditions within the device, e.g., temperature.

Figure 12:
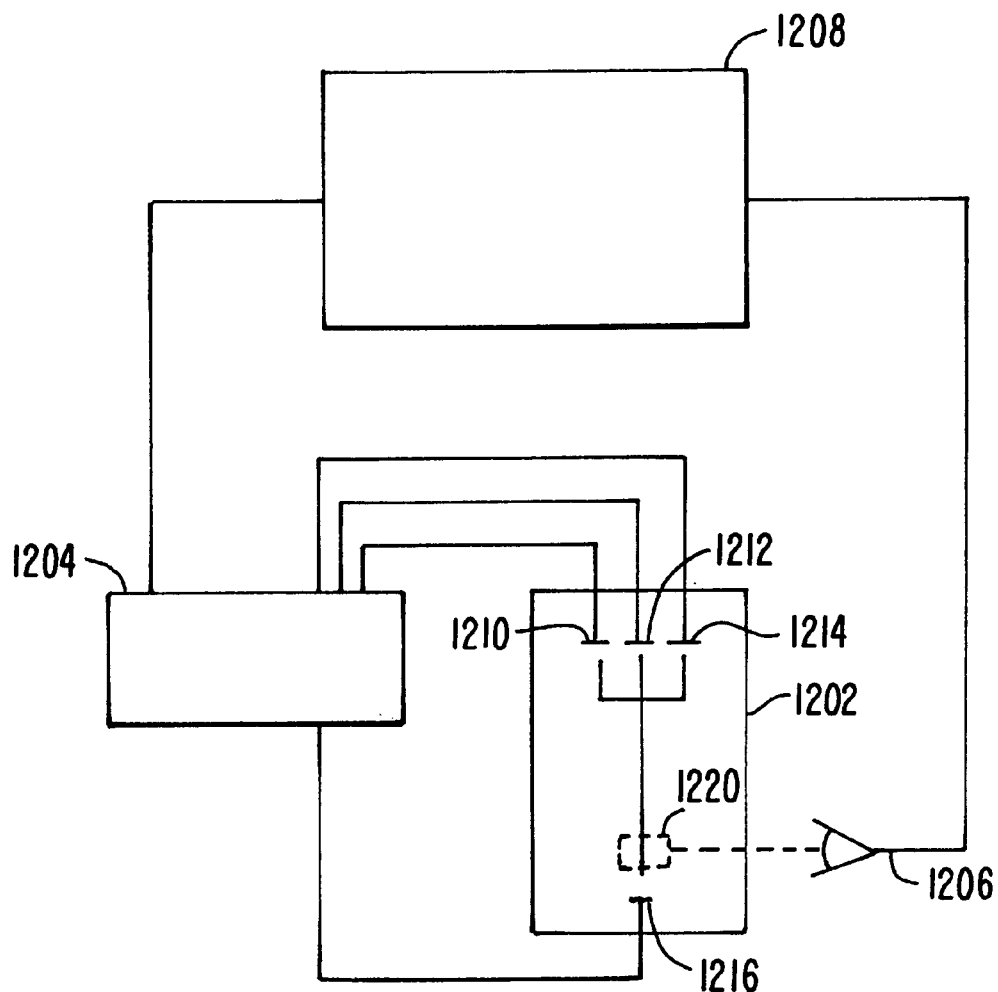
FIG. 12 depicts a block diagram of a control system as connected to a microfluidic device.

Computerized control of the microfluidic systems allows for the repeated, automatic and accurate performance of the various fluidic operations performed within a microfluidic device, or within several devices, simultaneously. Further, the computer is generally programmable so that a user can modify protocols and/or conditions as desired, as well as to record, compile and analyze the data from the device, e.g., statistical analysis. A block diagram of a control system as connected to a microfluidic device is shown in FIG. 12. In particular, the overall system 1200 includes a microfluidic device 1202, a voltage controller 1204, a detector 1206, and a computer or processor 1208. The voltage controller is connected to electrodes 1210–1216 which are placed in electrical contact with fluids in the various ports of the microfluidic device 1202. The voltage controller is, in turn connected to computer 1208. This connection can also include an appropriate AD/DA converter. The computer 1208 is also connected to detector 1206, for instructing operation of the detector, as well as recording data obtained by the detector. Detector 1206 is typically disposed adjacent to an appropriate detection window 1220 within the microfluidic device. In alternate aspects, a detector can be incorporated within the device itself.

Integrated Systems e.g., for Sequencing, Thermocycling, Assay Optimization and Drug Screening The present invention is further illustrated by consideration of the accompanying figures.

Figure 13:
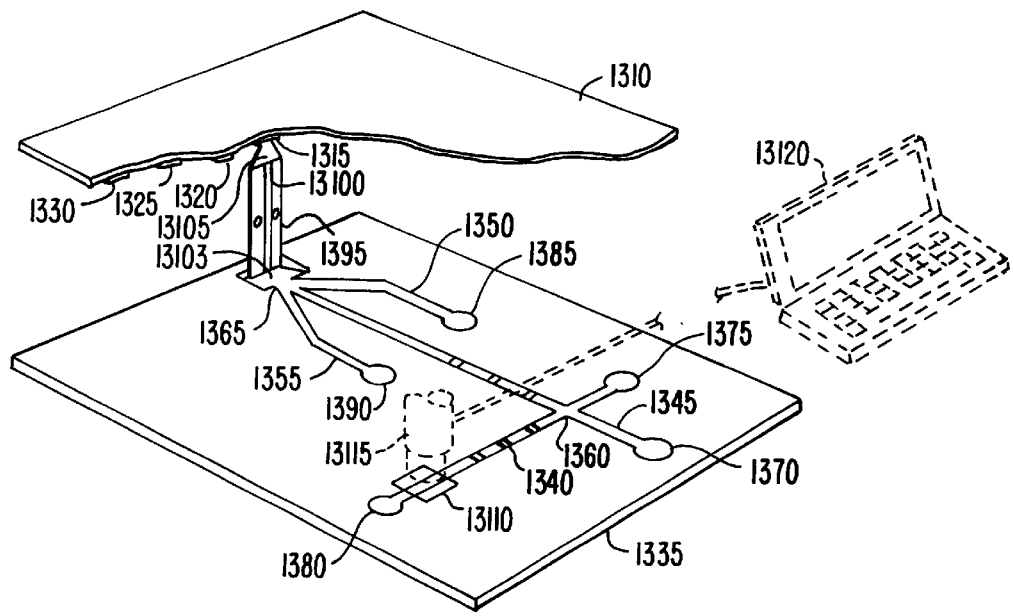
FIG. 13 is a top view of an integrated microfluidic device having a storage substrate in the same plane as an analysis substrate.

FIG. 13 provides an embodiment of the invention having an electropipettor integrated into a microfluidic substrate having a fluid mixing region, a thermocycler region, a size separation region and a detection region. In operation, reagent storage substrate 1300 having dried reagent dots, e.g., 1320–1330 is suspended above or below microfluidic substrate 1305 having channels 1345–1355, intersecting at channel intersections 1360 and 1365 and reagent wells 1370–1390. Channels 1345, 1350 and 1355 are fluidly connected to electropipettor 1395 and channel 13100 in electropipettor 1395. As depicted, optional reagent mixing chamber 13103 provides for mixing of reagents from substrate 1310 prior to entry into channels 1345–1355. In one embodiment, enzyme for a sequencing reaction (i.e., a polymerase enzyme) is stored in well 1390, while dNTPs are stored in well 1385; the components are mixed e.g., in channel 1365 or channel 1345. This is useful, e.g., in embodiments where modular primers are used in a sequencing reaction and more than one primer is needed for the sequencing reaction. It will be appreciated that chamber 13103 is optionally omitted, in which case electropipettor channel 13100 and substrate channels 1345–1355 are directly connected.

Electropipettor tip 13105 is fitted to expel fluid onto primer dots 1315–1330 and to then draw the resulting solubilized primer into channel 13100 for further processing in channels 1345–55, which optionally include mixing, heating, or cooling portions. Reaction products are separated in channel 1340 having detection zone 13110. Products moving through detection zone 13110 are detected by detector 13115 operably coupled to computer 13120. In sequencing embodiments, reagent storage substrate 1310 typically has most or all of the possible primers of a given length, e.g., 4,096 6-mer primers, e.g., in 4,096 separate dots (optionally more than one primer can exist in a single dot, with the selection of sequencing primers taking all of the primers in each dot into account as compared to the template nucleic acid). Computer 13120 is used to select extension primers from reagent storage substrate 1310 according to the selection methods described herein. Sequencing reactions are carried out in channels 1345–1365, optionally including PCR in selected sections of the channels. Sequencing products are detected by detector 13115, and the detection is converted into sequencing information in computer 13120.

Although depicted with reagent storage substrate 1310 over microfluidic substrate 1335, it will be appreciated that reagent storage substrate 1310 can conveniently be either above or below microfluidic substrate 1335. In addition, although depicted with dried reagents, reagent storage substrate 1310 can be substituted with a microtiter dish having reagents in liquid form, although a microtiter dish will usually be located below microfluidic substrate 1335.

Figure 14:
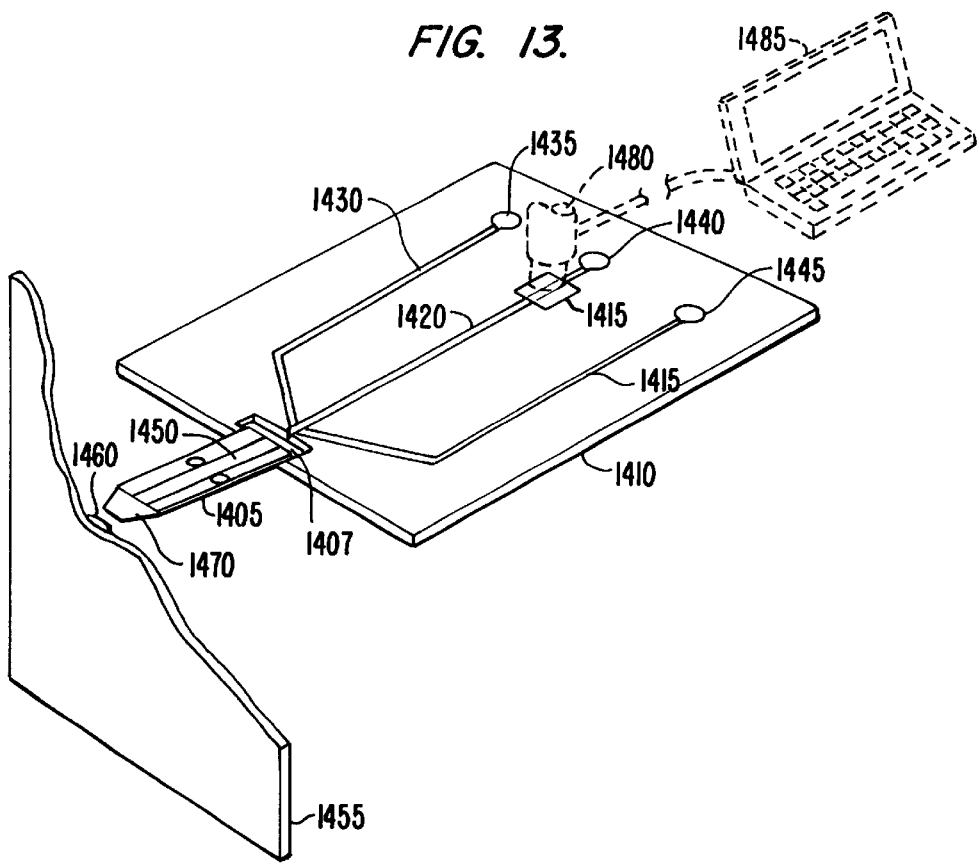
FIG. 14 is a top view of an integrated microfluidic devices having a storage substrate in a plane different from an analysis substrate.

FIG. 14 depicts an alternate embodiment to FIG. 13, in which electropipettor 1405 is in the same plane as microfluidic substrate 1410. Channels 1415, 14140 and 1430 in substrate 1410 are fluidly connected to wells 1435, 1440 and 1445, and are also fluidly connected to channel 1450 in electropipettor 1405 through optional mixing chamber 1407. As depicted, optional reagent mixing chamber 1407 provides for mixing of reagents from substrate 1455 prior to entry into channels 1415, 1420 and 1430. This is useful, e.g., in embodiments where modular primers are used in a sequencing reaction and more than one primer is needed for the sequencing reaction. It will be appreciated that chamber 1407 is optionally omitted, in which case electropipettor channel 1450 and substrate channels 1415, 1420 and 1430 are directly connected. Reagent storage substrate 1455 having dried reagent dots such as dot 1460 is perpendicular (or at an angle) to substrate 1410. Electropipettor 1405 solubilizes dots on reagent storage substrate 1455 by expelling liquid from electropipettor tip 1470 onto dots such as dot 1460, thereby solubilizing the reagent(s) in dot 1460, and withdrawing the reagent(s) into electropipettor tip 1470, channel 1450 and subsequently into substrate 1410. After mixing with additional reagents, e.g. stored in wells 1435, or 1445 and any resulting reaction, reaction products are incubated and separated in channel 1420 and detected in detection region 1475 by detector 1480. Waste materials are stored, e.g., in well 1440. Information regarding the detection is digitized and fed into operably linked computer 1485. As discussed above, the computer translates the information into, e.g., sequence information, drug discovery information or the like and directs selection of a second reagent dot on substrate 1455 (e.g., a second primer) for analysis.

In the embodiments depicted in FIG. 13 and FIG. 14, computers 1320 and 1485 typically store information regarding the location of reagent dots on reagent storage substrates 1310 and 1455. Typically this will be in the form of address information, where the address of each reagent dot on regent storage substrates 1310 or 1455 is stored for subsequent selection steps. Either the relevant microfluidic substrate, electropipettor or reagent storage substrate is moved so that the electropipettor contacts the selected reagent dot (any or all of the components can be moved to cause the electropipettor to contact the proper point on the particular reagent storage substrate. Movement can be conveniently achieved using a mechanical armature in contact with the component to be moved. Alternatively, the components can be moved manually.

Figure 15:
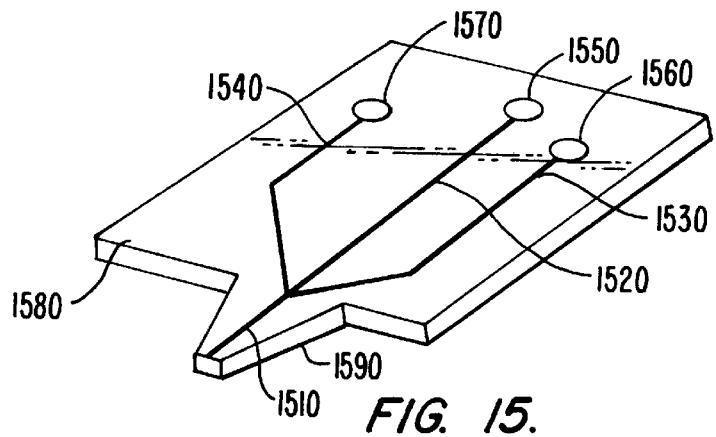
FIG. 15 is a top view of a microfluidic substrate having an integrated electropipettor.

FIG. 15 is an alternate preferred embodiment in which electropipettor channel 1510 is contiguous with microfluidic channels 1520 1530 and 1540 which are connected to wells 1550, 1560 and 1570, respectively. In this embodiment, microfluidic substrate 1580 comprises electropipettor tip 1590, which includes electropipettor channel 1510.

Figure 16:
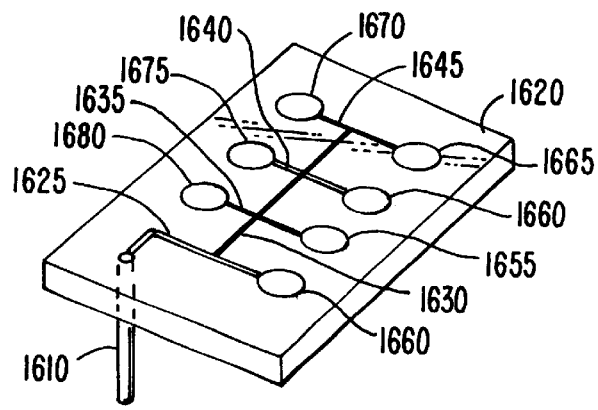
FIG. 16 is a top view of a microfluidic substrate having an integrated electropipettor in the form of a capillary tube.

FIG. 16 is an additional alternate preferred embodiment in which electropipettor capillary 1610 protrudes from microfluidic substrate 1620. Capillary 1610 is in fluid communication with microfluidic channel 1625, which is in fluid communication with channels 1635, 1640, and 1645 and wells 1650–1680.

Figure 17:
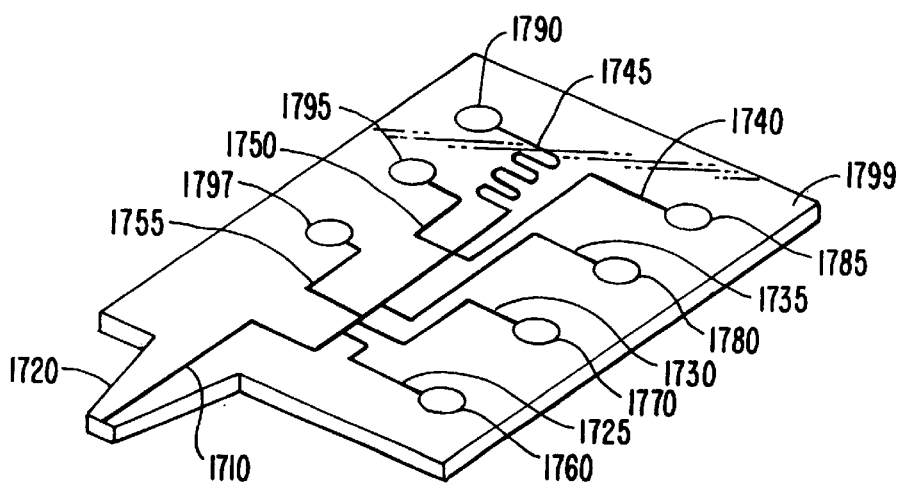
FIG. 17 is a top view of a microfluidic substrate having an integrated electropipettor with serpentine channel geometry useful for electrophoresis.

FIG. 17 is an additional preferred embodiment similar to that depicted in FIG. 15. In operation, electropipettor channel 1710 in electropipettor tip 1720 is fluidly connected to microfluidic channels 1725–1755 and wells 1760–1797 in microfluidic substrate 1799.

It will be appreciated that the embodiments depicted in FIGS. 15–17 can easily by used in an integrated apparatus similar to that depicted in FIG. 13 or FIG. 14, i.e., comprising a reagent storage substrate, armature for moving the reagent substrate and/or the microfluidic substrate, a viewing apparatus such as a microscope or photodiode and a computer for processing data, controlling fluid movement on the substrate, and controlling movement of electropipettor components relative to the reagent storage substrate.

Figure 18:
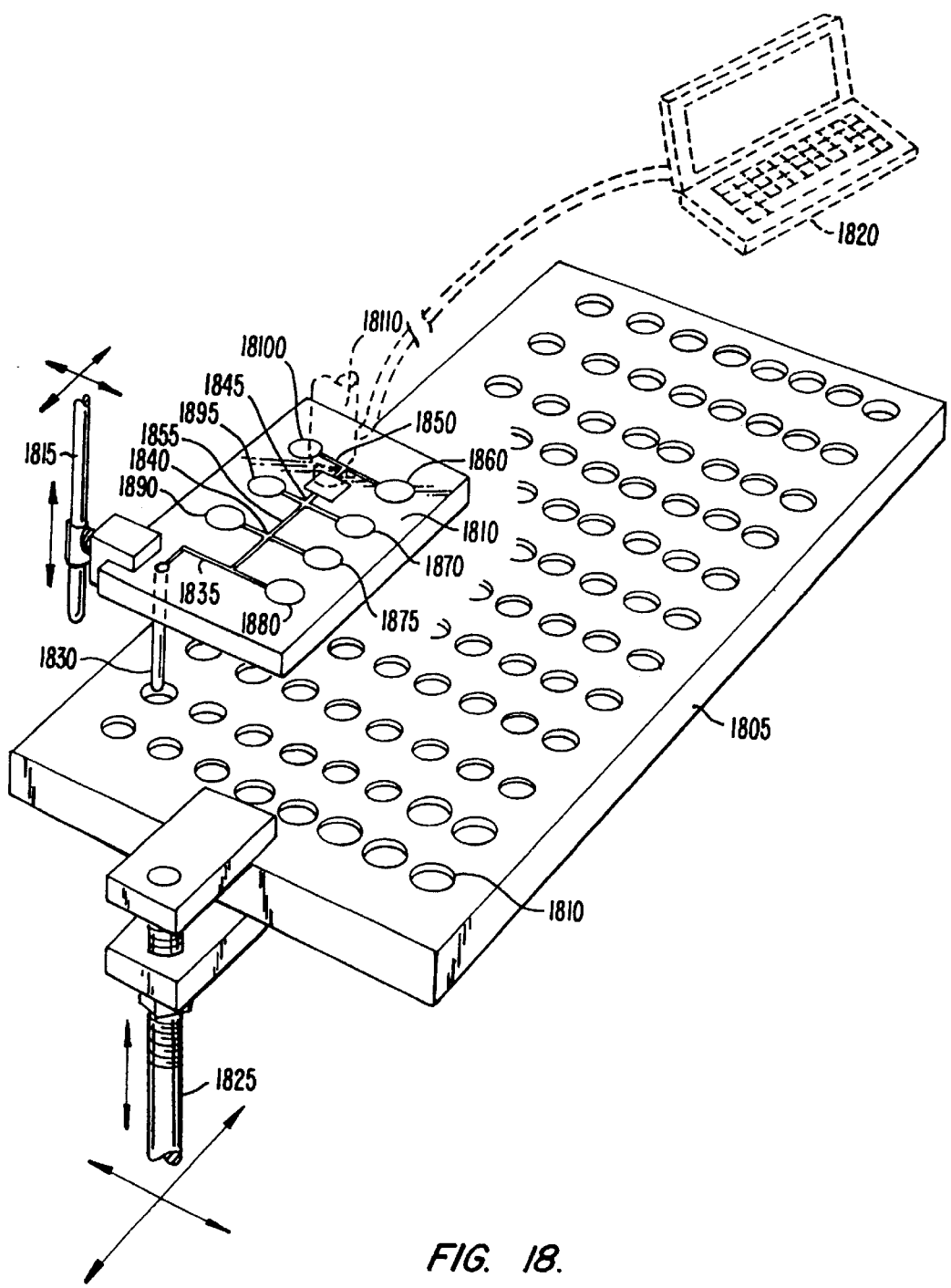
FIG. 18 is a top view of an integrated microfluidic device incorporating a microtiter dish.

Furthermore, it will be appreciated that a variety of reagent storage substrates are appropriate. For example, FIG. 18 provides a preferred integrated apparatus in which reagents to be selected are stored in liquid form. In operation, liquid reagents are stored in liquid reagent storage tray 1805. The reagents are stored in wells 1810 located in reagent storage tray 1805. A variety of reagent storage trays commercially available are suitable for this purpose, including microtiter dishes, which are available e.g. in a 918-well format. Microfluidic substrate 1815 is located over reagent storage tray 1805. For convenience of manipulation, either microfluidic substrate 1815 or microtiter tray 1805 or both can be moved using a robotic armature. As depicted, robotic movable armature 1815 is connected to microfluidic substrate 1810 and moves the substrate relative to reagent storage tray 1805 in response to instructions from computer 1820. Similarly, robotic movable armature 1825 is attached to and moves reagent storage tray 1805 relative to microfluidic substrate 1810 in response to instructions from computer 1820. It will be appreciated that to move microfluidic substrate 1810 relative to reagent storage tray 1805, only one movable armature is need; accordingly, either armature 1815 or armature 1825 is optionally omitted. Similarly, either armature 1815 or armature 1825 can be replaced with a movable platform or the like for moving microfluidic substrate 1810 relative to reagent storage tray 1805, or vice versa.

In operation, microfluidic substrate 1810 is sampled by electropipettor 1830 for sampling reagents from wells 1810. Electropipettor 1830 is fluidly connected to microchannels 1835–1850 and microfluidic substrate wells 1860–18100. Reagent mixing, electrophoresis and the like is performed in microchannels 1835–1850. Typically, an electrokinetic control apparatus such as voltage controller connected to electrodes located in one or more of microfluidic substrate wells 1860–700 controls material transport through microchannels 1835–1850. Detector 18110 detects the results of fluidic mixing assays, such as fluorescent sequencing products, inhibition assays, titrations or the like. The results detected are digitized and read by computer 1820, which selects additional fluidic reagents for additional assays, based upon the results detected. Selection of additional reagents causes movement of movable robotic armature 1825 or 1815, thereby positioning electropipettor 1830 in well 1810 having the selected reagent.

Figure 19:
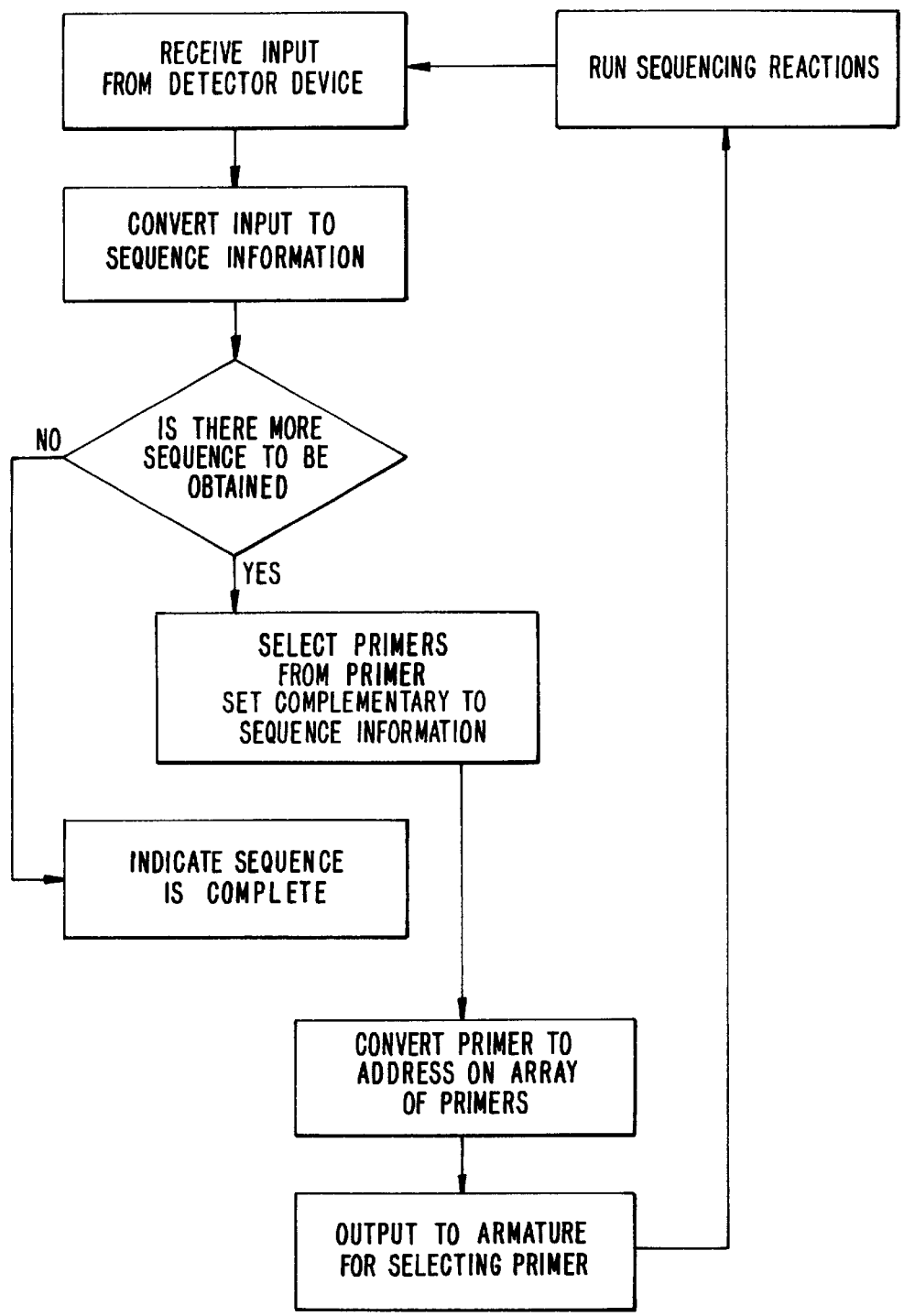
FIG. 19 is a flowchart outlining some of the software processing steps performed by a computer in an integrated system of the invention.

FIG. 19 is an outline of the computer processing steps typical in determining sequence information and in selecting primers useful in the methods and apparatus described herein. Additional processing steps performed to run a voltage controller to direct fluid movement in a microfluidic substrate are optionally performed by the computer.

Figure 20:
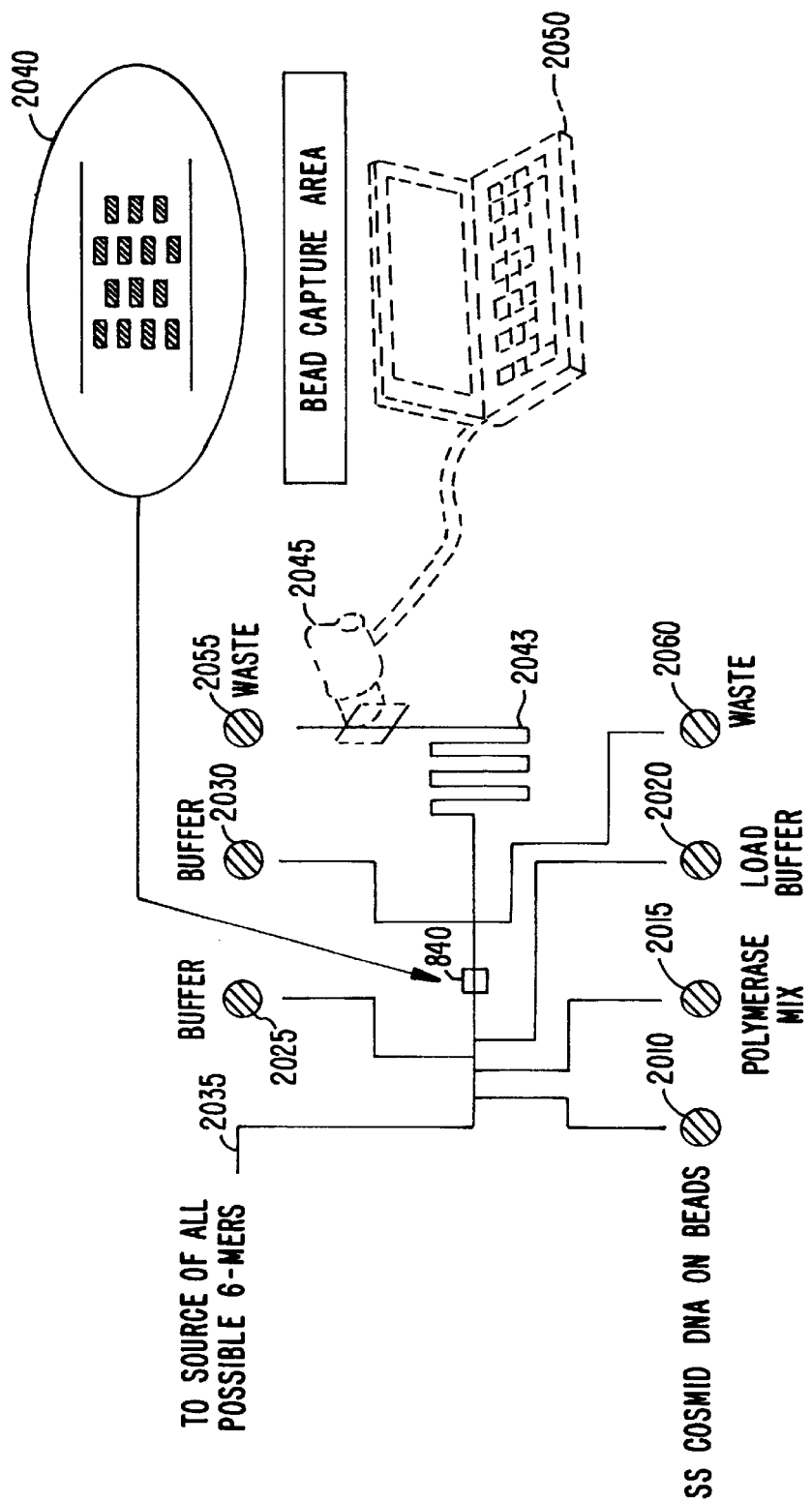
FIG. 20 is a schematic of an integrated system for sequencing nucleic acids.

FIG. 20 provides an embodiment of the invention directed to sequencing. Template DNAs (e.g., single-stranded cosmid DNA, plasmid DNA, viral DNA or the like) to be sequenced is stored in well 2010. The template DNAs are conveniently complexed with capture beads. Sequencing reagents (polymerase, dNTPs, ddNTPs or the like) are stored in well 2015. Buffers for material transport, and or reagents are stored in wells 2020–2030. Electropipettor channel 2035 is connected to a source of all possible 6-mer primers, as described, supra. Template DNA on capture beads (e.g., posts, magnitic beads, polymer beads or the like) from well 2010 is electrokinetically transported to bead capture area 2040. Appropriate primers are selected and transported to bead capture 2040 area using electropipettor channel 2035. Polymerase from well 2015 is contacted with to template DNA in bead capture area 2040. Extension of primers on the template with the polymerase results in sequencing products. The products are washed from the template using loading buffer from well 2020 (the loading buffer optionally comprises a denaturant) and electrophoresed through size separation microchannel 2043. The products separate by size, permitting detection of the products with detector 2045, which is operatively linked to computer 2050. After detection, products enter waste well 2055 After size detection and analysis, computer 2050 directs selection of additional primers to extend sequencing of the template DNAs. Once all of the template is sequenced by repeated cycles of sequencing, the template and beads are in optional embodiments released from bead capture area 2040 using buffer from well 2030 or 2025 and the template DNA beads are transported to waste well 2060. Additional templates are then loaded into well 2010 and the process is repeated with the additional templates.

Figure 21:
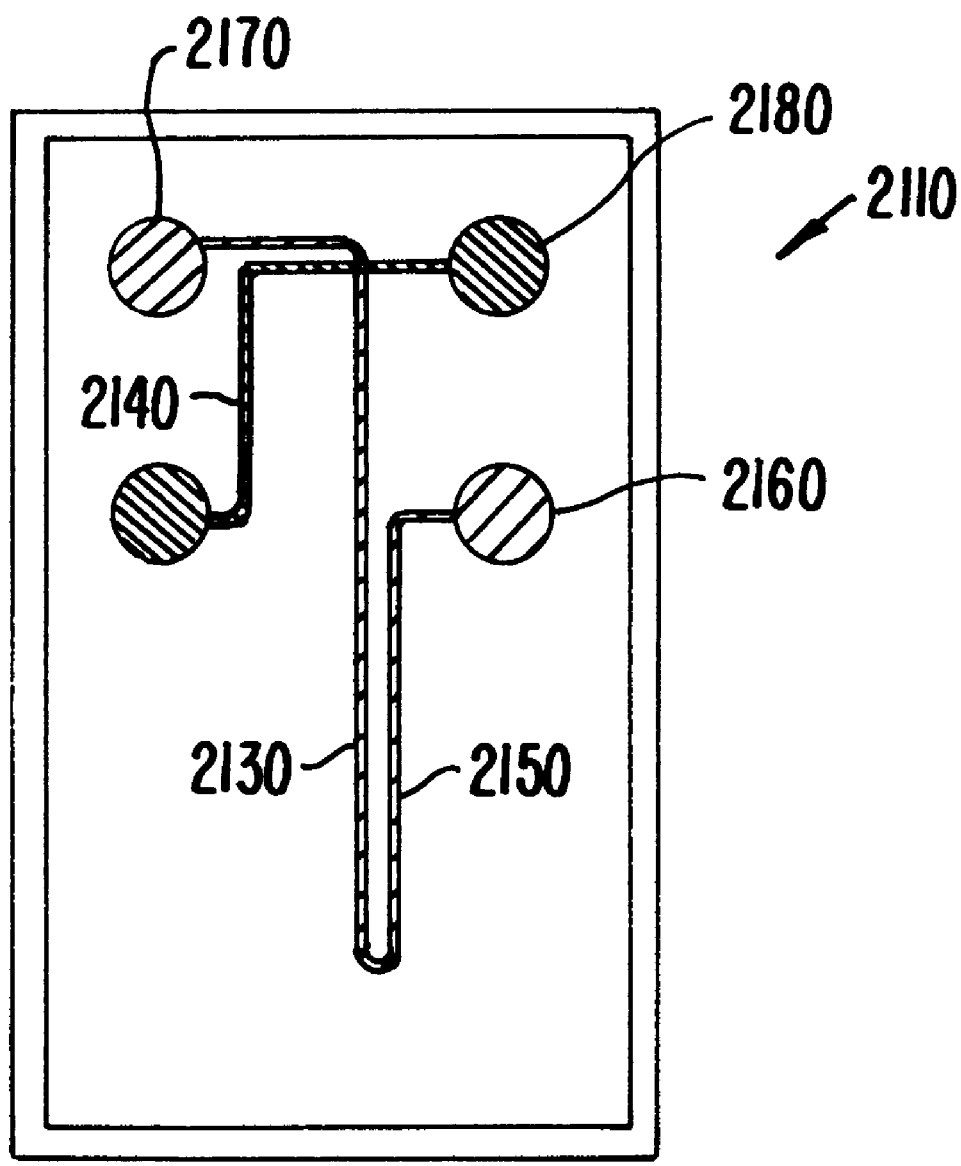
FIG. 21 is a top view of a microchip of the invention.

The labChip depicted in FIG. 21 was used to perform multiple operations in a biochemical assay were run on the chip. This demonstrates the ability to integrate functions such as complex (blood) sample preparation, specialized reaction (polymerase chain reaction, PCR), and sophisticated analysis (DNA size separation) in a single format.

Figure 22:
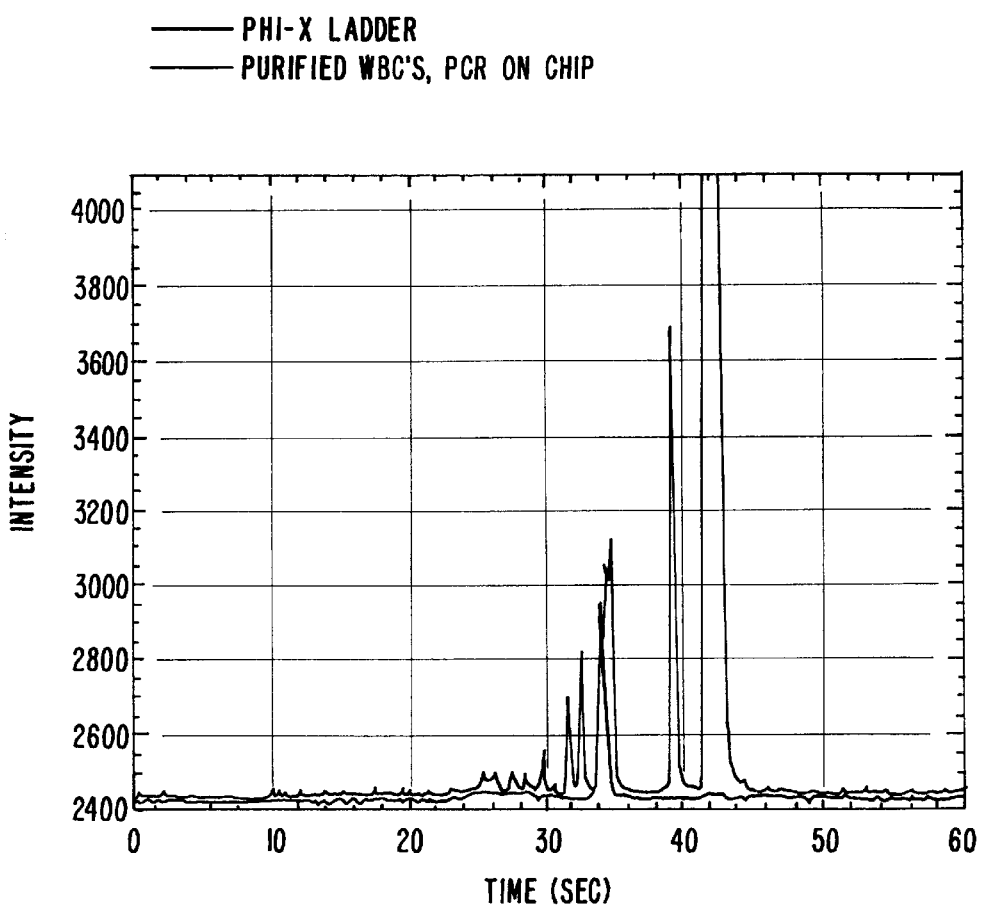
FIG. 22 is an electropherogram for an assay.
Figure 23:
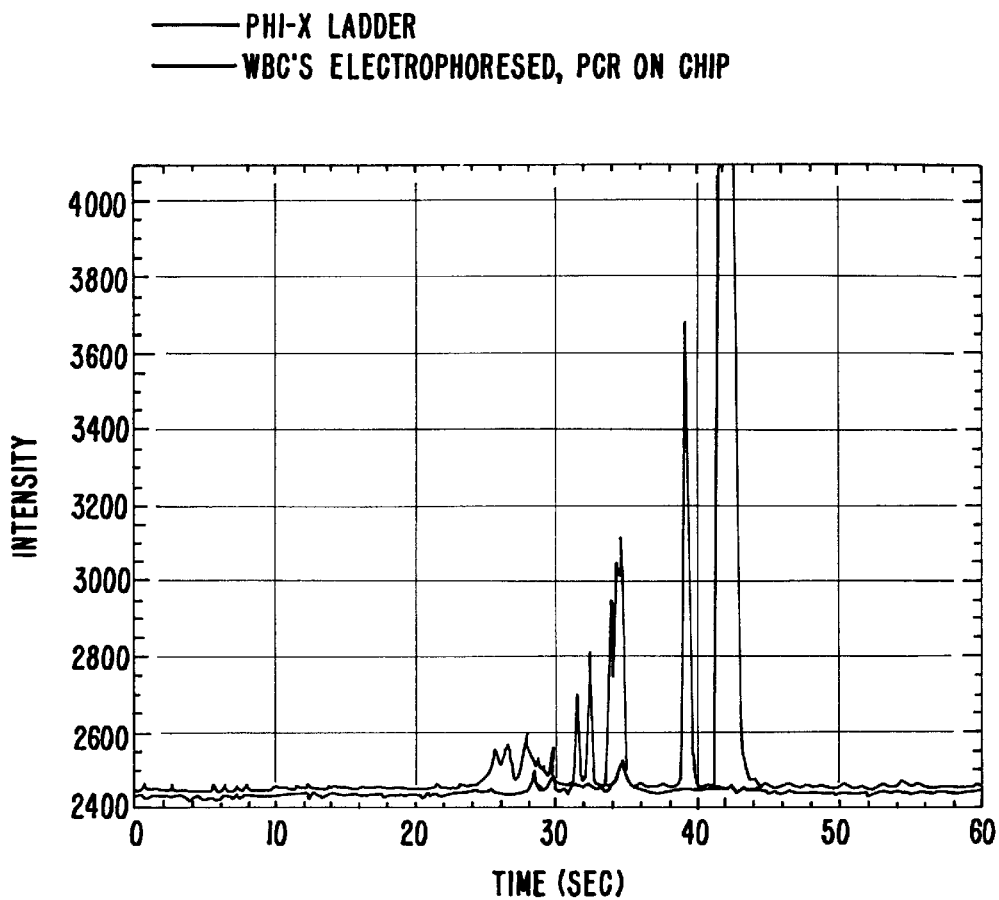
FIG. 23 is an electropherogram for an assay in which white blood cells are electrophoresed.

In the experiment, LabChip™ 2110 was used to prepare wole blood, load DNA template from whole blood, run the PCR reaction and then size the resulting PCR product by gel separation. Channels 2130 and 2140 were filled with sieving matrix gel 2150. In addition, wells 2160 and 2170 at the ends of separation channel 2130 were filled with gel. For the first part of the experiment, approximately 2000 lymphocytes (white blood cells) purified from whole blood in a conventional way (centrifugation) were added to 20 μL of PCR reaction mix and placed in sample well 2180 of chip 2110. The wells were overlaid with mineral oil and the chip was cycled using a thermocycler. After cycling, the PCR product was separated by passage through a second chip through channel 2130. FIG. 22 shows the electropherogram for this portion where the amplified peak of the HLA locus (about 300 bp) is seen at around 34 seconds at the same time as the 270–310 bp fragments in the PhiX 174 standard ladder. For the second part of the experiment, PCR reaction mix without DNA template was placed in well 2180 of a fresh chip and 5% whole blood in which the red blood cells had been lysed was placed in another well. Lymphocytes (white blood cells) were electrophoresed through the channel to the well containing the PCR reaction mixture until 20–100 lymphocytes were in the PCR well. The chip was cycled and DNA separated as for the previous chip. The results are shown in FIG. 23. Amplification was achieved for both purified and electrophoresed lymphocytes, although the amount of product for purified lymphocytes was larger than for electrophoresed lymphocytes. Sufficient PCR cycles were run to ensure that the reaction had reached a plateau stage since the number of starting copies was different. These experiments demonstrate the ability to integrate several steps of a complex biochemical assay on a microchip format.

Modifications can be made to the method and apparatus as hereinbefore described without departing from the spirit or scope of the invention as claimed, and the invention can be put to a number of different uses, including:

The use of an integrated microfluidic system to test the effect of each of a plurality of test compounds in a biochemical system in an iterative process.

The use of an integrated microfluidic system as hereinbefore described, wherein said biochemical system flows through one of said channels substantially continuously, enabling sequential testing of said plurality of test compounds.

The use of a microfluidic system as hereinbefore described, wherein the provision of a plurality of reaction channels in said first substrate enables parallel exposure of a plurality of test compounds to at least one biochemical system.

The use of a microfluidic system as hereinbefore described, wherein each test compound is physically isolated from adjacent test compounds.

The use of a substrate carrying intersecting channels in screening test materials for effect on a biochemical system by flowing said test materials and biochemical system together using said channels.

The use of a substrate as hereinbefore described, wherein at least one of said channels has at least one cross-sectional dimension of range 0.1 to 500 µm.

The use of an integrated system as described herein for nucleic acid sequencing.

An assay, kit or system utilizing a use of any one of the microfluidic components, methods or substrates hereinbefore described. Kits will optionally additionally comprise instructions for performing assays or using the devices herein, packaging materials, one or more containers which contain assay, device or system components, or the like.

In an additional aspect, the present invention provides kits embodying the methods and apparatus herein. Kits of the invention optionally comprise one or more of the following: (1) an apparatus or apparatus component as described herein; (2) instructions for practicing the methods described herein, and/or for operating the apparatus or apparatus components herein; (3) one or more assay component; (4) a container for holding apparatus or assay components, and, (5) packaging materials.

In a further aspect, the present invention provides for the use of any apparatus, apparatus component or kit herein, for the practice of any method or assay herein, and/or for the use of any apparatus or kit to practice any assay or method herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications and patent documents cited in this application are incorporated by reference in their entirety for all purposes to the same extent as if each individual publication or patent document were so individually denoted.

What is claimed is:

1. A microfluidic system, comprising:
   a set of oligonucleotides dried on one or more reagent storage substrates, the set comprising at least 70% of all possible n-mers for a length n, wherein n is at least 4;
   a sample nucleic acid; and,
   a material transport system configured to flow members of the set of oligonucleotides into contact with the nucleic acid sample, wherein the material transport system accesses the one or more reagent storage substrate to flow members of the set of oligonucleotides into contact with the nucleic acid sample.

2. The system of claim 1, wherein the set of oligonucleotides comprises at least 90% of all possible n-mers for length n.

3. The system of claim 1, wherein n is 5.
4. The system of claim 1, wherein n is 6.
5. The system of claim 1, wherein n is between 15 and 20.
6. The system of claim 1, wherein n is less than 15.

7. The system of claim 1, wherein the set of oligonucleotides comprise at least one oligonucleotide that is complementary to the sample nucleic acid.

8. The system of claim 1, wherein the set of oligonucleotides comprises a plurality of oligonucleotides that are complementary to the sample nucleic acid, wherein the plurality of oligonucleotides are contiguously complementary to one or more subsequence of the sample nucleic acid.

9. The system of claim 1, wherein the set of oligonucleotides comprise one or more oligonucleotides that hybridizes to one or more SNP in the sample nucleic acid.

10. The system of claim 1, wherein the set of oligonucleotides comprises one or more oligonucleotide that hybridizes to one or more subsequence in the sample nucleic acid that flanks a SNP in the sample nucleic acid.

11. A microfluidic system, comprising:
    a set of oligonucleotides, the set comprising at least 70% of all possible n-mers for a length n wherein n is at least 4;
    a sample nucleic acid;
    a material transport system configured to flow members of the set of oligonucleotides into contact with the sample nucleic acid; and a molecular beacon which hybridizes to a SNP in the sample nucleic acid.

12. The system of claim 1, wherein the sample nucleic acid is an amplified nucleic acid.

13. The system of claim 1, wherein the material transport system comprises a body structure comprising a plurality of microchannels fabricated therein.

14. The system of claim 1, wherein the material transport system comprises a substrate comprising a plurality of microchannels fabricated therein, wherein the microchannels are machined, etched, or printed in or on the substrate.

15. The system of claim 1, wherein the material transport system comprises one or more electrokinetic, electroosmotic or electrophoretic flow control element.

16. The system of claim 1, wherein the material transport system comprises one or more pump.

17. The system of claim 1, comprising one or more microfluidic channel and a fluidic interface coupling the microfluidic channel to the oligonucleotide set or to one or more additional reagents.

18. The system of claim 17, wherein the fluidic interface comprises one or more capillaries, channels, pins, pipettors, or electropipettors.

19. A microfluidic system, comprising:
    a set of oligonucleotides, the set comprising at least 70% of all possible n-mers for a length n, wherein n is at least 4;
    a sample nucleic acid;
    a material transport system configured to flow members of the set of oligonucleotides into contact with the sample nucleic acid; and a microwell plate comprising the set of oligonucleotides and a substrate comprising at least one microchannel in or one the substrate, the material transport system comprising a capillary channel that extends outward from the substrate, wherein, during operation of the system, the capillary channel is contacted to one or more well of the microwell plate, thereby permitting the material transport system to draw one or more oligonucleotide from the microwell plate into the microchannel.

20. A microfluidic system, comprising:
    a set of oligonucleotides, the set comprising at least 70% of all possible n-mers for a length n, wherein n is at least 4;

a sample nucleic acid;

a material transport system configured to flow members of the set of oligonucleotides into contact with the sample nucleic acid; and a reagent substrate comprising the set of oligonucleotides in dried form on the reagent substrate and a microfluidic substrate comprising at least one microchannel in or on the microfluidic substrate, the material transport system comprising a capillary channel that extends outward from the substrate, wherein, during operation of the system, the capillary channel expels fluid from the tip of the capillary channel onto one or more oligonucleotide on the reagent substrate, thereby solubilizing the oligonucleotide and draws the resulting solubilized oligonucleotide into the capillary channel, thereby permitting the material transport system to draw one or more oligonucleotide from the reagent substrate into the microchannel.

21. A microfluidic system, comprising:

a set of oligonucleotides, the set comprising at least 70% of all possible n-mers for a length n, wherein n is at least 4;

a sample nucleic acid;

a material transport system configured to flow members of the set of oligonucleotides into contact with the sample nucleic acid; and a polymerase.

22. The system of claim 21, where, during operation of the system, at least one of the oligonucleotides is hybridized to the sample nucleic acid, wherein the polymerase extends the oligonucleotide using the sample nucleic acid as a template.

23. The system of claim 21, wherein at least one of the oligonucleotides is hybridized to the sample nucleic acid, wherein the polymerase extends the sample nucleic acid in one or more polymerase chain reaction directed by the system.

24. A microfluidic system, comprising:

a set of oligonucleotides, the set comprising at least 70% of all possible n-mers for a length n, wherein n is at least 4;

a sample nucleic acid;

a material transport system configured to flow members of the set of oligonucleotides into contact with the sample nucleic acid; and a ligase.

25. A microfluidic system, comprising:

a set of oligonucleotides, the set comprising at least 70% of all possible n-mers for a length n, wherein n is at least 4;

a sample nucleic acid;

a material transport system configured to flow members of the set of oligonucleotides into contact with the sample nucleic acid; and a ligase, which ligase ligates one or more members of the set of oligonucleotides, which oligonucleotides are ligated while hybridized to the sample nucleic acid.

26. The system of claim 25, wherein the oligonucleotides are ligated in one or more LCR reaction.

27. A microfluidic system, comprising:

a set of oligonucleotides, the set comprising at least 70% of all possible n-mers for a length n, wherein n is at least 4;

a sample nucleic acid;

a material transport system configured to flow members of the set of oligonucleotides into contact with the sample nucleic acid; and a temperature control element, which element is configured to direct the system to thermocycle the oligonucleotides or the sample nucleic acid, or both.

28. The system of claim 27, wherein the material transport system comprises a body structure comprising a plurality of microchannels fabricated therein, wherein one or more of the microchannels is operably coupled to the temperature control element, which control element controllably heats the one or more microchannels.

29. the system of claim 1, further comprising one or more nucleic acid sequencing or PCR reagents.

30. The system of claim 1, further comprising a detector, which detector is configured to detect hybridization of one or more oligonucleotide to the sample nucleic acid, ligase-mediated extension of one or more oligonucleotide hybridized to the sample nucleic acid, or polymerase-mediated extension of one or more oligonucleotide hybridized to the sample nucleic acid.

31. The system of claim 30, wherein the detector directly detects an amplified product of the hybridization.

32. The system of claim 31, wherein the detector directly detects the amplified product by detecting competitive hybridization of one or more of the oligonucleotides in the oligonucleotide set with the sample nucleic acid.

33. The system of claim 30, wherein the detector is configured for fluorescence polarization spectroscopy.

34. The system of claim 30, wherein detecting hybridization comprises determining a sequence of the sample nucleic acid.

35. The system of claim 34 further comprising a computer, which computer is operably coupled to the detector.

36. The microfluidic system of claim 35, wherein the computer converts one or more signals from the detector into one or more nucleic acid sequences.

37. A system, comprising:

a set of oligonucleotides, the set comprising at least 70% of all possible n-mers for a length n, wherein n is at least 4;

a sample nucleic acid;

a material transport system configured to flow members of the set of oligonucleotides into contact with the sample nucleic acid; and one or more microchannels coupled to the material transport system and one or more DNA size-separation matrices in the one or more microchannels.

38. A method of detecting a nucleic acid in a microfluidic system, the method comprising:

providing a set of oligonucleotides dried on one or more reagent storage substrates, the set comprising at least 70% of all possible n-mers for a length n, wherein n is at least 4;

providing a sample nucleic acid;

flowing at least one oligonucleotide member of the set into contact with the sample nucleic acid;

hybridizing the at least one oligonucleotide member and the sample nucleic acid; and, detecting hybridization of the oligonucleotide member to the sample nucleic acid, thereby determining a sequence of nucleotides of the sample nucleic acid.

39. The method of claim 38, wherein providing the set of oligonucleotides comprises synthesizing the set of oligonucleotides.

40. The method of claim 38, wherein providing the set of oligonucleotides comprises providing at least 90% of all possible oligonucleotides for a length n.

41. The method of claim 38, wherein n is 5.

42. The method of claim 38, wherein n is 6.

43. The method of claim 38, wherein n is between 15 and 20.

44. The method of claim 38, wherein n is less than 15.

45. The method of claim 38, wherein providing the sample nucleic acid comprises performing one or more amplification reactions to produce the sample nucleic acid.

46. A method of detecting a nucleic acid in a microfluidic system, the method comprising:
providing a set of oligonucleotides, the set comprising at least 70% of all possible n-mers for a length n, wherein n is at least 4;
performing one or more amplification reaction to produce a sample nucleic acid;
flowing at least one oligonucleotide member of the set into contact with the sample nucleic acid;
hybridizing the at least one oligonucleotide member and the sample nucleic acid; and
detecting hybridization of the oligonucleotide member to the sample nucleic acid, thereby determining a sequence of nucleotides of the sample nucleic acid, wherein the one or more amplification reaction comprises a ligase-mediated amplification reaction.

47. The method of claim 46, wherein the ligase-mediated amplification reaction comprises a ligase chain reaction (LCR).

48. The method of claim 45, wherein the one or more amplification reaction comprises a polymerase-mediated amplification reaction.

49. The method of claim 48, wherein the polymerase-mediated amplification reaction comprises a polymerase chain reaction (PCR).

50. The method of claim 38, wherein flowing the at least one oligonucleotide member of the set into contact with the sample nucleic acid comprises contacting the at least one oligonucleotide member to the sample nucleic acid in a microscale channel.

51. The method of claim 38, wherein hybridizing the at least one oligonucleotide member of the set into contact with the sample nucleic acid comprises contacting the at least one oligonucleotide member to the sample nucleic acid in a microscale channel under conditions that permit hybridization of the member and the sample nucleic acid.

52. The method of claim 38, wherein hybridization of the oligonucleotide member comprises direct detection of the hybridization of the oligonucleotide member and the sample nucleic acid.

53. The method of claim 52, wherein the direct detection comprises differentially labeled competitive probe hybridization, molecular beacon detection, single nucleotide polymerase extension, or fluorescence polarization.

54. The method of claim 38, wherein detecting a hybridization comprises performing one or more sequencing reactions, whereby a sequence of at least a portion of the sample nucleic acid is determined.

55. A method of detecting a nucleic acid in a microfluidic system, the method comprising:
providing a set of oligonucleotides, the set comprising at least 70% of all possible n-mers for a length n, wherein n is at least 4;
providing a sample nucleic acid;
flowing at least one oligonucleotide member of the set into contact with the sample nucleic acid;
hybridizing the at least one oligonucleotide member and the sample nucleic acid; and
detecting hybridization of the oligonucleotide member to the sample nucleic acid, thereby determining a sequence of nucleotides of the sample nucleic acid, wherein detecting hybridization comprises performing one or more extension reaction by extending the hybridized oligonucleotide member and detecting the resulting extension product.

56. The method of claim 55, wherein the extension reaction comprises one or more dideoxy sequencing reactions.

57. The method of claim 55, wherein detecting the extension product comprises separating the extension product from one or more additional component by size.

58. A method of detecting a nucleic acid in a microfluidic system, the method comprising:
providing a set of oligonucleotides, the set comprising at least 70% of all possible n-mers for a length n, wherein n is at least 4;
providing a sample nucleic acid;
flowing at least one oligonucleotide member of the set into contact with the sample nucleic acid;
hybridizing the at least one oligonucleotide member and the sample nucleic acid; and
detecting hybridization of the oligonucleotide member to the sample nucleic acid, thereby determining a sequence of nucleotides of the sample nucleic acid, wherein detecting hybridization comprises amplifying the sample nucleic acid by extending the oligonucleotide member with a polymerase in one or more PCR or LCR reaction.

59. The method of claim 54, further comprising selecting one or more additional member of the set for hybridization to the sample nucleic acid based upon the sequence hybridizing the one or more additional member to the sample nucleic acid.

60. The method of claim 59, comprising extending the one or more additional member while hybridized to the sample nucleic acid with a polymerase or a ligase.

61. The method of claim 38, comprising heating the at least one oligonucleotide member and sample nucleic acid, before, during or after hybridization of the at least one oligonucleotide member and sample nucleic acid.

* * * * *

UNITED STATES PATENT AND TRADEMARK OFFICE
CERTIFICATE OF CORRECTION

PATENT NO. : 6,670,133 B2
DATED : December 30, 2003
INVENTOR(S) : Knapp et al.

It is certified that error appears in the above-identified patent and that said Letters Patent is hereby corrected as shown below:

<u>Column 60,</u>
Line 18, after "length n", please insert -- , --.
Line 56, after "in or", please delete "one" and insert -- on --.

<u>Column 62,</u>
Line 7, after "29." please delete "the" and insert -- The --.

Signed and Sealed this

Sixteenth Day of March, 2004

JON W. DUDAS
*Acting Director of the United States Patent and Trademark Office*